United States Patent
Wu et al.

(10) Patent No.: US 8,618,110 B2
(45) Date of Patent: Dec. 31, 2013

(54) COMPOSITIONS AND METHODS FOR APOPTOSIS MODULATORS

(75) Inventors: Jay Jie-Qiang Wu, Fremont, CA (US); Ling Wang, Union City, CA (US)

(73) Assignee: VM Discovery Inc., Fremont, CA (US)

( * ) Notice: Subject to any disclaimer, the term of this patent is extended or adjusted under 35 U.S.C. 154(b) by 0 days.

(21) Appl. No.: 12/702,651

(22) Filed: Feb. 9, 2010

(65) Prior Publication Data

US 2010/0267671 A1    Oct. 21, 2010

Related U.S. Application Data

(63) Continuation-in-part of application No. PCT/US2008/072601, filed on Aug. 8, 2008.

(60) Provisional application No. 60/955,293, filed on Aug. 10, 2007, provisional application No. 61/046,782, filed on Apr. 21, 2008.

(51) Int. Cl.
| | |
|---|---|
| A61K 31/5377 | (2006.01) |
| A61K 31/496 | (2006.01) |
| A61K 31/454 | (2006.01) |
| A61K 31/422 | (2006.01) |
| A61K 31/4192 | (2006.01) |
| C07D 487/04 | (2006.01) |
| C07D 417/14 | (2006.01) |
| C07D 413/14 | (2006.01) |
| C07D 413/12 | (2006.01) |
| C07D 413/10 | (2006.01) |
| C07D 405/14 | (2006.01) |
| C07D 401/14 | (2006.01) |
| C07D 401/06 | (2006.01) |
| C07D 403/14 | (2006.01) |
| C07D 403/10 | (2006.01) |
| C07D 403/06 | (2006.01) |

(52) U.S. Cl.
USPC ........... 514/254.06; 514/252.18; 514/252.19; 514/253.04; 514/253.1; 514/253.11; 514/254.02; 514/254.04; 514/232.8; 514/278; 514/322; 514/375; 514/377; 514/359; 544/121; 544/349; 544/357; 544/364; 544/367; 544/366; 548/217; 548/259; 546/16; 546/199

(58) Field of Classification Search
USPC .............. 514/252.18, 252.19, 253.04, 253.1, 514/253.11, 254.02, 254.04, 254.06, 232.8, 514/278, 322, 375, 377, 359; 544/121, 349, 544/357, 364, 367, 366; 546/16, 199; 548/217, 259

See application file for complete search history.

(56) References Cited

U.S. PATENT DOCUMENTS

| | | |
|---|---|---|
| 3,530,139 A | 9/1970 | Reeder et al. |
| 5,064,844 A | 11/1991 | O'Mahony et al. |
| 6,339,046 B1 | 1/2002 | Nebel et al. |

FOREIGN PATENT DOCUMENTS

| | | |
|---|---|---|
| WO | WO 2005/033048 A2 | 4/2005 |
| WO | WO 2008021250 A2 * | 2/2008 |

OTHER PUBLICATIONS

Radaeva et al. Russian Journal of Organic Chemistry 2005, 41, 907-909.*
Fura, A. DDT, 2006, 11, pp. 133-142.*
Anari et al. DDT, 2005, 10, pp. 711-717.*
Nedderman, A. N. R. Biopharm. Drug Dispos. 2009, 30, pp. 152-162.*
CAS Registry Entry for CAS Registry No. 380572-62-3, which entered STN on Jan. 7, 2002.*
CAS Registry Entry for CAS Registry No. 396101-12-5, which entered STN on Feb. 27, 2002.*
CAS Registry Entry for CAS Registry No. 374921-95-6, which entered STN on Dec. 13, 2001.*
Young, "International Search Report," 4 pages, from International Patent Appl. No. PCT/US08/72601, United States Patent and Trademark Office, Alexandria, Virginia, USA (mailed Jan. 6, 2009).
Young, "Written Opinion of the International Searching Authority," 10 pages, from International Patent Appl. No. PCT/US08/72601, United States Patent and Trademark Office, Alexandria, Virginia, USA (mailed Jan. 6, 2009).

* cited by examiner

*Primary Examiner* — Joseph Kosack
*Assistant Examiner* — Matthew Coughlin
(74) *Attorney, Agent, or Firm* — Cooley LLP

(57) ABSTRACT

The present invention includes and relates generally to compounds of structural Formula (I), or a salt, solvate, or prodrug thereof, which modulate apoptosis in cells. The present invention also provides pharmaceutical compositions containing these compounds, methods of making these compounds, and methods of using these compounds and pharmaceutical compositions for treatment of diseases associated with irregular apoptosis in cells.

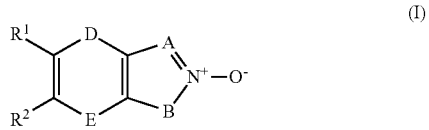

(I)

2 Claims, 3 Drawing Sheets

US 8,618,110 B2

COMPOSITIONS AND METHODS FOR APOPTOSIS MODULATORS

1. CROSS-REFERENCE TO RELATED APPLICATIONS

Figure 1A:
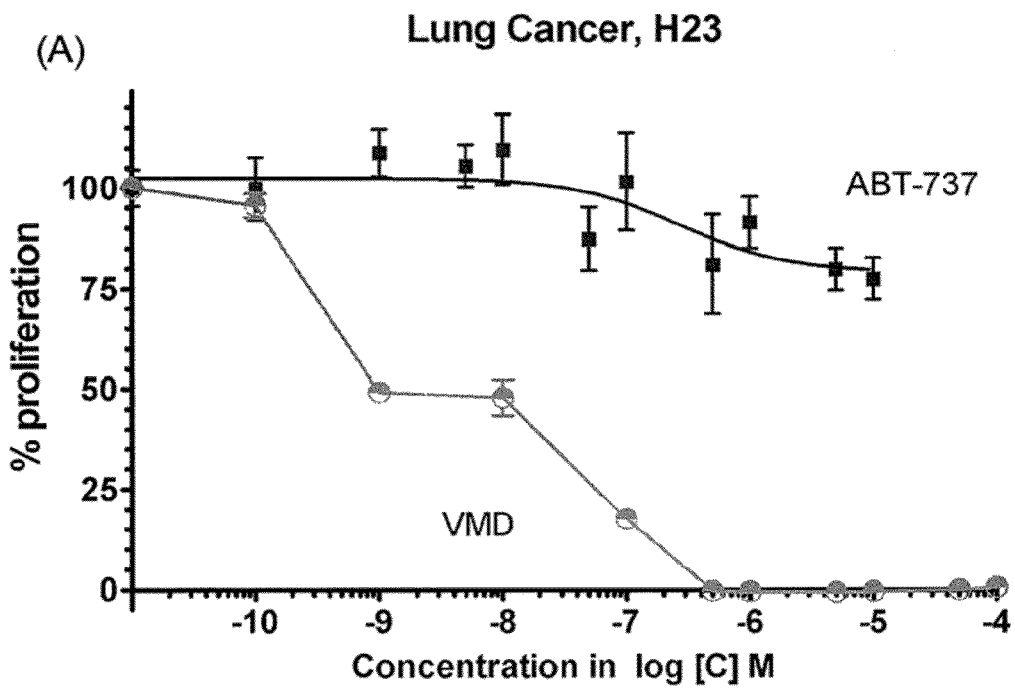

This application is a continuation-in-part application of the International Application No. PCT/US2008/072601, filed on Aug. 8, 2008 and published as WO 2009/023558, which claims priority to U.S. Provisional Patent Application Ser. No. 60/955,293, entitled "Compositions and Methods for Modulating Apoptosis in Cells Which Over-Express Bcl-2 Proteins", filed Aug. 10, 2007; and U.S. Provisional Patent Application Ser. No. 61/046,782, entitled "Compositions of Triazole-Oxide or Indazole-Oxide and Their Uses as Apoptosis Modulators", filed Apr. 21, 2008. The content of these applications are herein incorporated by reference in their entirety for all purposes.

2. FIELD OF THE INVENTION

The present invention relates generally to compounds which modulate apoptosis in cells, pharmaceutical compositions of these compounds, methods of making these compounds and methods of using these compounds and pharmaceutical compositions thereof related to regulation of apoptosis in cells.

3. BACKGROUND OF THE INVENTION

Apoptosis is a form of programmed cell death in multicellular organisms. It is also considered as engineered cell death to destroy threat to organism integrity and protect proper growth. Many diseases, such as, for examples, lymphoproliferative conditions, cancer (including drug resistant cancer), arthritis, inflammation, autoimmune diseases, may result from down regulation of cell death signals. Furthermore, some DNA viruses, (e.g., Epstein-Barr virus, African swine fever virus, adenovirus, etc.), use host cellular machinery for viral replication and modulate apoptosis to repress cell death thereby enabling the host to produce the virus.

Most chemotherapeutic agents target cellular DNA and induce apoptosis in tumor cells (Fisher et al., *Cell* 78:539-542, 1994). A decreased sensitivity to induction of apoptosis has emerged as a major mode of drug resistance. Members of the evolutionarily conserved Bcl-2 family are important regulators of apoptotic cell death and survival. The anti-apoptotic proteins Bcl-2, Bcl-$x_L$, Bcl-w, A1 and Mcl-1 are death antagonists while pro-apoptotic proteins Bax, Bak, Bad, Bcl-xs, Bid, and Bik are death agonists (Kroemer et al., *Nature Med.* 6:614-620, 1997). Over-expression of anti-apoptotic proteins, for examples, Bcl-2, Bcl-$x_L$ and Mcl-1 confers resistance to multiple chemotherapeutic agents (including alkylating agents, antimetabolites, topoisomerase inhibitors, microtubule inhibitors and anti-tumor antibiotics) on cancer cells and constitute a mechanism of clinical chemoresistance in certain tumors (Minn et al., *Blood* 86:1903-1910, 1995; Decaudin et al., *Cancer Res.* 57:62-67, 1997). Therapies directed to inhibiting Bcl-2, Bcl-$x_L$ and/or Mcl-1 such as those using either anti-sense oligonucleotides or novel protein-targeted drugs, can increase cellular sensitivity to standard agents in vitro or, in some cases, kill cells as single agents (Jansen et al., *Nat. Med.* 4:232-234, 1998).

For many years, hypoxia in cancer cells has been a large therapeutic problem because hypoxia helps tumor cells become more resistant to radiotherapy and chemotherapy. Selectively targeting hypoxic cancer cells is considered to be a novel chemotherapy. Unlike normal cells, solid tumor often exhibits low oxygen tension (pO$_2$<0.33%, 2.5 mmHg) (Hiraoka et al, *Cancer Sci* 2003, 94, 1021-1028). Many compounds containing oxygen-sensitive free radicals are therefore used as hypoxia-selective drugs. Free radicals break DNA strand in low oxygen level and exhibit cytotoxicity against cancer cells (Wondrak et al, *Curr Op Inv Drug,* 2007 8(12), 1022-1037).

There still exists a strong need for novel compounds which can modulate apoptosis in cells. The present invention satisfies these and other needs by providing compounds described below.

4. SUMMARY OF THE INVENTION

In one embodiment, the present invention provides compounds having structural formula (I):

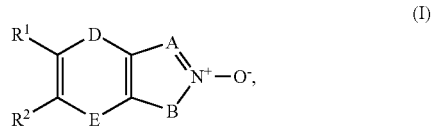

or a salt, solvate, or physiologically functional derivative thereof.

In another embodiment, the present invention provides pharmaceutical compositions comprising one or more compounds as described above or a salt, solvate, or physiologically functional derivative thereof, in combination of a pharmaceutically acceptable vehicle.

In still another embodiment, the present invention provides methods for modulating apoptosis in cells comprising contacting the cells with an apoptosis-modulating amount of the compound as described above, or a salt, solvate, or physiologically functional derivative thereof.

In still another embodiment, the present invention provides methods of treating a disease or condition associated with apoptosis in a patient in need thereof comprising administering to the patient a therapeutically effective amount of the compound as described above, or a salt, solvate, or physiologically functional derivative thereof.

5. BRIEF DESCRIPTION OF THE DRAWINGS

Figure 1B:
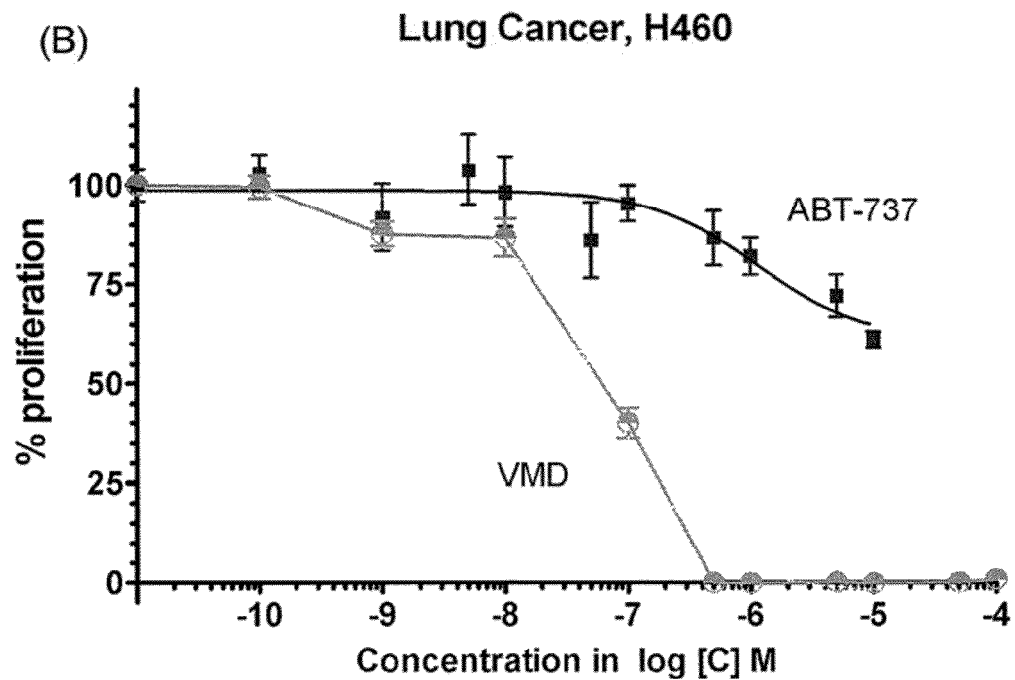
Figure 1C:
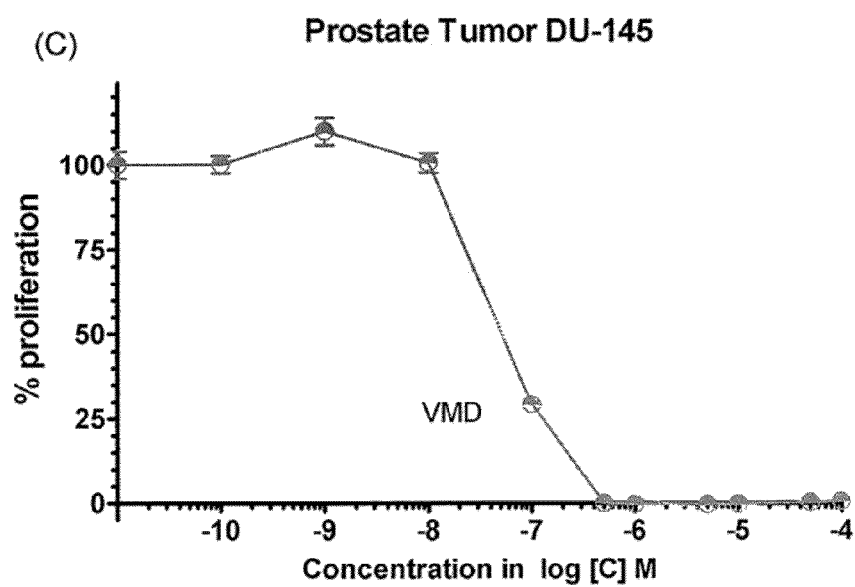

FIGS. 1A, 1B, and 1C. Effects of a compound of the present invention (VMD) in inhibiting tumor growth or proliferation in in vitro human tumor cell line assays of (A) H23 (lung), (B) H460 (lung) and (C) DU-145 (prostate). For comparison, one of most potent Bcl-2/Bcl-xL inhibitors reported in the literature, Abt-737 was also tested. The IC$_{50}$ values of Abt-737 in these tumor cell lines are in high μM range, which are at least two-order of magnitude less potent than the IC50 values (nM range) of VMD in the same cell lines.

Figure 2A:
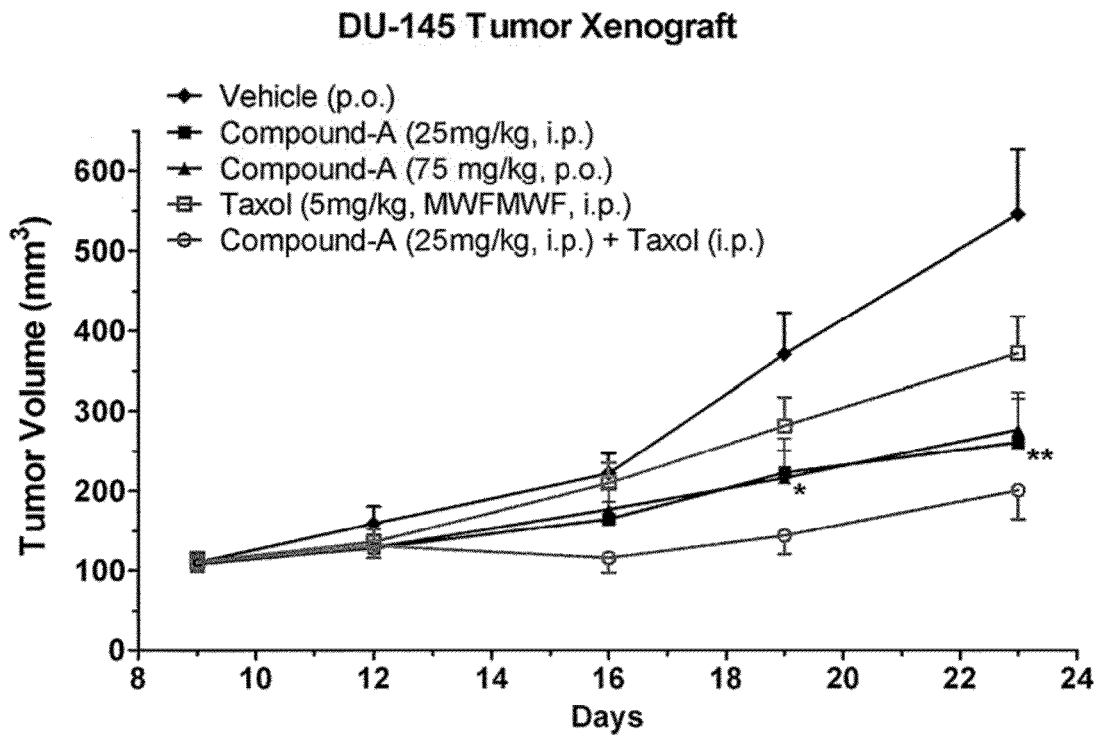
Figure 2B:
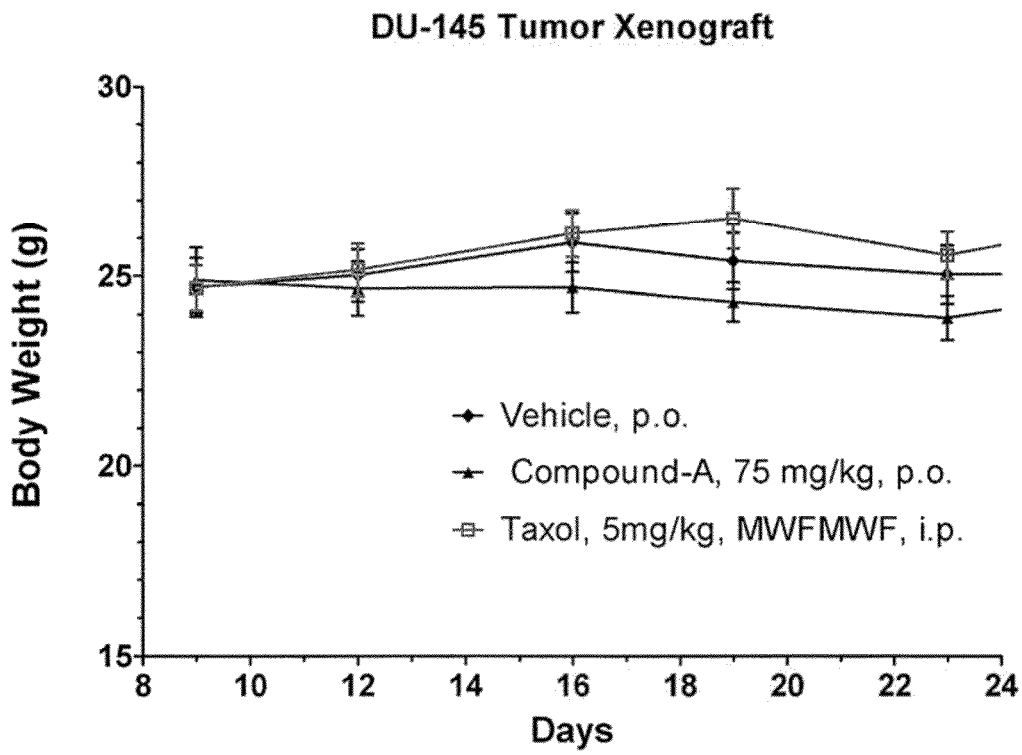

FIGS. 2A and 2B. Effects of a compound of present invention (Compound-A) in inhibiting tumor growth in an in vivo human prostate (DU-145) tumor xenograft assay in nude mice (n=10 mice/group, details see Section 6.9. Biological Experiments). Tumor volume is expressed as Mean±SEM. * P<0.05, ** P<0.01 compared to Vehicle.

6. DETAILED DESCRIPTION OF THE INVENTION

6.1 Definitions

Terms used in the claims and specification are defined as set forth below unless otherwise specified.

The term "a compound of the present invention", "the compound of the present invention", "compounds of the present invention", or "the present compounds" refers to one or more compounds encompassed by the structural formulae and/or any subgeneric formulae disclosed herein and includes any specific compounds and any their physiologically functional derivatives within these generic formula whose structure is disclosed herein. Compounds of the present invention may contain one or more chiral centers and/or double bonds and therefore, may exist as stereoisomers, such as double-bond isomers (i.e., geometric isomers), the racemic mixtures, enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. The compounds of the present invention may also exist in several tautomeric forms. Accordingly, the chemical structures depicted herein encompass all possible tautomeric forms of the illustrated compounds. Compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, $^{18}$O, etc. Compounds may exist in unsolvated forms as well as solvated forms, including hydrated forms and as N-oxides. In general, the salt, hydrated, solvated, and N-oxide forms are within the scope of the present invention. Certain compounds of the present invention may exist in multiple crystalline forms or an amorphous form. In general, all physical forms are equivalent for the uses contemplated by the present invention and are intended to be within the scope of the present invention.

The term "physiologically functional derivative(s)" as used herein refers to any physiologically tolerated derivative of a compound of the present invention, for example, an ester or prodrug, which, upon administration to a mammal, e.g., a human, is transformed directly or indirectly to a compound of the present invention, or an active metabolite thereof. Physiologically functional derivatives include prodrugs of the compounds of the present invention. Examples of prodrug are described in H. Okada et al., *Chem. Pharm. Bull.* 1994, 42, 57-61. Such prodrugs can be metabolized in vivo to a compound of the invention. These prodrugs may themselves be active or not.

"Apoptosis-associated disease" or "a disease or condition associated with apoptosis" includes diseases, disorders, and conditions that are linked to an increased or decreased state of apoptosis in at least some of the cells of a patient. Such diseases include, but are not limited to, neoplastic disease (e.g., cancer and other proliferative diseases), tumor formation, arthritis, inflammation, autoimmune disease, human immunodeficiency virus (HIV) immunodeficiency syndrome, neurodegenerative diseases, myelodysplastic syndromes (such as aplastic anemia), ischaemic syndromes (such as myocardial infarction), liver diseases which are induced by toxins (such as alcohol), alopecia, damage to the skin due to UV light, lichen planus, atrophy of the skin, cataract, and graft rejections and other premalignant and noneoplastic hyperproliferative disorders. Apoptosis-associated diseases also include drug resistance associated with increased or decreased levels of a Bcl-2 family member protein as well as multiple chemotherapeutic drug resistance.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl, cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-propan-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is $(C_1-C_{20})$ alkyldiyl, more preferably, $(C_1-C_{10})$ alkyldiyl, most preferably, $(C_1-C_6)$ alkyldiyl.

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used.

"Acyl" by itself or as part of another substituent refers to a radical —C(O)R$^{200}$, where R$^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Amino" by itself or as part of another substituent refers to a radical —NR$^a$R$^b$, where R$^a$ and R$^b$ are independently hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein, or alternatively R$^a$ and R$^b$, taken together with the atoms to which they are bonded, form a cycloheteroalkyl ring. Representative examples include, but are not limited to —NH$_2$, —NHCH$_3$, —N(CH$_3$)$_2$, —NH-phenyl, —NH—CH$_2$-phenyl, pyrrolidine, and the like.

"Aryl" by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl" by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Aryloxy" by itself or as part of another substituent, refers to a radical of the formula —O—R$^{201}$, where R$^{201}$ is aryl, substituted aryl, arylalkyl, or substituted arylalkyl.

"Aryloxycarbonyl" by itself or as part of another substituent, refers to a radical of the formula —C(O)—O—R$^{201}$, where R$^{201}$ is aryl, substituted aryl, arylalkyl, or substituted arylalkyl.

"Cycloalkyl" or "carbocyclyl" by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, a cycloalkyl group comprises from 3 to 10 ring atoms ($C_3$-$C_{10}$ cycloalkyl). In other embodiments, a cycloalkyl group comprises from 3 to 7 ring atoms ($C_3$-$C_7$ cycloalkyl).

"Cycloheteroalkyl" or "heterocyclyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, B, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, borolane, dioxaborolane, and the like. In some embodiments, the cycloheteroalkyl group comprises from 3 to 10 ring atoms (3-10 membered cycloheteroalkyl). In other embodiments, the cycloalkyl group comprise from 5 to 7 ring atoms (5-7 membered cycloheteroalkyl).

A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to —O—, —S—, —O—O—, —S—S—, —O—S—, —NR$^{203}$R$^{204}$—, =N—N=, —N=N—, —N=N—NR$^{205}$R$^{206}$, —PR$^{207}$—, —P(O)$_2$—, —POR$^{208}$—, —O—P(O)$_2$—, —SO—, —SO$_2$—, —SnR$^{209}$R$^{210}$—, —BR$^{211}$R$^{212}$, BOR$^{213}$OR$^{214}$ and the like, where R$^{203}$, R$^{204}$, R$^{205}$, R$^{206}$, R$^{207}$, R$^{208}$, R$^{209}$, R$^{210}$, R$^{211}$, R$^{212}$, R$^{213}$ and R$^{214}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, furopyridine, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is (C$_1$-C$_3$) alkyl and the heteroaryl moiety is a 5-10 membered heteroaryl.

"Heteroaryloxy" by itself or as part of another substituent, refers to a radical of the formula —O—R$^{201}$, where R$^{201}$ is heteroaryl, substituted heteroaryl, heteroarylalkyl, or substituted heteroarylalkyl.

"Heteroaryloxycarbonyl" by itself or as part of another substituent, refers to a radical of the formula —C(O)—O—R$^{201}$, where R$^{201}$ is heteroaryl, substituted heteroaryl, heteroarylalkyl, or substituted heteroarylalkyl.

"Modulate" or "modulating" refers to adjusting, varying, or changing. As used herein, modulation of cell apoptosis process includes antagonizing, agonizing, or partially antagonizing. That is, the compounds of the present invention may act as antagonists, agonists, or partial antagonists of the apoptosis process.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, B, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" or "subject" includes, but is not limited to, animals such as, for example, mammals. Preferably, the patient is a human.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute, i.e., a compound of the present invention), or an aggregate that consists of a solute ion or molecule (the compound of the present invention) with one or more solvent molecules.

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., *J. Pharm. Sci.* 78: 122-126 (1989). Thus, one of ordinary skill in the art knows how to prepare these precursors, prodrugs or softdrugs with commonly employed techniques of organic synthesis.

"Substituted" when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$N^cR^c$—, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, $NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, substituted alkyl, arylalkyl, alkyldiyl, substituted alkyldiyl, aryl, substituted aryl, arylalkyl, substituted arylalkyl, heteroalkyl, substituted heteroalkyl, heteroalkyldiyl, substituted heteroalkyldiyl, heteroaryl, substituted heteroaryl, heteroarylalkyl substituted heteroarylalkyl; each $R^b$ is independently hydrogen or $R^a$; and each $R^c$ is independently $R^b$ or alternatively, the two $R^c$s are taken together with the nitrogen atom to which they are bonded form a cycloheteroalkyl ring which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —OS $(O)_2O^-$, $OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —OC $(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —N $R^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^c$, —$O^-$, —$OR^b$, —$SR^b$, —$S^-$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —N $R^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above.

"Treating", "treat" or "treatment" of any disease or disorder refers, in some embodiments, to ameliorating or preventing the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Apoptosis-modulating amount" means the amount of a compound that, when in contact with cells having irregular apoptosis, is sufficient to regulate (including both up-regulate and down-regulate) apoptosis of such cells.

"Vehicle" refers to a diluent, adjuvant, excipient or carrier with which a compound is administered.

The phrases "an effective amount" and "an amount sufficient to" refer to amounts of a biologically active agent that produce an intended biological activity.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

6.2 Compounds

In one aspect, the present invention provides a compound having structural Formula (I):

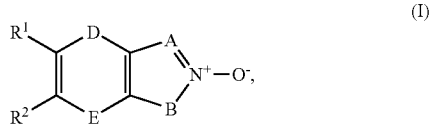

or a salt, solvate, or physiologically functional derivative thereof;
wherein: A is N or $C(R^4)$; B is $N(R^5)$, $C(R^6R^7)$, $C(R^8)$, $C(=NR^{15})$, O, S, or $C(=O)$;

$R^1$ and $R^2$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl, or alternatively $R^1$ and $R^2$, taken together with the atoms to which they are bonded, form an aryl, substituted aryl, cycloalkyl, substituted cycloalkyl, cycloheteroalkyl, substituted cycloheteroalkyl, heteroaryl or substituted heteroaryl ring;

D and E are independently O, $C(=O)$, $C(=S)$, $C(=NR^3)$ or $S(O)_2$;

$R^3$ is hydrogen, alkyl or substituted alkyl;

$R^4$ is hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, $—N=NR^9$, $—C(O)NR^9R^{10}$ or $—S(O)_2NR^9R^{10}$;

$R^5$ is hydrogen, amino, substituted amino, alkyl, substituted alkyl, acyl, substituted acyl, aryl, substituted aryl, arylalkyl, substituted arylalkyl, aryloxy, substituted aryloxy, heteroaryl, substituted heteroaryl, heteroarylalkyl, substituted heteroarylalkyl, heteroalkyl, substituted heteroalkyl, $—C(O)NR^{11}R^{12}$ or $—S(O)_2NR^{11}R^{12}$;

$R^6$, $R^7$ and $R^{15}$ are independently hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, $—C(O)NR^{13}R^{14}$ or $—S(O)_2NR^{13}R^{14}$;

$R^8$ is alkyldiyl, substituted alkyldiyl, heteroalkyldiyl or substituted heteroalkyldiyl; and $R^9$, $R^{10}$, $R^{11}$, $R^{12}$, $R^{13}$ and $R^{14}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^9$ and $R^{10}$, taken together with the atoms to which they are bonded, form a cycloheteroalkyl or substituted cycloheteroalkyl ring.

In one embodiment of Formula (I), D and E are $C(=O)$.

In one embodiment of Formula (I), A is N and B is $N(R^5)$.

In one embodiment of Formula (I), D and E are $C(=O)$, A is N and B is $N(R^5)$.

In one embodiment of Formula (I), $R^5$ is amino, substituted amino, alkyl, or substituted alkyl.

In specific embodiments of the present invention, a compound having structural Formula (I) is selected from the group consisting of:

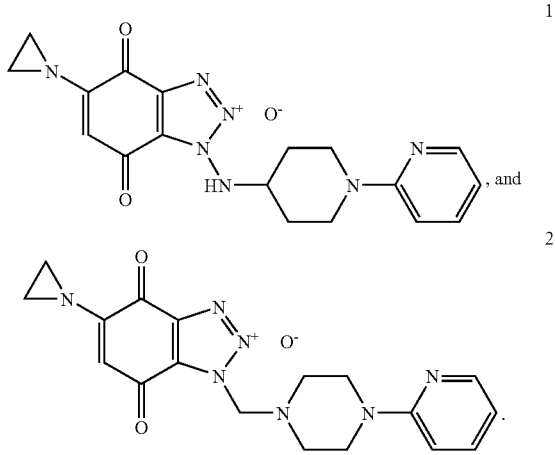

or a salt, solvate, or physiologically functional derivative thereof.

In one embodiment of Formula (I), $R^1$ and $R^2$, taken together with the atoms to which they are bonded, form an aryl, substituted aryl, cycloalkyl, substituted cycloalkyl, heteroaryl or substituted heteroaryl ring.

In one embodiment of Formula (I), $R^1$ and $R^2$, taken together with the atoms to which they are bonded, form a thienyl, substituted thienyl, furanyl, substituted furanyl, pyridinyl, substituted pyridinyl, pyrimidinyl, substituted pyrimidinyl, oxazolyl, substituted oxazolyl, phenyl or substituted phenyl ring.

In one embodiment of Formula (I), $R^1$ and $R^2$, taken together with the atoms to which they are bonded, form a phenyl or substituted phenyl ring.

In a specific embodiment of the present invention, a compound having structural Formula (I) contains the following structure:

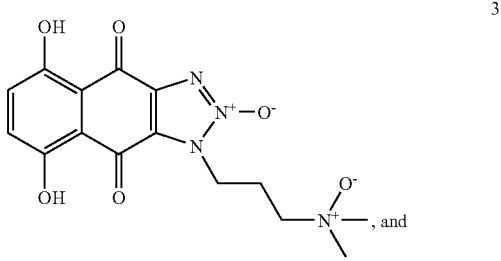

4

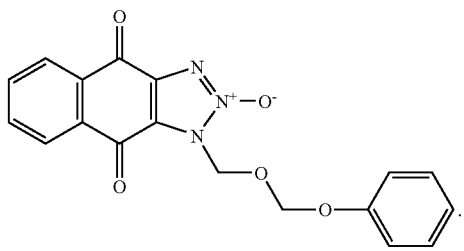

or a salt, solvate, or physiologically functional derivative thereof.

In one embodiment of Formula (I), A is CR⁴ and B is NR⁵.

In one embodiment of Formula (I), D and E are C(=O), A is CR⁴ and B is NR⁵.

In specific embodiments of the present invention, a compound having structural Formula (I) is selected from the group consisting of:

5

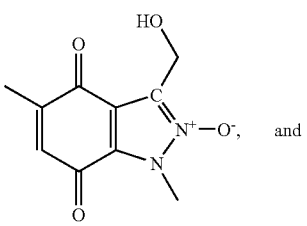

and

6

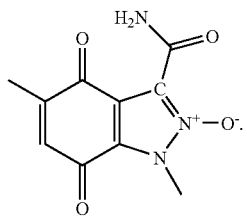

or a salt, solvate, or physiologically functional derivative thereof.

In one embodiment of Formula (I), the compounds have structural Formula (II):

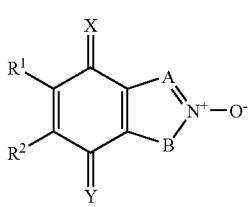

(II)

or a salt, solvate, or physiologically functional derivative thereof;

wherein: X and Y are independently O, S, or NR¹⁶; and R¹⁶ is hydrogen, alkyl or substituted alkyl.

In one embodiment of Formula (II), the compounds have structural Formula (III):

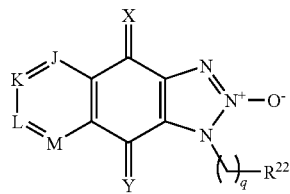

(III)

or a salt, solvate, or physiologically functional derivative thereof;

wherein: q is 0, 1, 2, 3, 4 or 5;

X and Y are independently O, S, or NR²¹;

J, K, L and M are independently CR²⁵ or N.

R²¹ is hydrogen, alkyl or substituted alkyl;

R²² is halo, hydrogen, alkyl, substituted alkyl, cycloheteroalkyl, substituted cycloheteroalkyl, —OC(O)R²³, —NR²³R²⁴, —N(R²³)C(O)R²⁴, heteroalkyl, substituted heteroalkyl, aryl, substituted aryl, —C(O)NR²³R²⁴, —S(O)₂NR²³R²⁴, heteroaryloxy or substituted heteroaryloxy;

R²³ and R²⁴ are independently hydrogen, alkyl, substituted alkyl, cycloheteroalkyl, substituted cycloheteroalkyl, heteroalkyl, substituted heteroalkyl, aryl, substituted aryl, arylalkyl, substituted arylalkyl, heteroaryl, substituted heteroaryl, heteroarylalkyl, or substituted heteroarylalkyl, or alternatively, R²³ and R²⁴, taken together with the atoms to which they are bonded, form a cycloheteroalkyl or substituted cycloheteroalkyl ring;

R²⁵ is halo, cyano, nitro, OR²⁶, S(O)ₜR²⁶, CO₂R²⁶, CONR²⁶R²⁷ or NR²⁶R²⁷, alkyl, substituted alkyl, heteroalkyl or substituted heteroalkyl, wherein t is 0, 1, or 2; and Each R²⁶ and R²⁷ are independently hydrogen, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R²⁶ and R²⁷, taken together with the atoms to which they are bonded, form a cycloheteroalkyl or substituted cycloheteroalkyl ring.

In one embodiment of Formula (III), q is 0, X and Y are O, and R²² is amino, substituted amino, heteroaryloxy, or substituted heteroaryloxy.

In specific embodiments of Formula (III) wherein q is 0, the compound has a structure selected from the group consisting of:

7

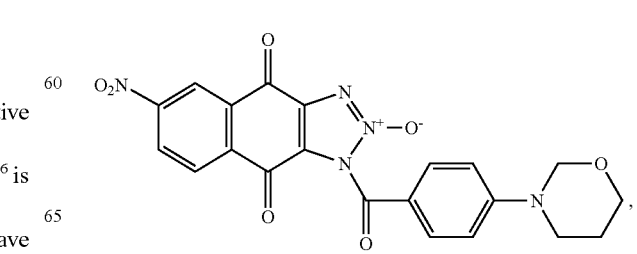

-continued

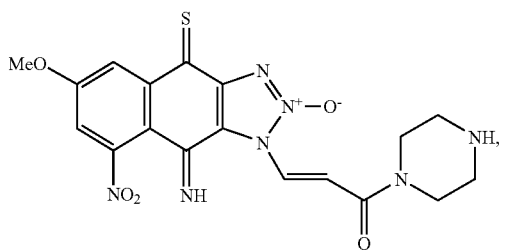

8

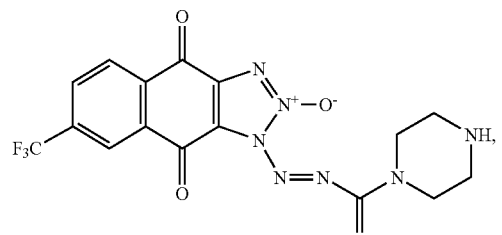

9

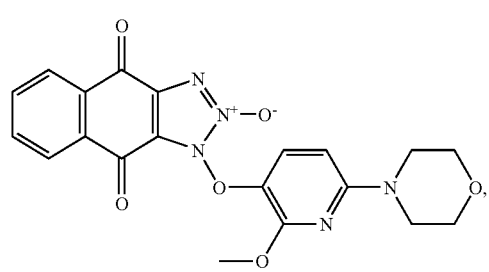

10

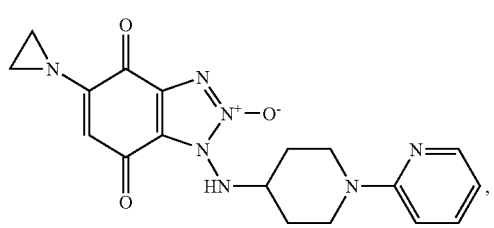

11

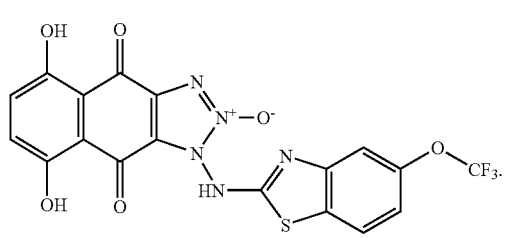

13 or a salt, solvate, or physiologically functional derivative thereof.

In one embodiment of Formula (III), q is 1, X and Y are (O) and $R^{22}$ is hydrogen, amino, substituted amino, heteroalkyl, substituted heteroalkyl, aryl, substituted aryl, cycloheteroalkyl or substituted cycloheteroalkyl.

In one embodiment of Formula (III) wherein q is 1, $R^{22}$ is phenyl or substituted phenyl. In specific examples, the substituted phenyl comprises one or more substituents selected from the group consisting of cycloheteroalkyl, substituted cycloheteroalkyl, heteroaryl, substituted heteroaryl, phenyl, and substituted phenyl.

In one embodiment of Formula (III) wherein q is 1, $R^{22}$ is

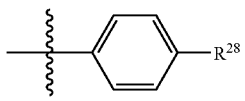

wherein $R^{28}$ is cycloheteroalkyl, substituted cycloheteroalkyl, heteroaryl, substituted heteroaryl, phenyl or substituted phenyl.

In one embodiment of Formula (III) wherein q is 1, $R^{22}$ is amino or substituted amino.

In specific embodiments of Formula (III) wherein q is 1, the compound has a structure selected from the group consisting of:

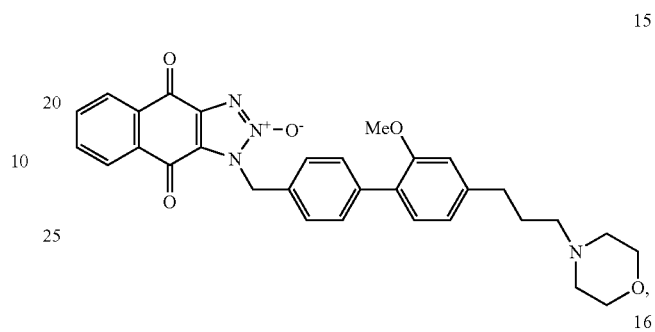

15

16

17

18

19

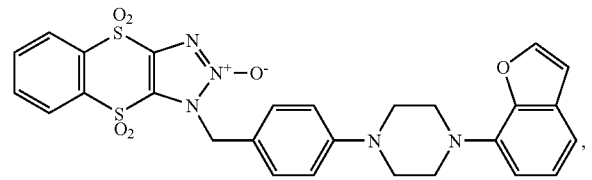

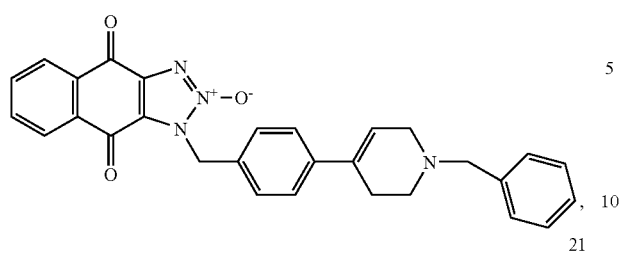

20

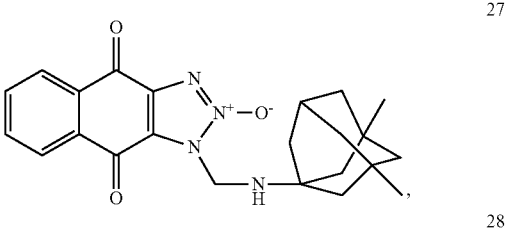

27

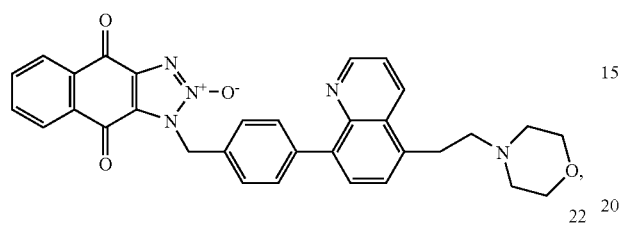

21

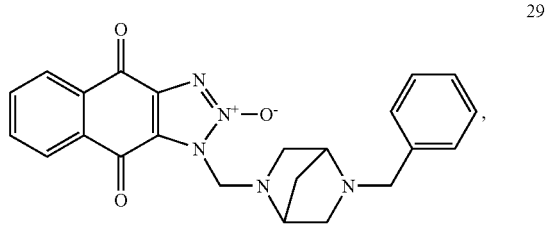

28

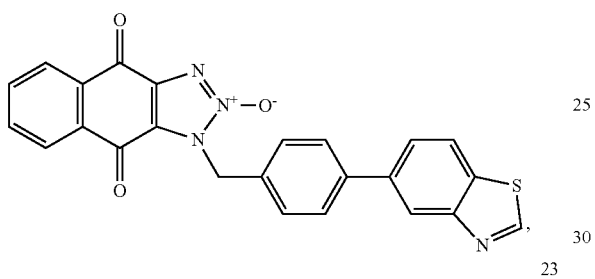

22

29

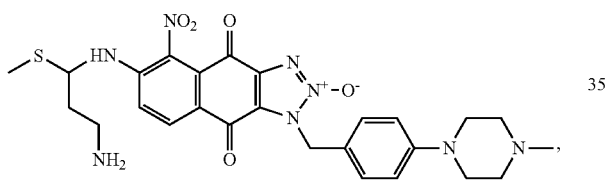

23

30

24

31

25

32

26 or a salt, solvate, or physiologically functional derivative thereof.

In one embodiment of Formula (III), q is 2 and $R^{22}$ is amino, substituted amino, alkyl, substituted alkyl, aryl, substituted aryl, cycloheteroalkyl substituted cycloheteroalkyl —OC(O)$R^{23}$ or —C(O)NR$^{23}$R$^{24}$.

In one embodiment of Formula (III) wherein q is 2, $R^{22}$ is phenyl or substituted phenyl. In specific examples, the substituted phenyl comprises one or more substituents selected

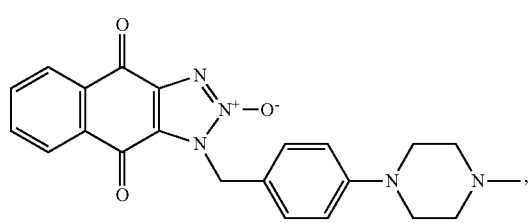

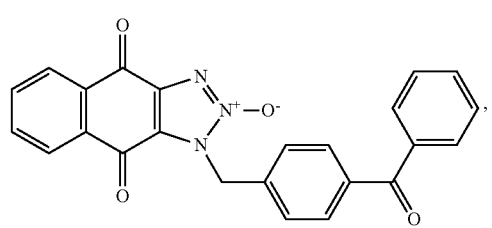

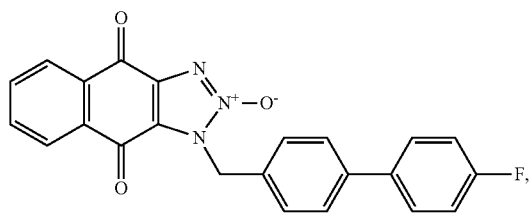

from the group consisting of phenyl, substituted phenyl, heteroaryl, substituted heteroaryl, cycloalkyl, substituted cycloalkyl, cycloheteroalkyl, and substituted cycloheteroalkyl.

In one embodiment of Formula (III) wherein q is 2, $R^{22}$ is $C(O)NR^{23}R^{24}$ and $R^{23}$ and $R^{24}$, taken together with the atoms to which they are bonded, form a cycloheteroalkyl or substituted cycloheteroalkyl ring. In specific examples, the substituted cycloheteroalkyl comprises one or more substituents selected from the group consisting of phenyl, substituted phenyl, heteroaryl, substituted heteroaryl, cycloalkyl, substituted cycloalkyl, cycloheteroalkyl, and substituted cycloheteroalkyl.

In specific embodiments of Formula (III) wherein q is 2, the compound has a structure selected from the group consisting of:

41

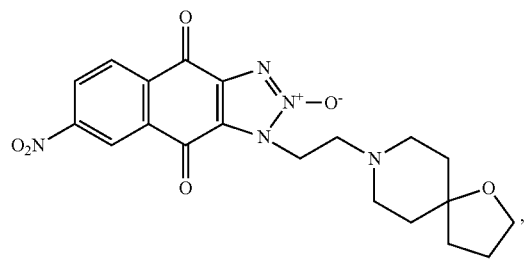

43

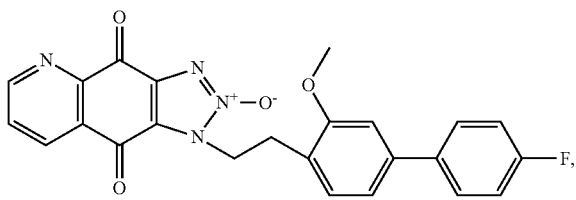

45

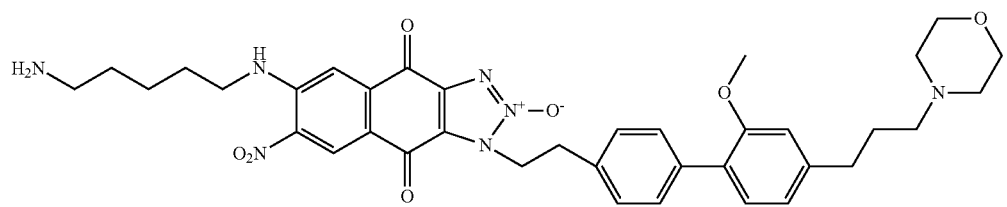

47

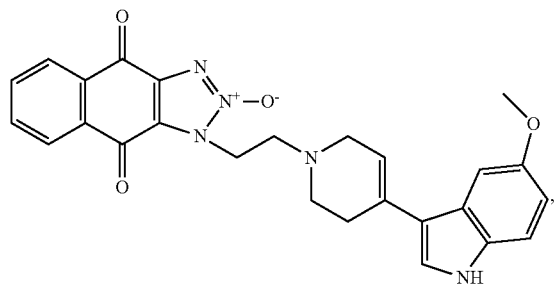

49

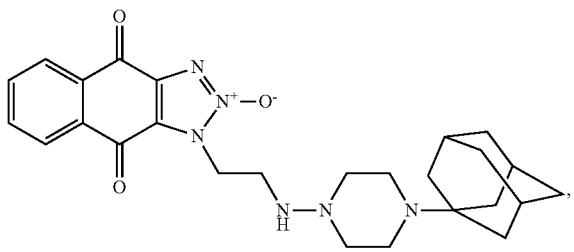

51

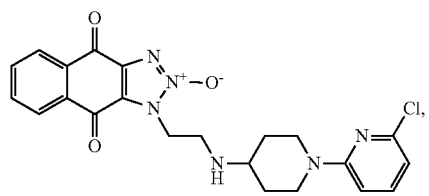

53

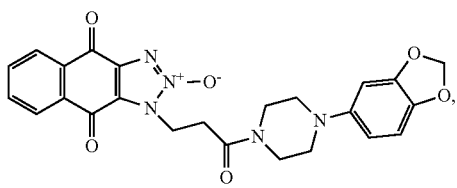

55

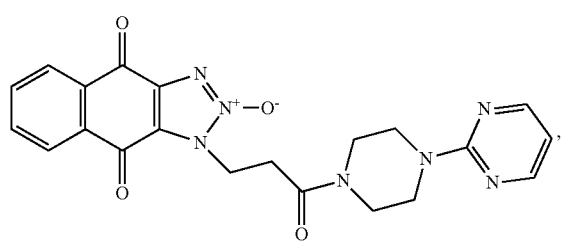

57

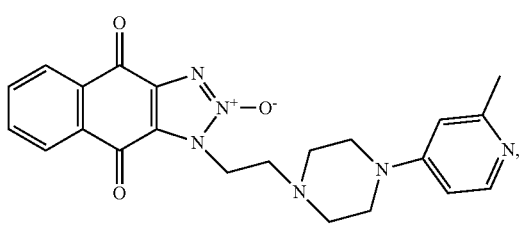

-continued
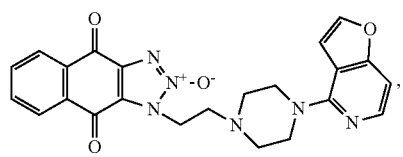
59
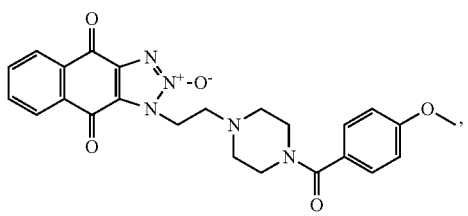
61
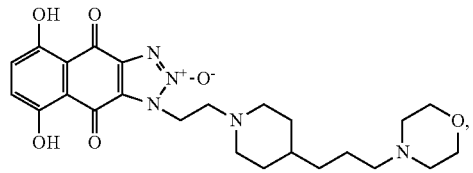
63
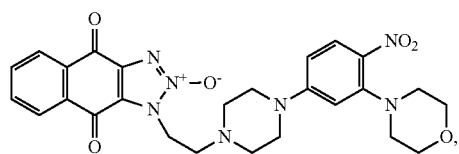
67
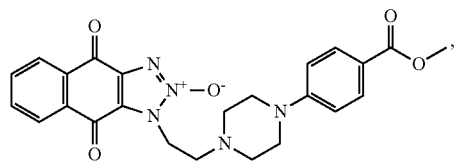
71
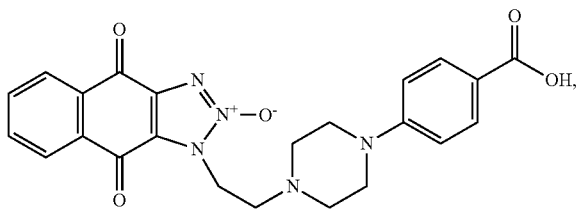
65
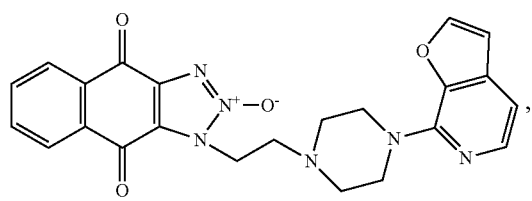
75
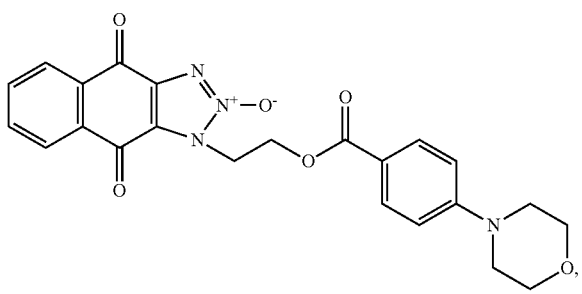
69
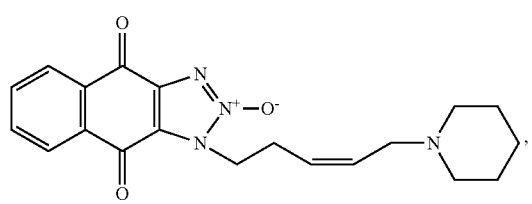
73
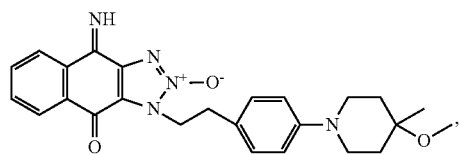
81
77
79
83

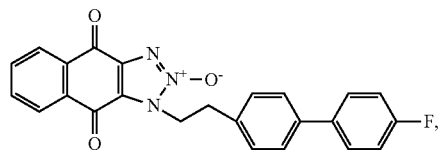

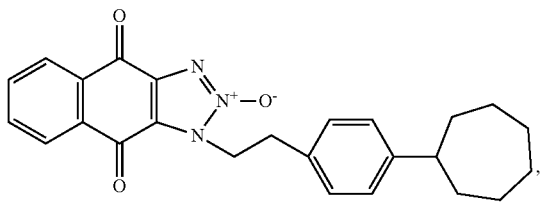

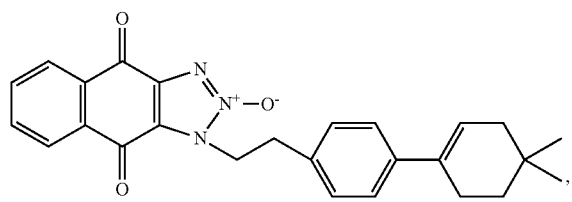

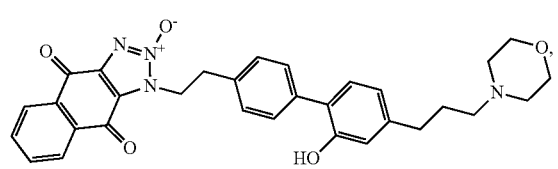

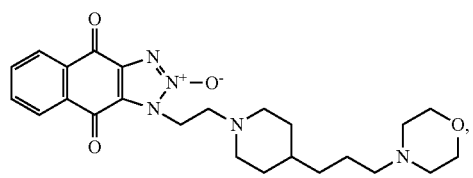

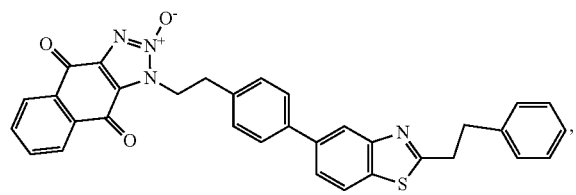

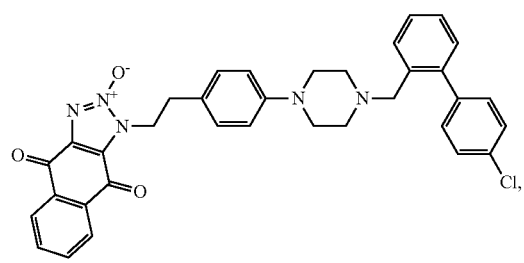

or a salt, solvate, or physiologically functional derivative thereof.

In one embodiment of Formula (III), q is 3 and $R^{22}$ is —OC(O)$R^{23}$, —N$R^{23}R^{24}$, aryl, substituted aryl, heteroaryl, substituted heteroaryl, cycloheteroalkyl or substituted cycloheteroalkyl.

In one embodiment of Formula (III) wherein q is 3, $R^{22}$ is substituted cycloheteroalkyl which comprises substituents selected from the group consisting of aryl, substituted aryl, alkyl, substituted alkyl, arylalkyl, substituted arylalkyl, cycloalkyldiyl, substituted cycloalkydiyl, cycloheteroalkyldiyl, substituted cycloheteroalkydiyl, and hydroxyl.

In specific embodiments of Formula (III) wherein q is 3, the compound has a structure selected from the group consisting of:
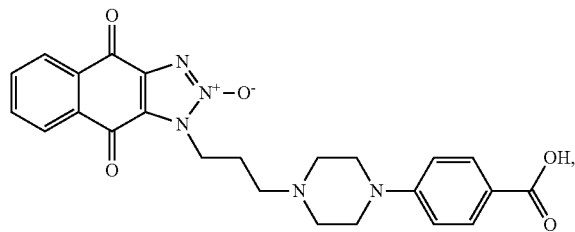
101
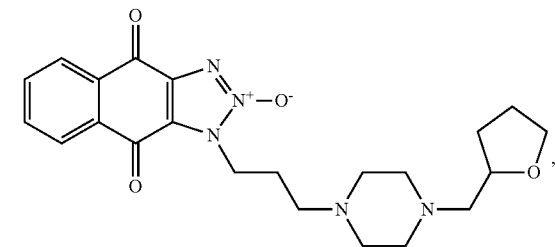
103
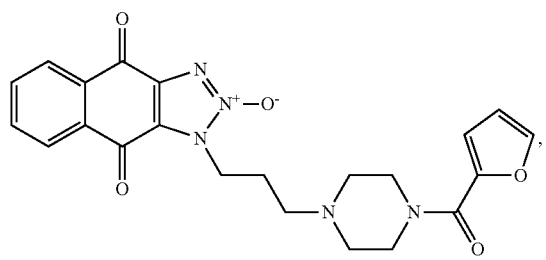
105
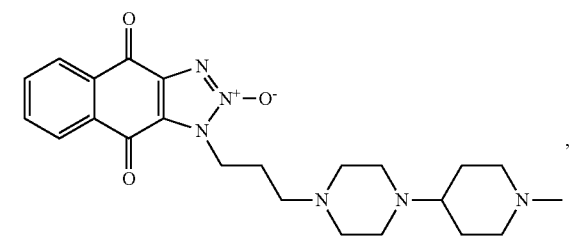
107
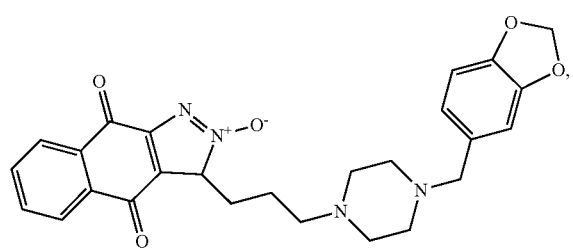
109
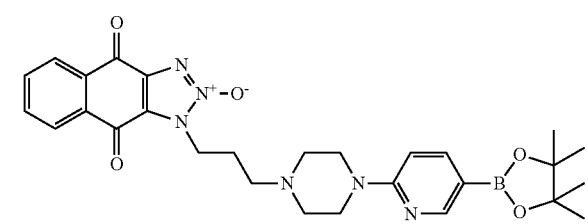
111
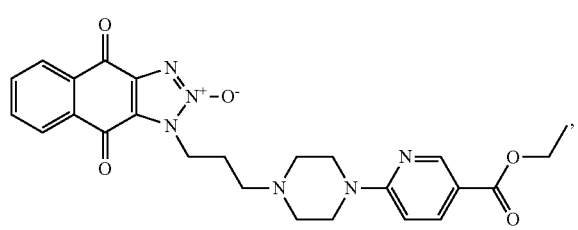
113
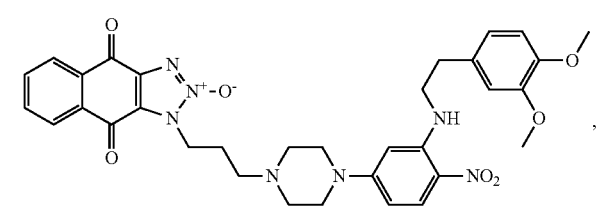
115
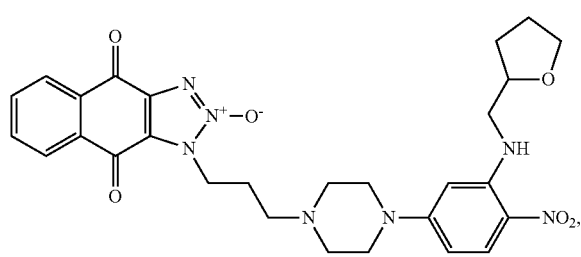
117
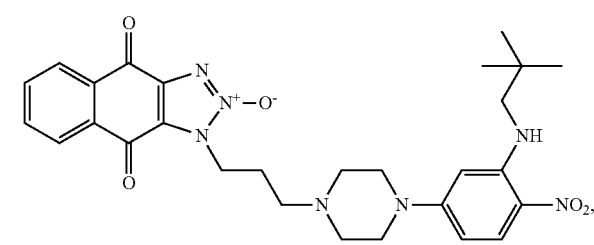
119

121
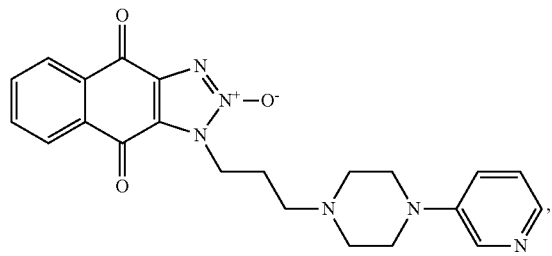
123
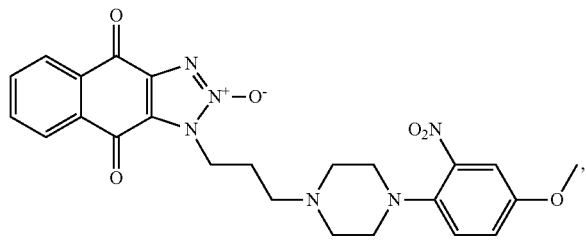
125
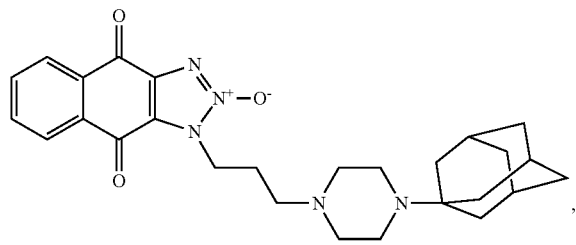
127
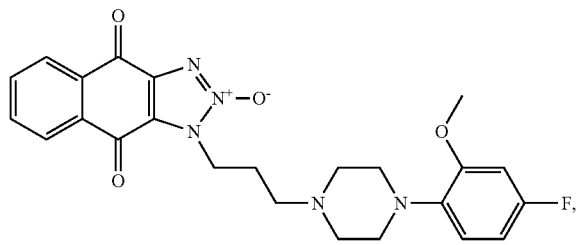
129
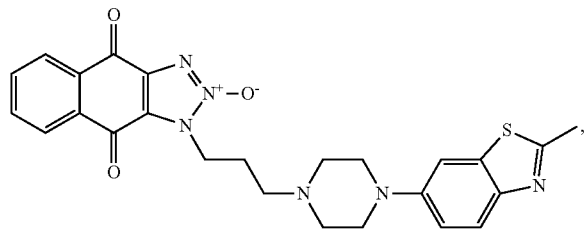
131
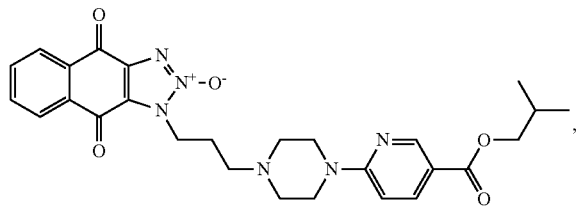
133
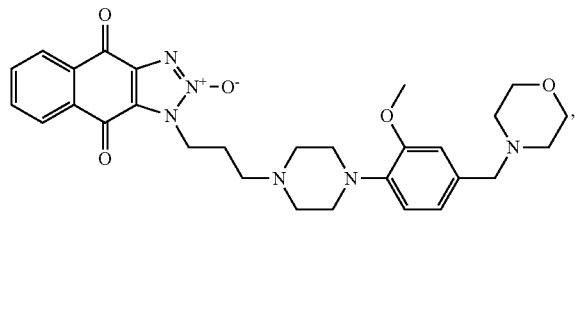
135
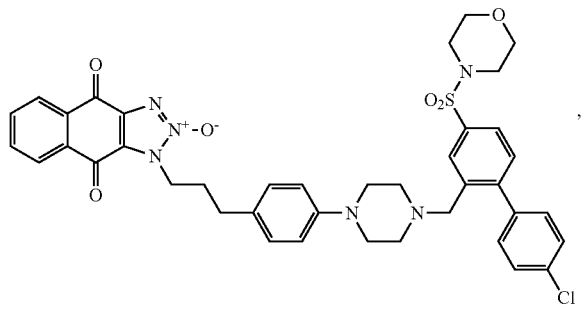
137
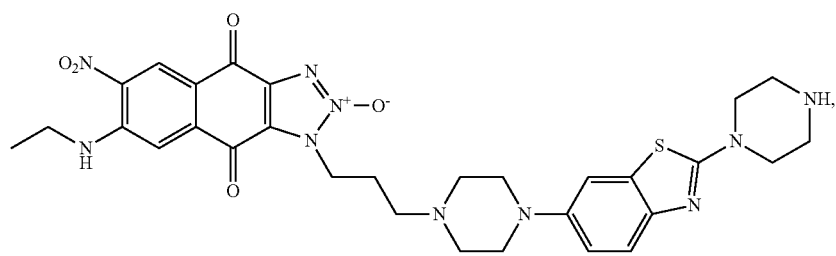

-continued
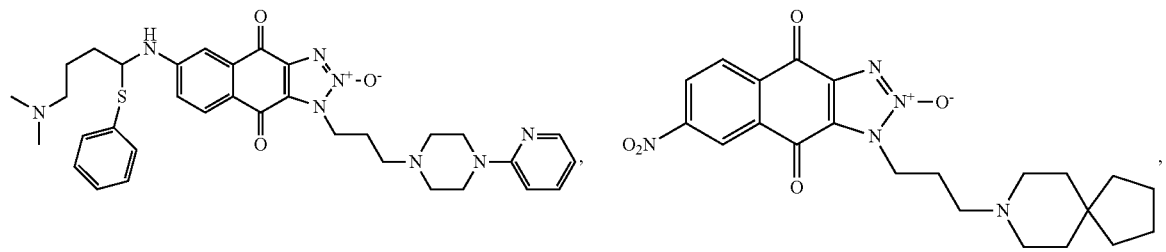
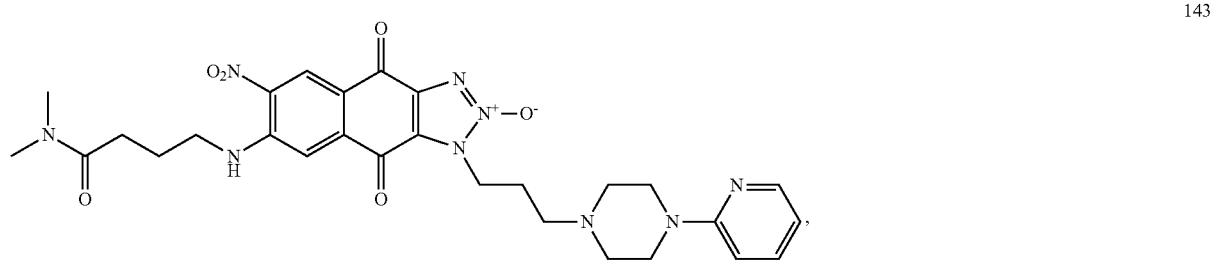
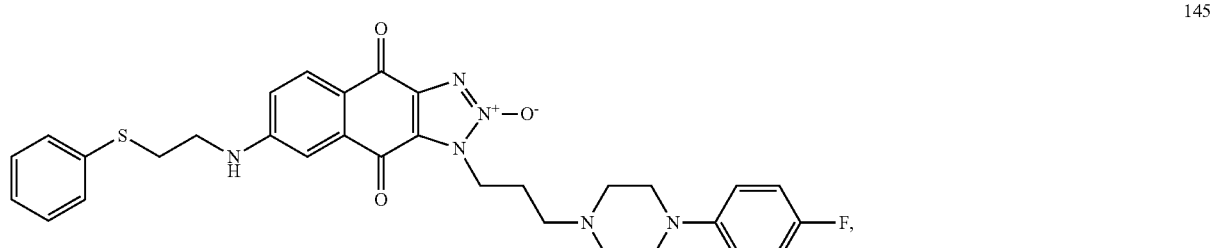
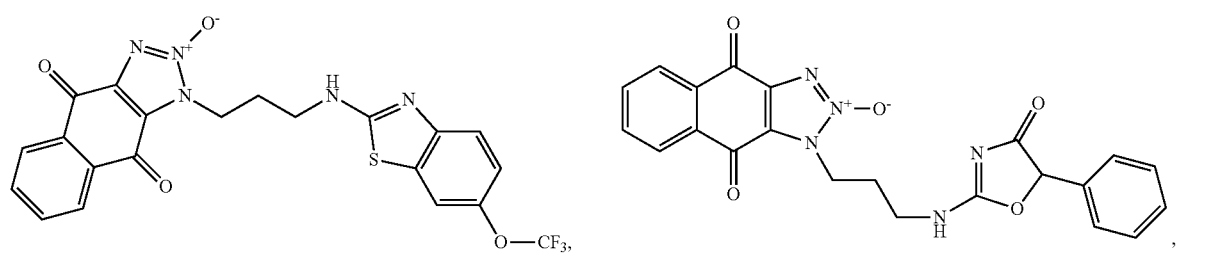
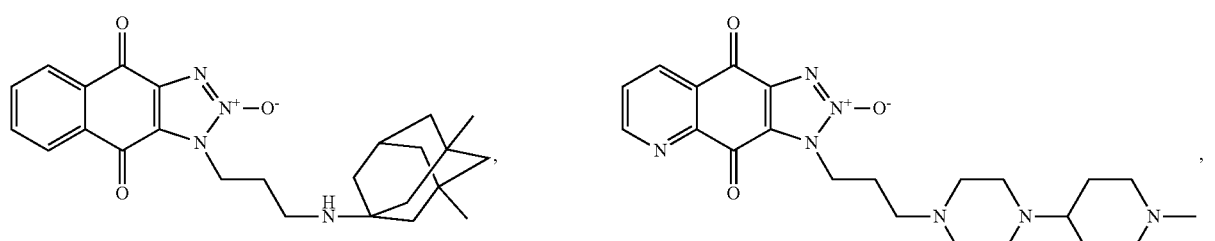
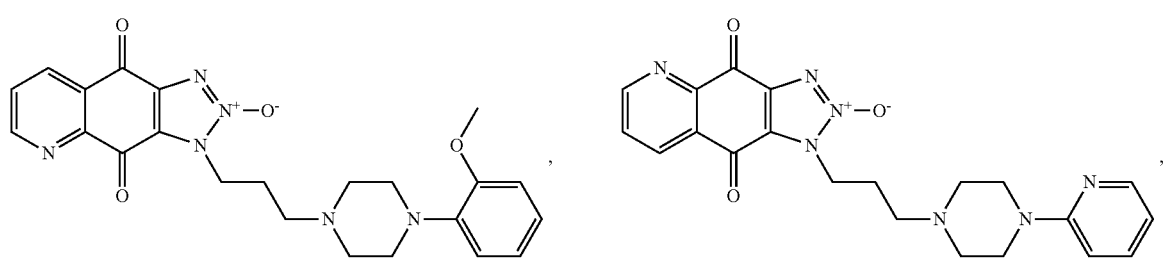

-continued
161
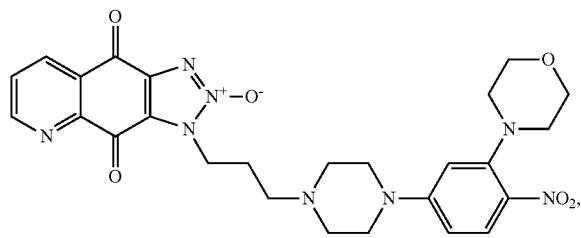
161
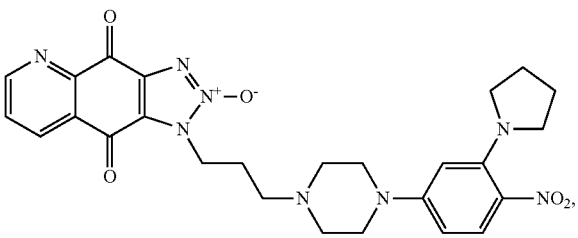
163
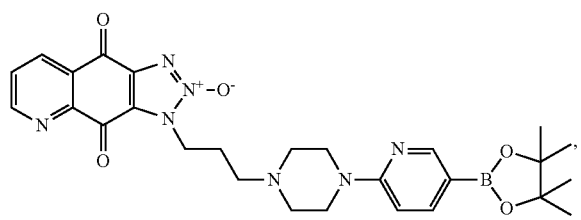
165
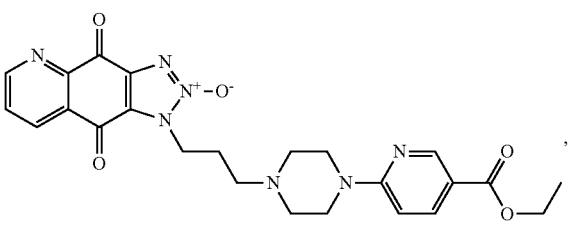
167
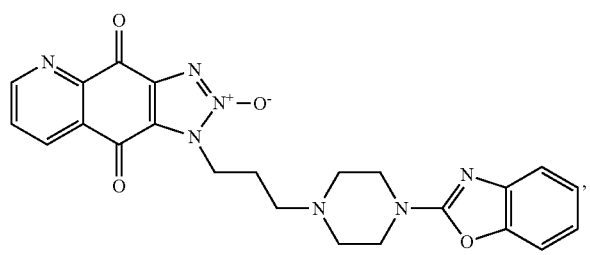
169
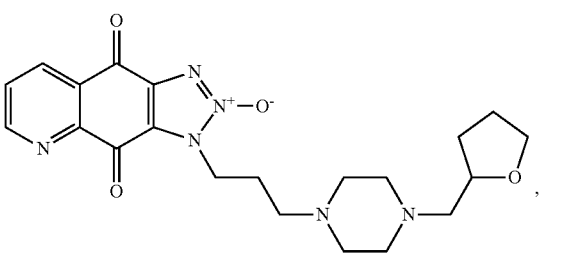
171
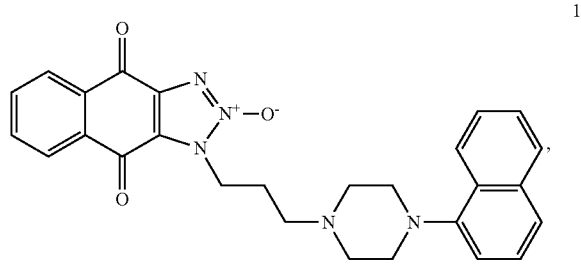
173
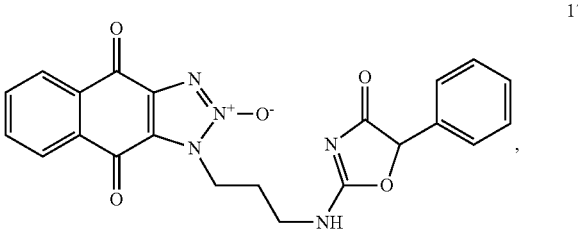
175
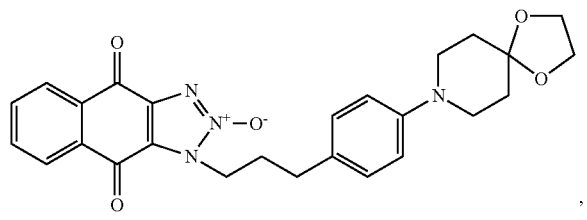
177
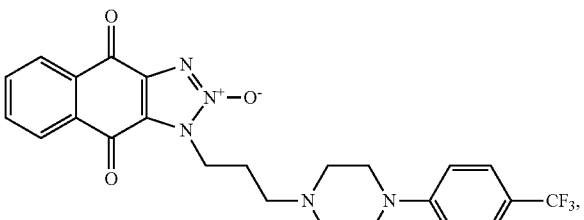
179
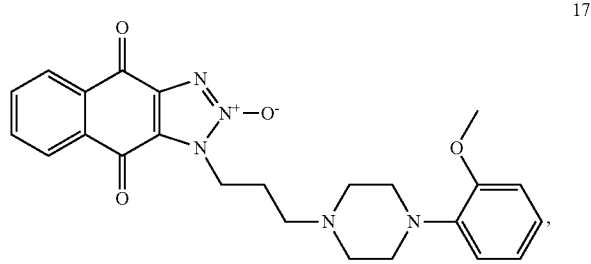
181
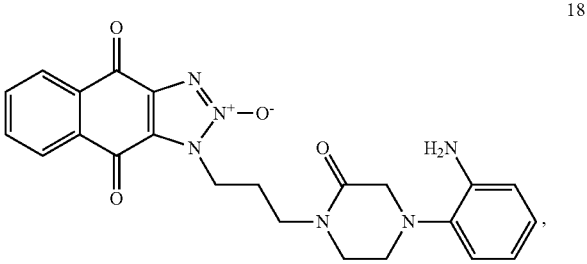

-continued
183
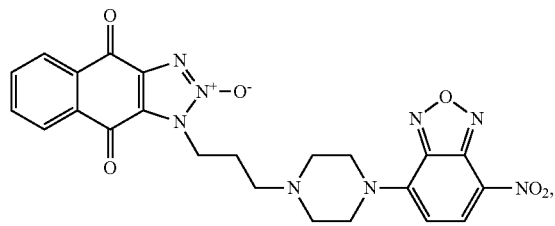
185
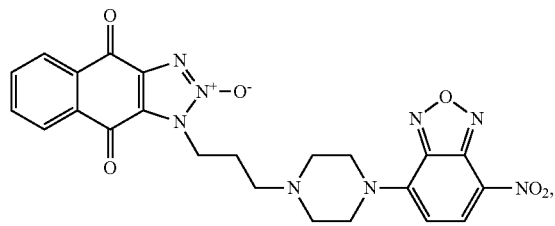
187
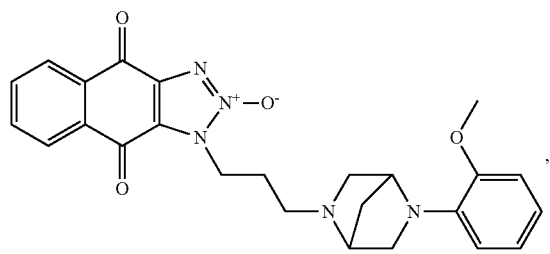
189
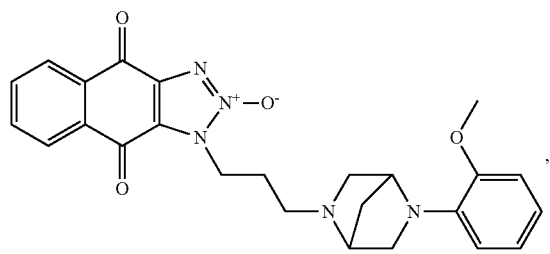
191
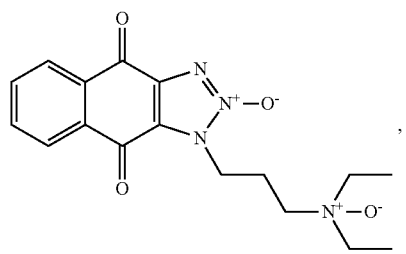
193
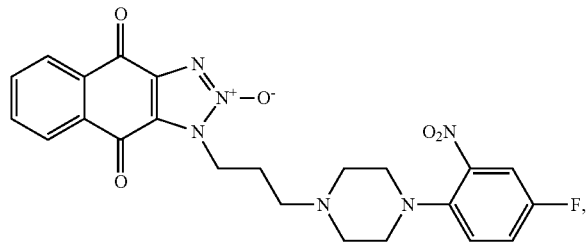
195
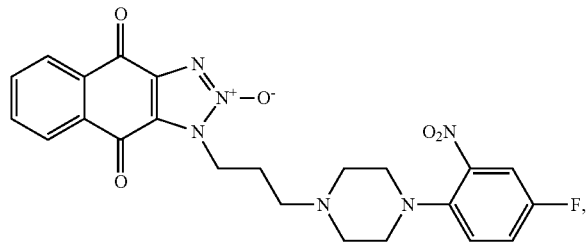
197
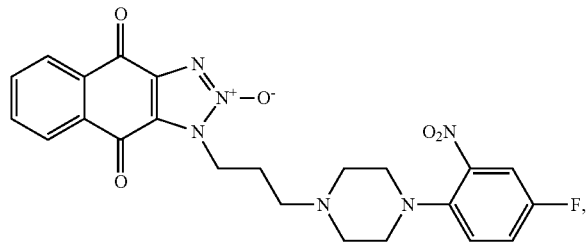
199
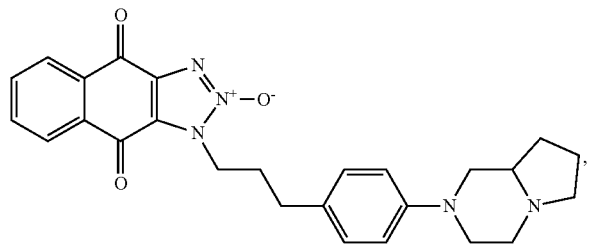
201
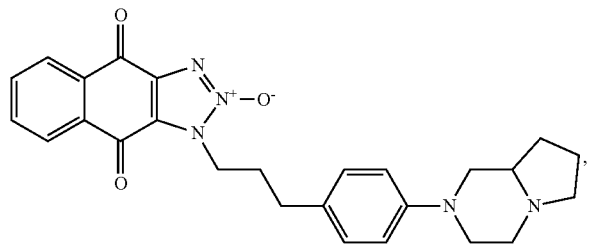
203
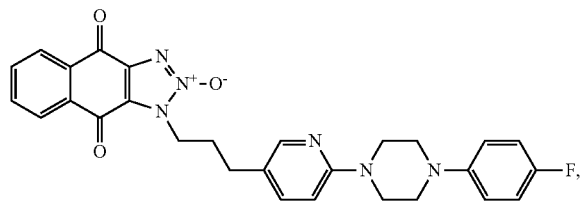
205
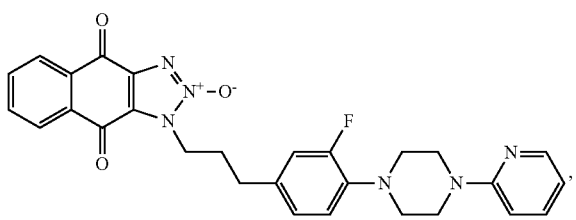

-continued
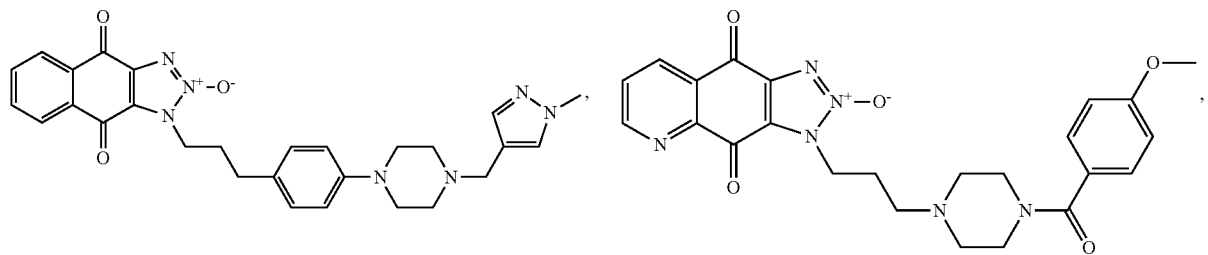
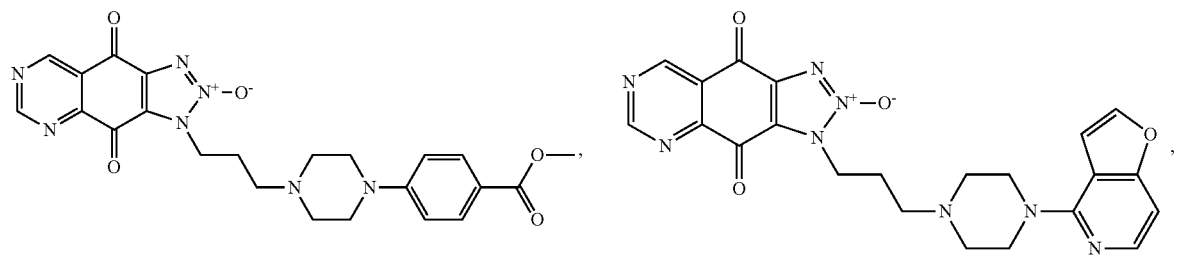
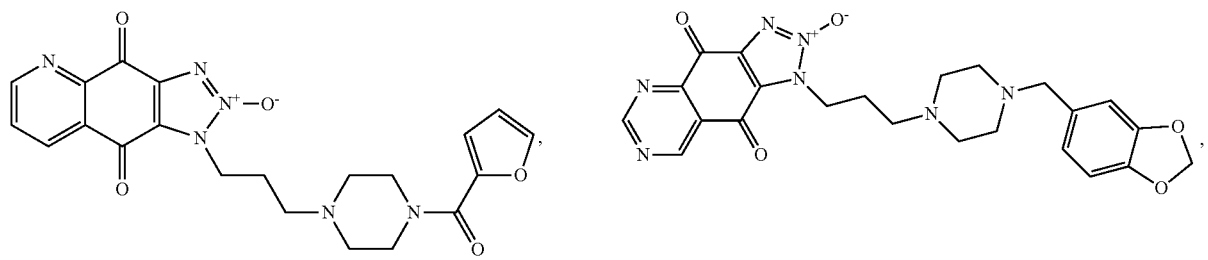
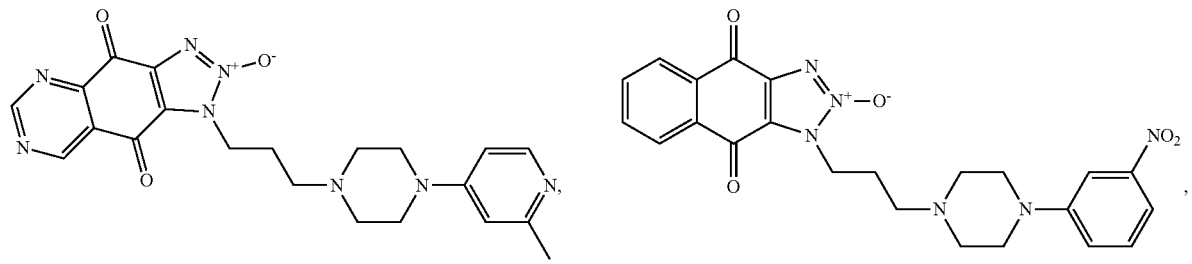
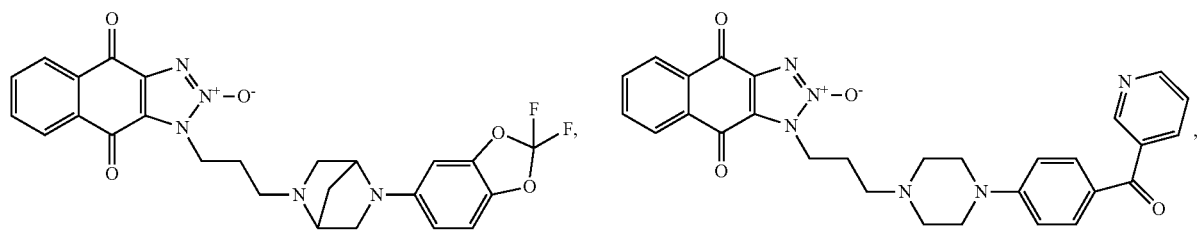

-continued
227
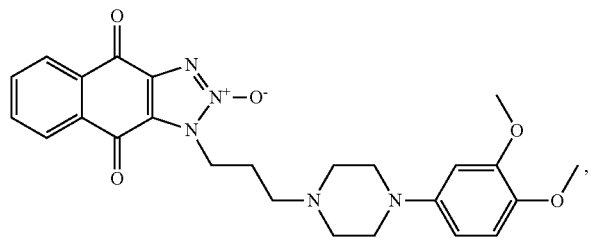
229
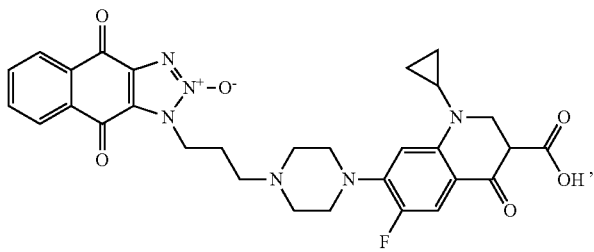
231
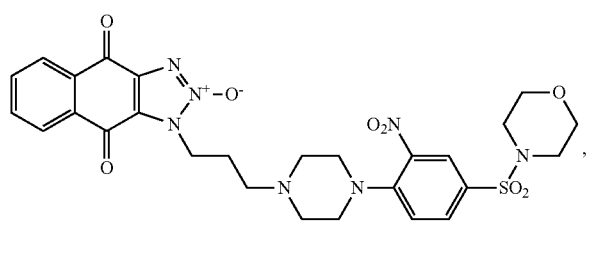
233
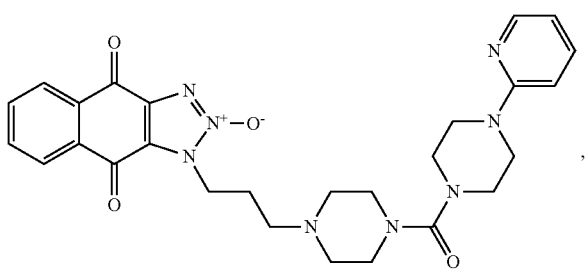
235
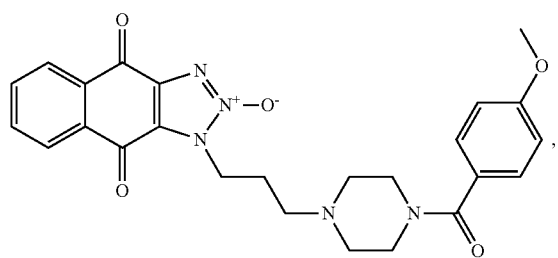
237
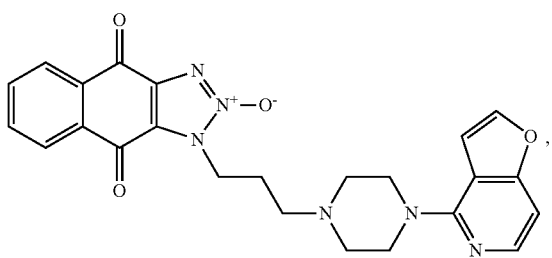
239
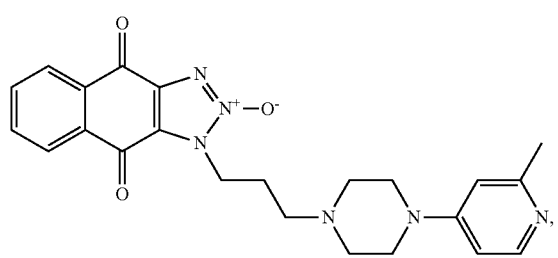
241
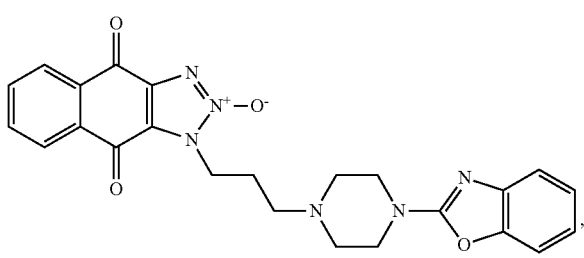
243
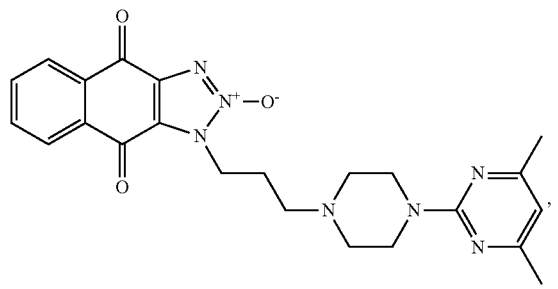
245
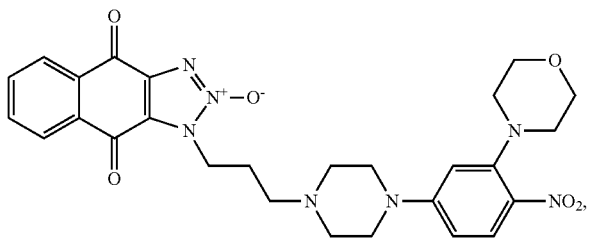

-continued
247 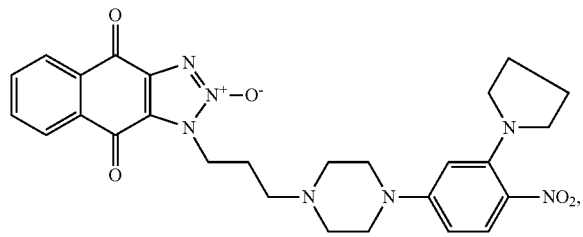
249 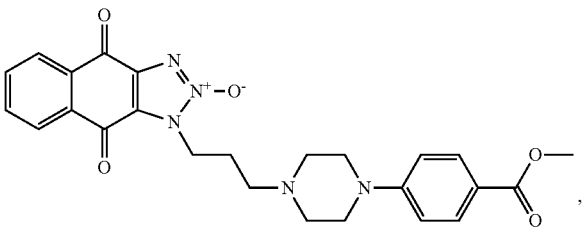
251 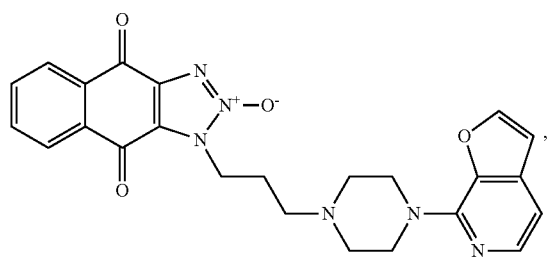
253 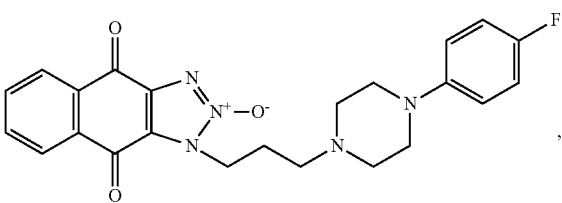
255 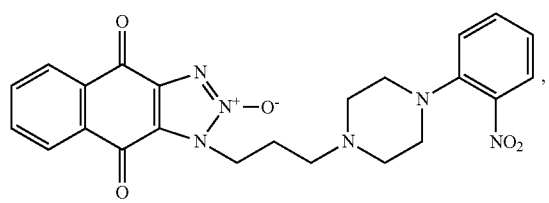
257 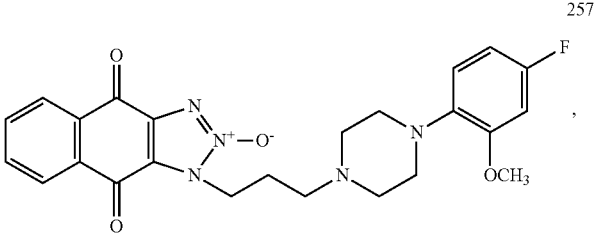
259 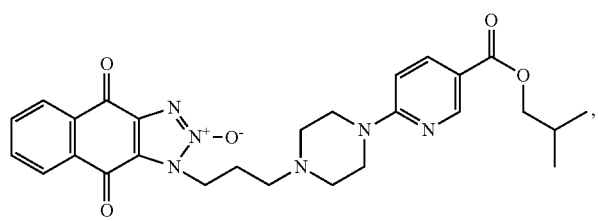
261 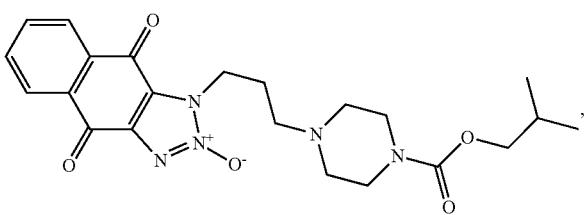
263 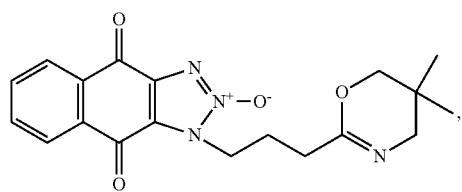
265 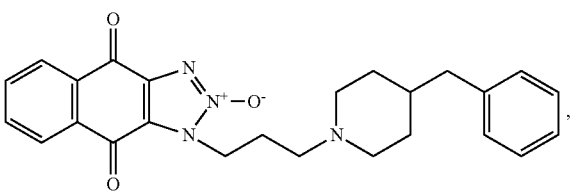
267 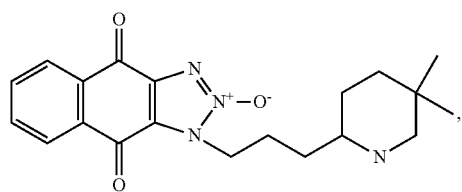
269 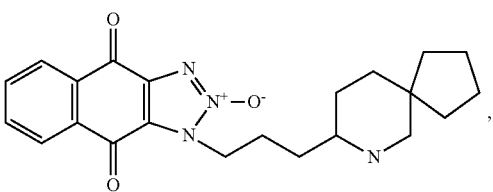

-continued
271
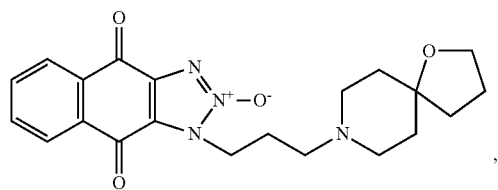
273
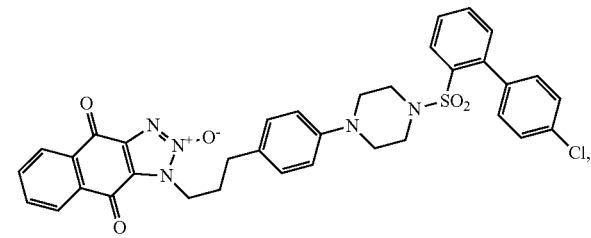
275
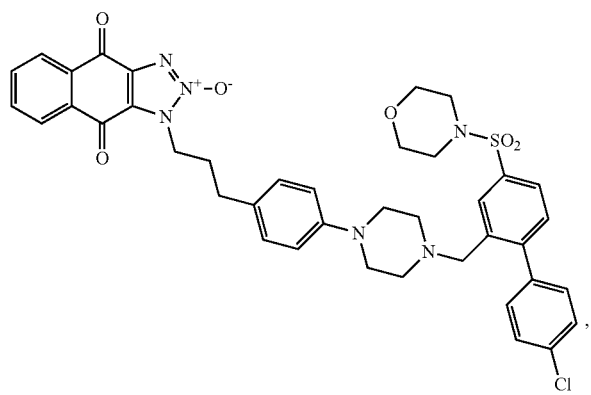
277
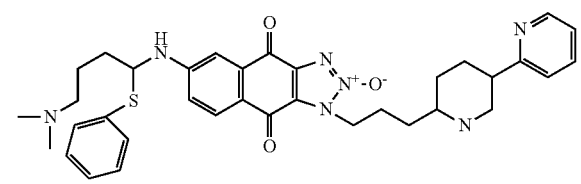
279
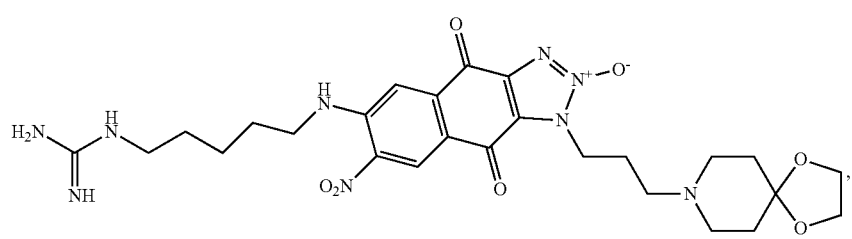
281
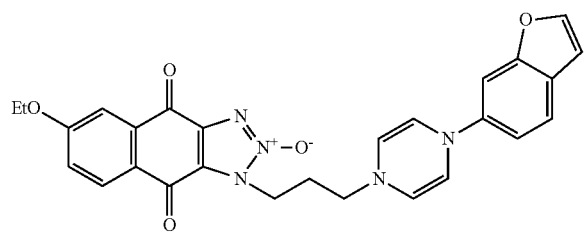
283
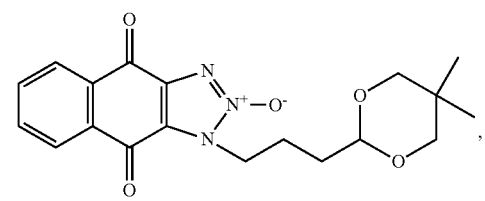
285
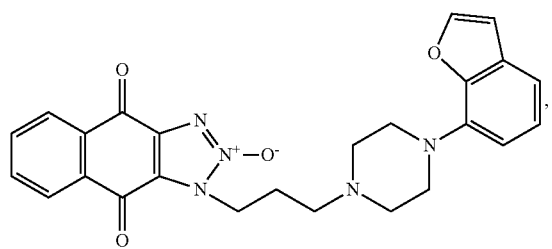
287
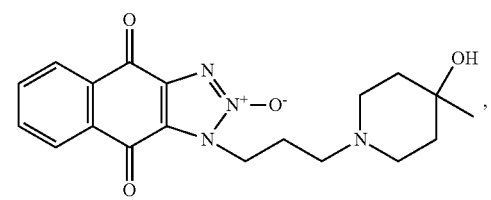

-continued

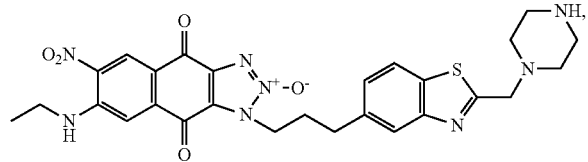
289

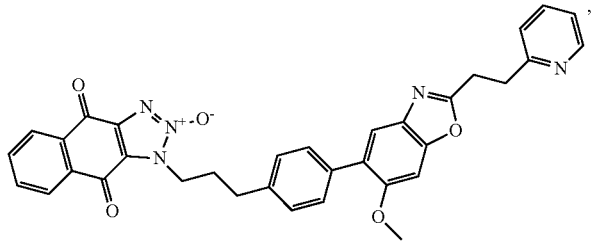
291

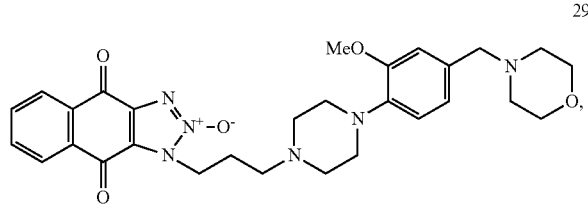
293

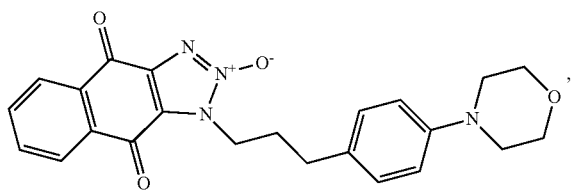
295

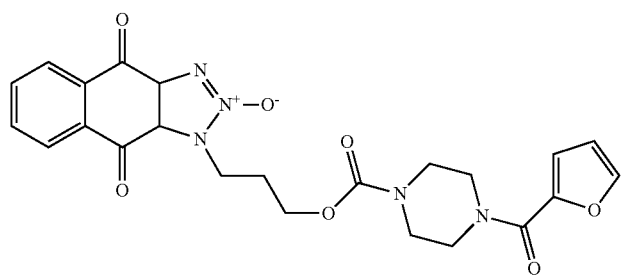
297 or a salt, solvate, or physiologically functional derivative thereof.

In one embodiment of Formula (II), the compounds have structural Formula (IV):

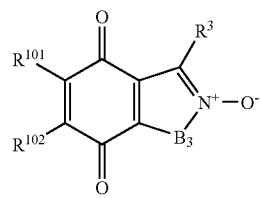

(IV)

or a salt, solvate, or physiologically functional derivative thereof;

wherein: $B_3$ is $N(R^4)$, O, or C(O); and $R^{101}$ and $R^{102}$ together with the atoms to which they are bonded, form an aryl, substituted aryl, heteroaryl or substituted heteroaryl ring.

In one embodiment of Formula (IV), $R^{101}$ and $R^{102}$ together with the atoms to which they are bonded form a phenyl or substituted phenyl ring.

In specific embodiments of Formula (IV), the compound has a structure selected from the group consisting of:

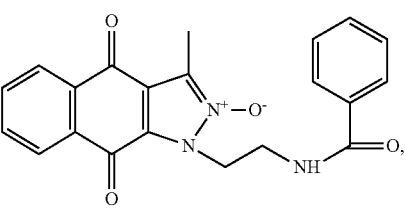
301

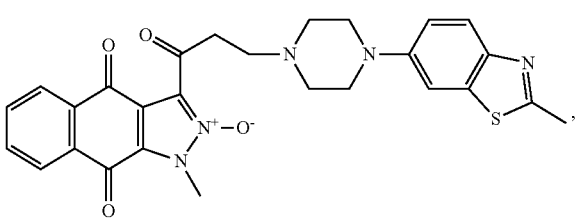
303

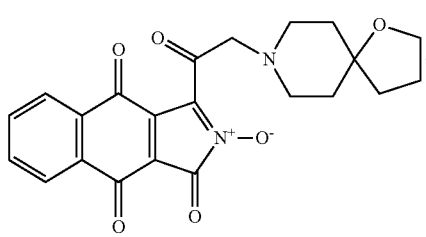
305

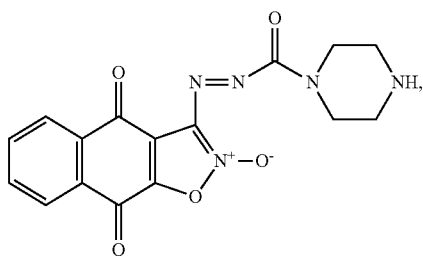

307 or a salt, solvate, or physiologically functional derivative thereof.

In one embodiment of Formula (II), the compounds have structural Formula (V):

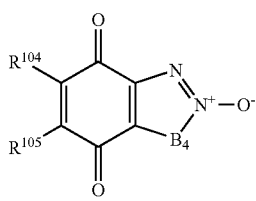

(V)

or a salt, solvate, or physiologically functional derivative thereof;

wherein: $B_4$ is $C(R^5R^6)$ or $C(R^7)$; and $R^{104}$ and $R^{105}$ together with the atoms to which they are bonded form an aryl, substituted aryl, heteroaryl or substituted heteroaryl ring.

In one embodiment of Formula (V), $R^{104}$ and $R^{105}$ together with the atoms to which they are bonded form an aryl, heteroaryl or furanyl ring.

In one embodiment of Formula (V), $R^7$ is substituted alkyldiyl, or substituted heteroalkyldiyl.

In specific embodiments of Formula (V), the compound has a structure selected from the group consisting of:

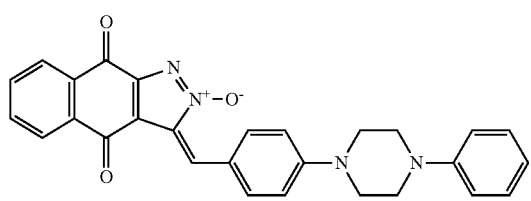

309

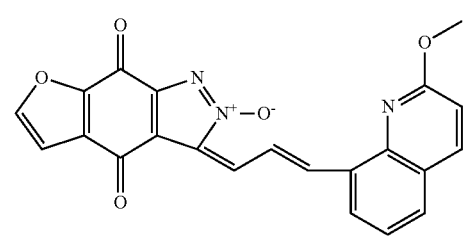

311

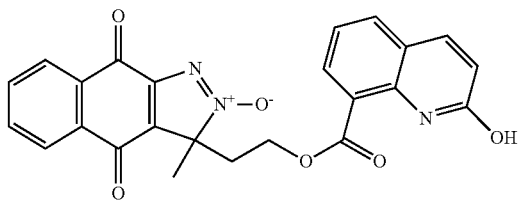

313

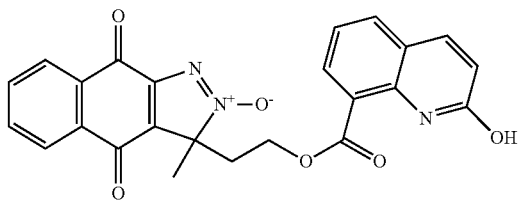

315 or a salt, solvate, or physiologically functional derivative thereof.

In one embodiment of Formula (II), the compounds have structural Formula (VI):

(VI)

wherein: m is 1, 2, 3, 4 or 5;

$R^{106}$ and $R^{107}$ together with the atoms to which they are bonded, form a cycloalkyl, substituted cycloalkyl, heteroaryl or substituted heteroaryl ring;

$R^{108}$ is aryl, substituted aryl, cycloheteroalkyl, substituted cycloheteroalkyl or —$CONR^{109}R^{110}$; and $R^{109}$ and $R^{110}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{109}$ and $R^{110}$ taken together with the atoms to which they are bonded, form a cycloheteroalkyl or substituted cycloheteroalkyl ring.

In one embodiment of Formula (VI), $R^{106}$ and $R^{107}$ together with the atoms to which they are bonded, form an aryl, heteroaryl, substituted heteroaryl, thienyl or furanyl ring.

In one embodiment of Formula (VI), D and E are C(=O).

In specific embodiments of Formula (VI), the compound has a structure selected from the group consisting of:

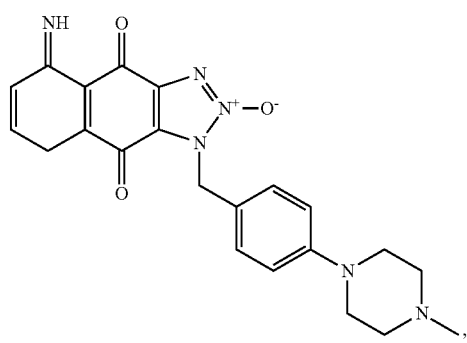

317

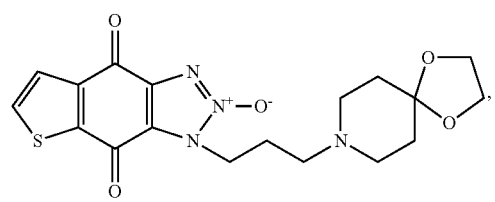

319

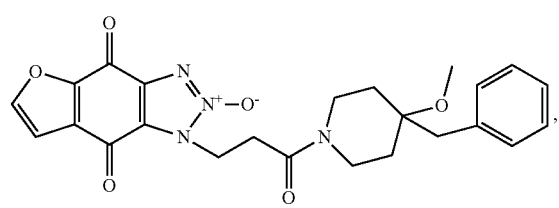

321

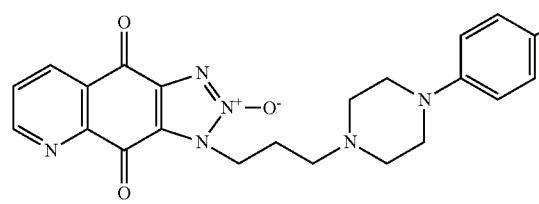

323

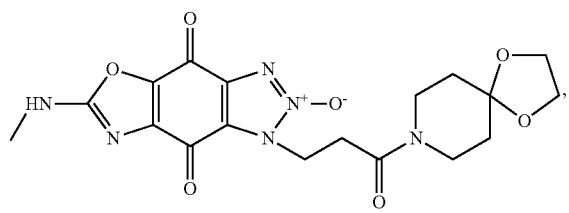

325

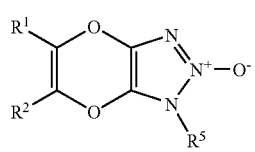

327

329

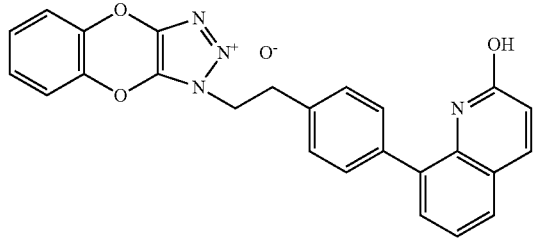

331 or a salt, solvate, or physiologically functional derivative thereof.

In one embodiment of Formula (I), the compounds have structural Formula (VII):

$$\text{(VII)}$$

or a salt, solvate, or physiologically functional derivative thereof;

In specific embodiments of Formula (VII), the compound has the structure:

335

In another aspect, the present invention provides a compound having of structural Formula (VIII):

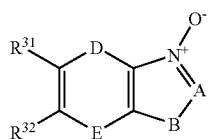

(VIII)

or a salt, solvate, or physiologically functional derivative thereof;

wherein: A is N, N$^+$—O$^-$, or C(R$^{33}$); B is N(R$^{34}$), C(R$^{35}$R$^{36}$), C(R$^{37}$), C(=NR$^{44}$), O, S, or C(O);

R$^{31}$ and R$^{32}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; or alternatively, R$^{31}$ and R$^{32}$, taken together with the atoms to which they are bonded, form a aryl, substituted aryl, cycloalkyl, substituted cycloalkyl, cycloheteroalkyl, substituted cycloheteroalkyl, heteroaryl or substituted heteroaryl ring;

D and E are independently O, C(=O), C(=S), C(=NR$^{45}$) or S(O)$_2$;

R$^{33}$ is halo, hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —N=NR$^{38}$, —C(O)NR$^{38}$R$^{39}$ or —S(O)$_2$NR$^{38}$R$^{39}$;

R$^{34}$ is hydrogen, alkyl, substituted alkyl, acyl, substituted acyl, aryl, substituted aryl, arylalkyl, substituted arylalkyl, aryloxy, substituted aryloxy, heteroaryl, substituted heteroaryl, heteroarylalkyl, substituted heteroarylalkyl, heteroalkyl, substituted heteroalkyl, or —C(O)NR$^{40}$R$^{41}$ or —S(O)$_2$NR$^{40}$R$^{41}$;

R$^{35}$, R$^{36}$ and R$^{44}$ are independently halo, hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —C(O)NR$^{42}$R$^{43}$ or —S(O)$_2$NR$^{42}$R$^{43}$;

R$^{37}$ is alkyldiyl, substituted alkyldiyl, heteroalkyldiyl or substituted heteroalkyldiyl;

R$^{38}$, R$^{39}$, R$^{40}$, R$^{41}$, R$^{42}$ and R$^{43}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{38}$ and R$^{39}$, taken together with the atoms to which they are bonded, form a cycloheteroalkyl or substituted cycloheteroalkyl ring; and R$^{45}$ is hydrogen, alkyl or substituted alkyl.

In one embodiment of Formula (VIII), R$^{31}$ and R$^{32}$, together with the atoms to which they are bonded, form an aryl, substituted aryl, cycloalkyl, substituted cycloalkyl, heteroaryl or substituted heteroaryl ring.

In one embodiment of Formula (VIII), R$^{31}$ and R$^{32}$ together with the atoms to which they are bonded form a thienyl, substituted thienyl, furanyl, substituted furanyl, pyridinyl, substituted pyridinyl, pyrimidinyl, substituted pyrimidinyl, oxazolyl, substituted oxazolyl, phenyl or substituted phenyl ring.

In one embodiment of Formula (VIII), R$^{31}$ and R$^{32}$, taken together with the atoms to which they are bonded, form a phenyl or substituted phenyl ring.

In one embodiment of Formula (VIII), D and E are C(=O).

In one embodiment of Formula (VIII), A is CR$^{33}$ and B is NR$^{34}$.

In one embodiment of Formula (VIII), D and E are C(=O), A is CR$^{33}$ and B is NR$^{34}$.

In specific embodiments of Formula (VIII), the compound has a structure selected from the group consisting of:

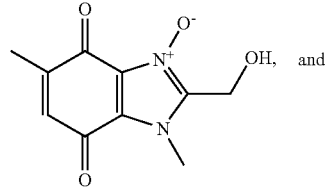

351

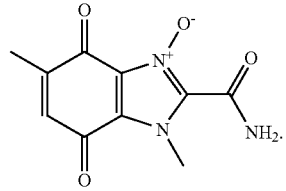

353 or a salt, solvate, or physiologically functional derivative thereof.

In one embodiment of Formula (VIII), A is N and B is NR$^{34}$.

In one embodiment of Formula (VIII), D and E are C(=O), A is N and B is NR$^{34}$.

In specific embodiments of Formula (VIII), the compound has a structure selected from the group consisting of:

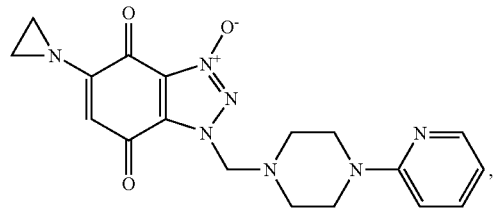

355

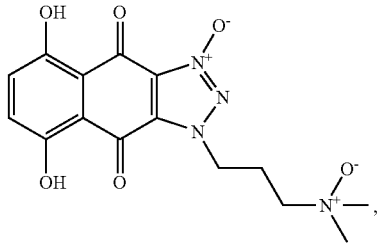

357

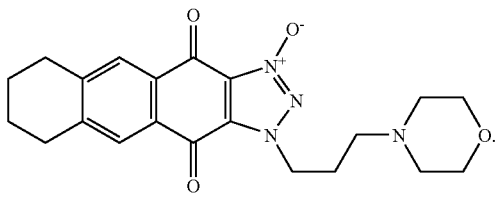

359 or a salt, solvate, or physiologically functional derivative thereof.

In one embodiment of Formula (VIII), the compound has a structural Formula (IX):

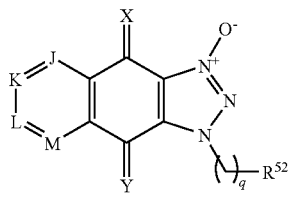

(IX)

or a salt, solvate, or physiologically functional derivative thereof;

wherein q is 0, 1, 2, 3, 4 or 5;

X and Y are independently O, S, or $NR^{51}$;

J, K, L and M are independently $CR^{55}$ or N.

$R^{51}$ is hydrogen, alkyl or substituted alkyl;

$R^{52}$ is halo, cycloheteroalkyl, substituted cycloheteroalkyl, —OC(O)$R^{54}$, —$NR^{53}R^{54}$, —N($R^{53}$)C(O)$R^{54}$, heteroalkyl, substituted heteroalkyl, aryl, substituted aryl, —C(O)$NR^{53}R^{54}$, heteroaryloxy or substituted heteroaryloxy;

$R^{53}$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{53}$ and $R^{54}$, taken together with the atoms to which they are bonded, form a cycloheteroalkyl or substituted cycloheteroalkyl ring;

$R^{54}$ is hydrogen, amino, substituted amino, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{53}$ and $R^{54}$, taken together with the atoms to which they are bonded, form a cycloheteroalkyl or substituted cycloheteroalkyl ring;

$R^{55}$ is halo, cyano, nitro, hydrogen, $OR^{56}$, $S(O)_tR^{56}$, $CO_2R^{56}$, C(O)$NR^{56}R^{57}$ or $NR^{56}R^{57}$;

t is 0, 1, or 2; and $R^{56}$ and $R^{57}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{56}$ and $R^{57}$, taken together with the atoms to which they are bonded, form a cycloheteroalkyl or substituted cycloheteroalkyl ring.

In one embodiment of Formula (IX), X and Y are O.

In one embodiment of Formula (IX), q is 0 and $R^{52}$ is —$NR^{53}R^{54}$.

In specific embodiments of Formula (IX) wherein q is 0, the compound has a structure selected from the group consisting of

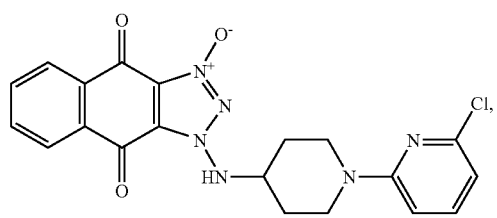

401 and

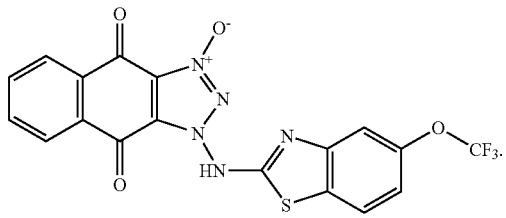

403 or a salt, solvate, or physiologically functional derivative thereof.

In one embodiment of Formula (IX), q is 1 and $R^{52}$ is heteroalkyl, substituted heteroalkyl, aryl, substituted aryl, cycloheteroalkyl or substituted cycloheteroalkyl.

In one embodiment of Formula (IX) wherein q is 1, $R^{52}$ is substituted phenyl. In specific examples, the substituted phenyl comprises one or more substituents selected from the group consisting of cycloheteroalkyl, substituted cycloheteroalkyl, heteroaryl, substituted heteroaryl, phenyl, and substituted phenyl:

In one embodiment of Formula (IX) wherein q is 1, $R^{52}$ is

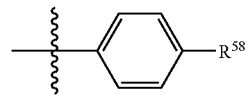

and $R^{58}$ is cycloheteroalkyl, substituted cycloheteroalkyl, heteroaryl, substituted heteroaryl, phenyl or substituted phenyl.

In specific embodiments of Formula (IX) wherein q is 1, the compound has a structure selected from the group consisting of:

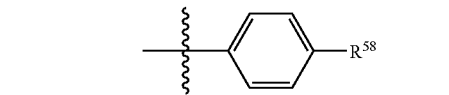

405

, and

407 or a salt, solvate, or physiologically functional derivative thereof.

In one embodiment of Formula (IX), q is 2 and $R^{52}$ is alkyl, substituted alkyl, aryl, substituted aryl, cycloheteroalkyl or substituted cycloheteroalkyl, —OC(O)$R^{54}$ or $NR^{53}R^{54}$.

In one embodiment of Formula (IX) wherein q is 2, $R^{52}$ is substituted phenyl. In specific examples, the substituted phenyl comprises one or more substituents selected from the group consisting of phenyl, substituted phenyl, heteroaryl, substituted heteroaryl, cycloalkyl, substituted cycloalkyl, cycloheteroalkyl or substituted cycloheteroalkyl.

In one embodiment of Formula (IX) wherein q is 2, $R^{52}$ is $OC(O)R^{54}$.

In one embodiment of Formula (IX) wherein q is 2, $R^{52}$ is $NR^{53}R^{54}$ and $R^{53}$ and $R^{54}$, taken together with the atoms to which they are bonded, form a cycloheteroalkyl or substituted cycloheteroalkyl ring.

In specific embodiments of Formula (IX) wherein q is 2, the compound has a structure selected from the group consisting of:

or a salt, solvate, or physiologically functional derivative thereof.

In one embodiment of Formula (IX), q is 3 and $R^{52}$ is aryl, substituted aryl, heteroaryl, substituted heteroaryl, cycloheteroalkyl, substituted cycloheteroalkyl or $NR^{53}R^{54}$.

In one embodiment of Formula (IX) wherein q is 3, $R^{52}$ is substituted cycloheteroalkyl which comprises substituents selected from the group consisting of aryl, substituted aryl, alkyl, substituted alkyl, arylalkyl, substituted arylalkyl,

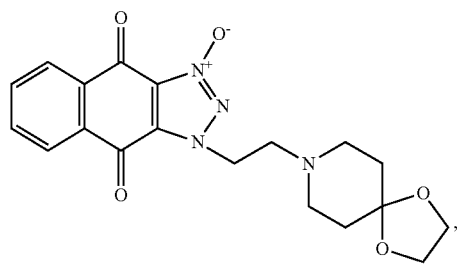

411

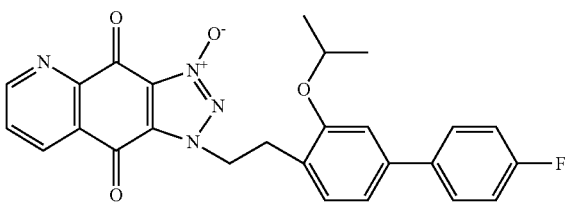

413

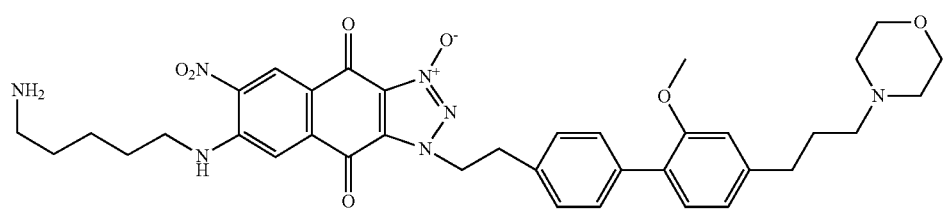

415

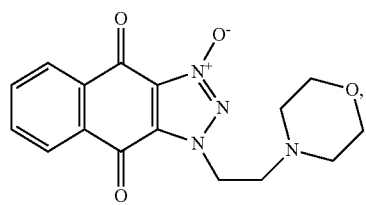

417

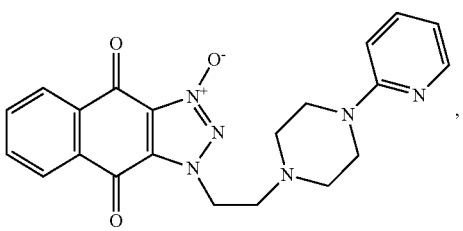

419

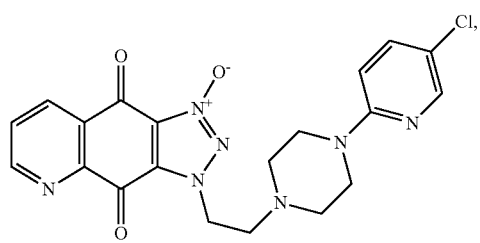

421

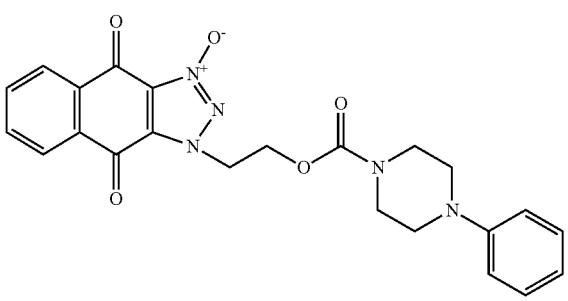

423

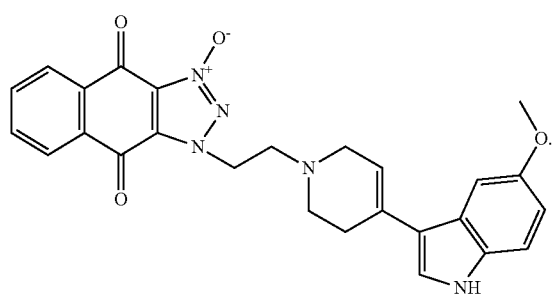

425 cycloalkyldiyl, substituted cycloalkydiyl, cycloheteroalkyldiyl, substituted cycloheteroalkydiyl, and hydroxyl.

In one embodiment of Formula (IX) wherein q is 3, R$^{52}$ is NR$^{53}$R$^{54}$ wherein R$^{53}$ and R$^{54}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{53}$ and R$^{54}$, taken together with the atoms to which they are bonded, form a cycloheteroalkyl or substituted cycloheteroalkyl ring.

In specific embodiments of Formula (IX) wherein q is 3, the compound has a structure selected from the group consisting of:

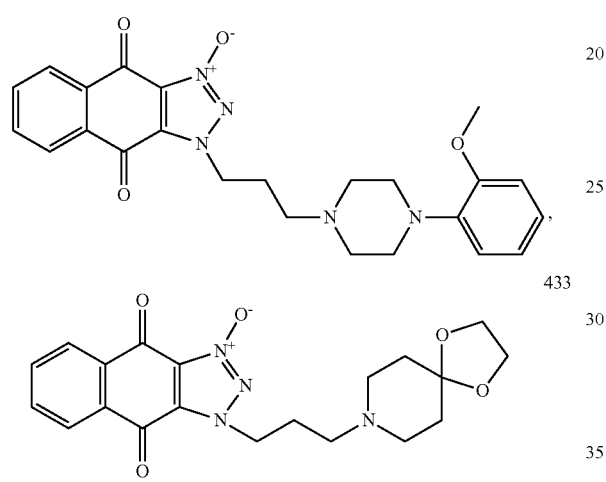
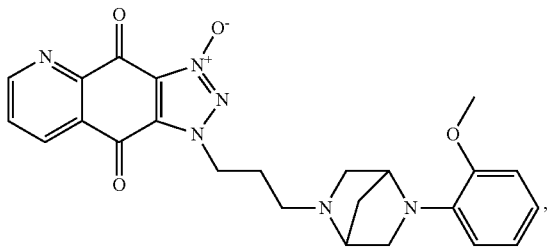

-continued

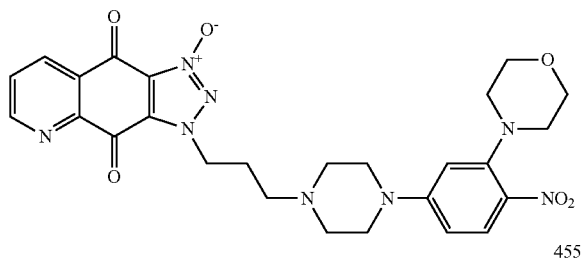

453

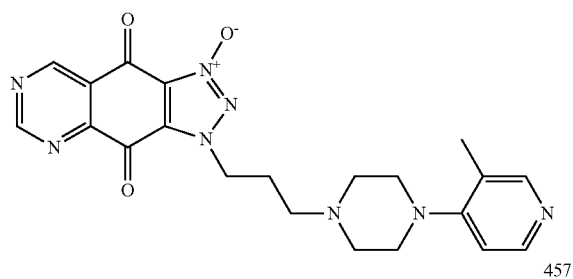

455

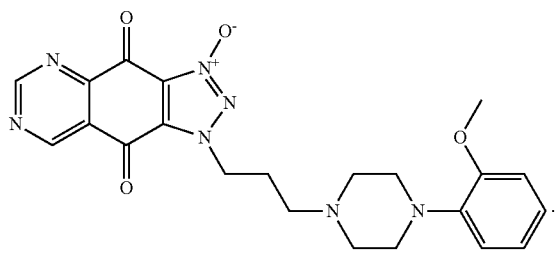

457 or a salt, solvate, or physiologically functional derivative thereof.

In another aspect, the present invention provides a compound having structural Formula (X):

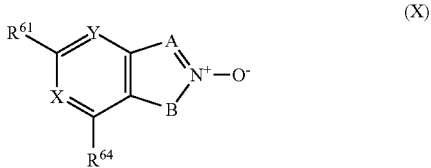

(X)

or a salt, solvate, or physiologically functional derivative thereof;
wherein: A is N, or C(R$^{65}$); B is N(R$^{68}$), C(R$^{69}$R$^{70}$), C(R$^{71}$), C(=NR$^{72}$), O, S, or C(=O);

X is N or CR$^{62}$; Y is N or CR$^{63}$;

R$^{61}$ and R$^{62}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; or alternatively, R$^{61}$ and R$^{62}$, taken together with the atoms to which they are bonded, form an aryl, substituted aryl, cycloalkyl, substituted cycloalkyl, cycloheteroalkyl, substituted cycloheteroalkyl, heteroaryl or substituted heteroaryl ring;

R$^{63}$ and R$^{64}$ are independently halo, cyano, nitro, hydrogen, OR$^{66}$, S(O)$_t$R$^{66}$, CO$_2$R$^{66}$, CONR$^{66}$R$^{67}$, NR$^{66}$R$^{67}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; t is 0, 1 or 2;

R$^{65}$ is halo, hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —N=NR$^{73}$, —C(O)NR$^{73}$R$^{74}$ or —S(O)$_2$NR$^{73}$R$^{74}$;

R$^{68}$ is halo, hydrogen, alkyl, substituted alkyl, acyl, substituted acyl, aryl, substituted aryl, arylalkyl, substituted arylalkyl, aryloxy, substituted aryloxy, heteroaryl, substituted heteroaryl, heteroarylalkyl, substituted heteroarylalkyl, heteroalkyl, substituted heteroalkyl, or —C(O)NR$^{75}$R$^{76}$ or —S(O)$_2$NR$^{75}$R$^{76}$;

R$^{69}$, R$^{70}$ and R$^{72}$ are independently hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —C(O)NR$^{77}$R$^{78}$ or —S(O)$_2$NR$^{77}$R$^{78}$;

R$^{71}$ is alkyldiyl, substituted alkyldiyl, heteroalkyldiyl or substituted heteroalkyldiyl; and R$^{66}$, R$^{67}$, R$^{73}$, R$^{74}$, R$^{75}$, R$^{76}$, R$^{77}$ and R$^{78}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl.

In one embodiment of Formula (X), R$^{61}$ and R$^{62}$, taken together with the atoms to which they are bonded, form an aryl, substituted aryl, cycloalkyl, substituted cycloalkyl, heteroaryl or substituted heteroaryl ring.

In one embodiment of Formula (X), R$^{61}$ and R$^{62}$, taken together with the atoms to which they are bonded, form a thienyl, substituted thienyl, furanyl, substituted furanyl, pyridinyl, substituted pyridinyl, pyrimidinyl, substituted pyrimidinyl, oxazolyl, substituted oxazolyl, phenyl or substituted phenyl ring.

In one embodiment of Formula (X), R$^{63}$ and R$^{64}$ are hydrogen.

In one embodiment of Formula (X), A is CR$^{65}$ and B is NR$^{68}$.

In one embodiment of Formula (X), R$^{63}$ and R$^{64}$ are hydrogen, A is CR$^{65}$ and B is NR$^{68}$.

In specific embodiments of Formula (X), the compound has a structure selected from the group consisting of:

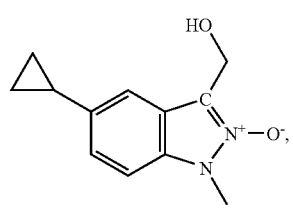

501

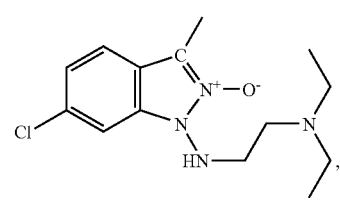

503

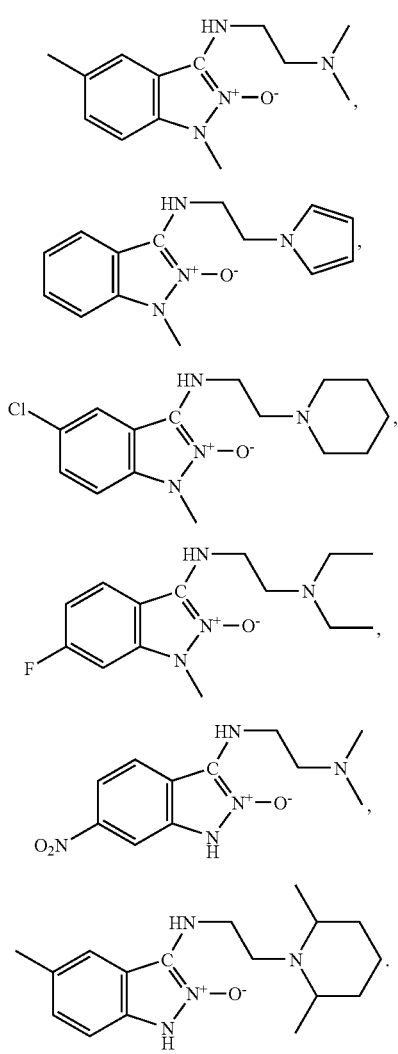

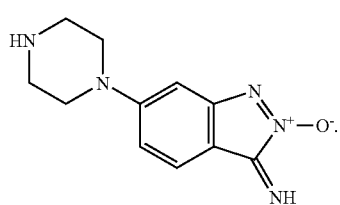

or a salt, solvate, or physiologically functional derivative thereof.

In one embodiment of Formula (X), A is N and B is C(NR$^{72}$).

In one embodiment of Formula (X), R$^{63}$ and R$^{64}$ are hydrogen, A is N and B is C(=NR$^{72}$).

In a specific embodiment of Formula (X), the compound contains the following structure:

In specific embodiments of Formula (X), the compound has a structure selected from the group consisting of:

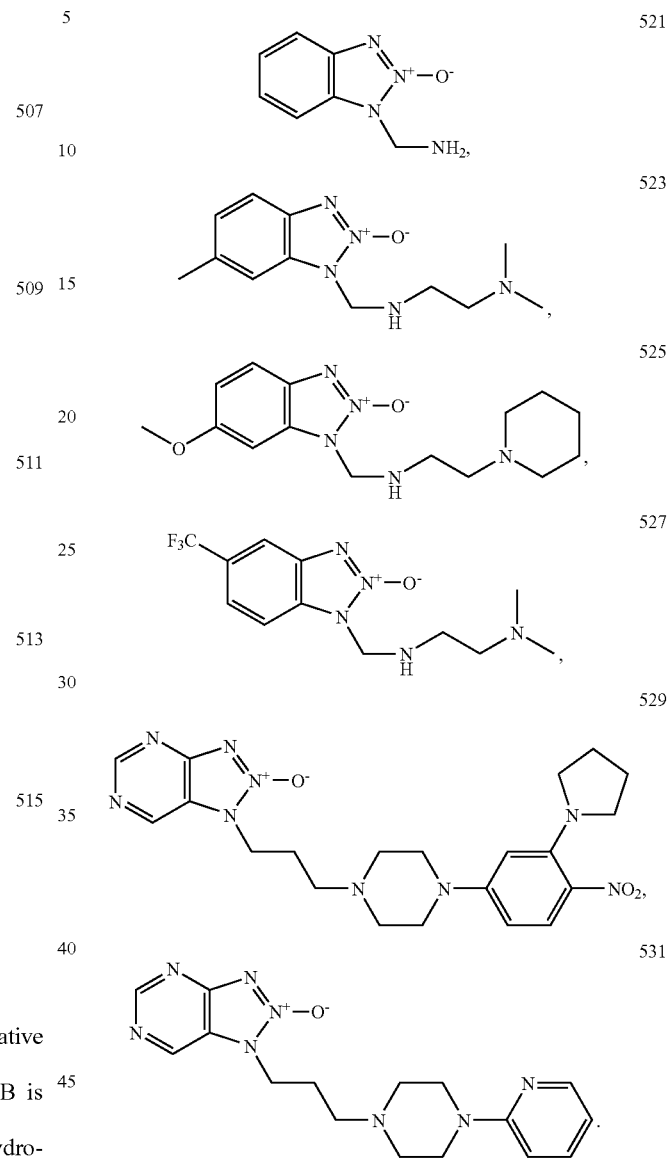

or a salt, solvate, or physiologically functional derivative thereof.

In another aspect, the present invention provides a compound having structural Formula (XI) or (XII):

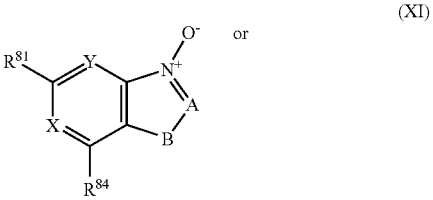

or a salt, solvate, or physiologically functional derivative thereof.

In one embodiment of Formula (X), A is N and B is NR$^{68}$.

In one embodiment of Formula (V), R$^{63}$ and R$^{64}$ are hydrogen, A is N and B is NR$^{68}$.

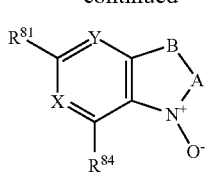

(XII)

or a salt, solvate, or physiologically functional derivative thereof;
wherein X is N or $CR^{82}$; Y is N or $CR^{83}$;

$R^{81}$ and $R^{82}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; or alternatively, $R^{81}$ and $R^{82}$, together with the atoms to which they are bonded, form an aryl, substituted aryl, cycloalkyl, substituted cycloalkyl, cycloheteroalkyl, substituted cycloheteroalkyl, heteroaryl or substituted heteroaryl ring;

$R^{83}$ and $R^{84}$ are independently halo, cyano, nitro, hydrogen, $OR^{86}$, $S(O)_tR^{86}$, $CO_2R^{86}$, $CONR^{86}R^{87}$, $NR^{86}R^{87}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; t is 0, 1 or 2;

A is N, $N^+$—$O^-$, or $C(R^{85})$;
B is $N(R^{88})$, $C(R^{89}R^{91})$, $C(R^{91})$, $C(=NR^{92})$, O, S, or $C(=O)$;

$R^{85}$ is halo, hydrogen, amino, substituted amino, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —N=$NR^{93}$, —C(O)$NR^{93}R^{94}$ or —S(O)$_2NR^{93}R^{94}$;

$R^{88}$ is hydrogen, alkyl, substituted alkyl, acyl, substituted acyl, aryl, substituted aryl, arylalkyl, substituted arylalkyl, aryloxy, substituted aryloxy, heteroaryl, substituted heteroaryl, heteroarylalkyl, substituted heteroarylalkyl, heteroalkyl, substituted heteroalkyl, or —C(O)$NR^{95}R^{96}$ or —S(O)$_2NR^{95}R^{96}$;

$R^{89}$, $R^{90}$ and $R^{92}$ are independently hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —C(O)$NR^{97}R^{98}$ or —S(O)$_2NR^{97}R^{98}$;

$R^{91}$ is alkyldiyl, substituted alkyldiyl, halo, heteroalkyldiyl or substituted heteroalkyldiyl; and $R^{86}$, $R^{87}$, $R^{93}$, $R^{94}$, $R^{95}$, $R^{96}$, $R^{97}$ and $R^{98}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl.

In one embodiment of Formula (XI) or (XII), X is $CR^{82}$ and Y is $CR^{83}$.

In one embodiment of Formula (XI) or (XII), $R^{81}$ and $R^{82}$, together with the atoms to which they are bonded, form an aryl, substituted aryl, cycloalkyl, substituted cycloalkyl, heteroaryl or substituted heteroaryl ring.

In one embodiment of Formula (XI) or (XII), $R^{81}$ and $R^{82}$ together with the atoms to which they are bonded form a thienyl, substituted thienyl, furanyl, substituted furanyl, pyridinyl, substituted pyridinyl, pyrimidinyl, substituted pyrimidinyl, oxazolyl, substituted oxazolyl, phenyl or substituted phenyl ring.

In one embodiment of Formula (XI) or (XII), $R^{81}$ and $R^{82}$, taken together with the atoms to which they are bonded, form a phenyl or substituted phenyl ring.

In one embodiment of Formula (XI) or (XII), $R^{83}$ and $R^{84}$ are hydrogen.

In one embodiment of Formula (XI) or (XII), A is $CR^{85}$ and B is $NR^{88}$.

In specific embodiments of Formula (XI) or (XII), the compound has a structure selected from the group consisting of:

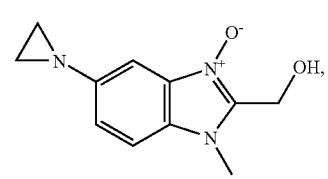

551

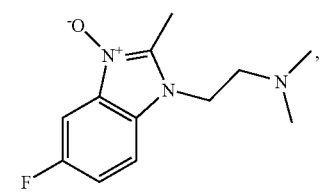

553

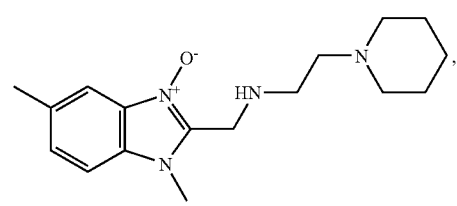

555

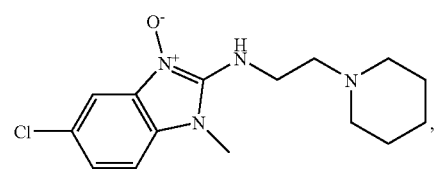

557

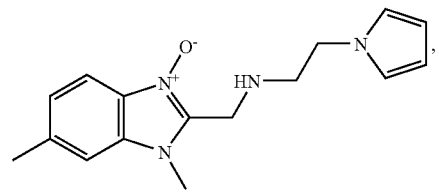

559

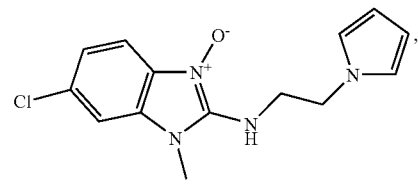

561

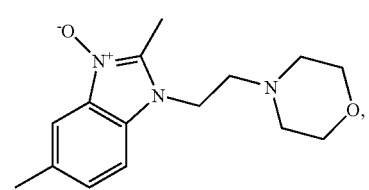

563

-continued

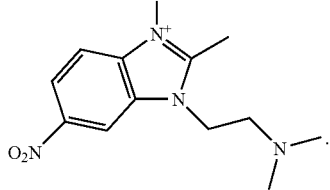
565 or a salt, solvate, or physiologically functional derivative thereof.

In one embodiment of Formula (XI) or (XII), A is $CR^{85}$ and B is C(=O).

In specific embodiments of Formula (XI) or (XII), the compound has a structure selected from the group consisting of:

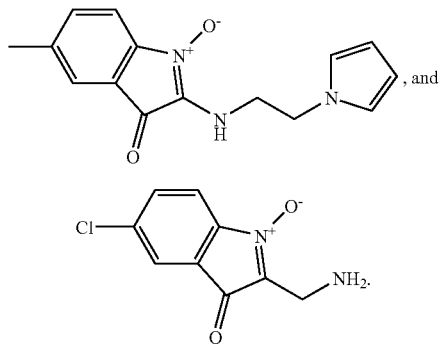

or a salt, solvate, or physiologically functional derivative thereof.

In one embodiment of Formula (XI) or (XII), $R^{83}$ and $R^{84}$ are hydrogen or hydroxy.

In one embodiment of Formula (XI) or (XII), A is $N^+$—$O^-$ and B is $NR^{88}$.

In one embodiment of Formula (XI) or (XII), $R^{83}$ and $R^{84}$ are hydrogen or hydroxy, A is $N^+$—$O^-$ and B is $NR^{88}$.

In specific embodiments of Formula (XI) or (XII), the compound has a structure selected from the group consisting of:

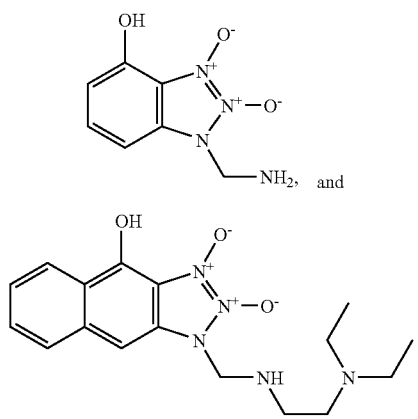

or a salt, solvate, or physiologically functional derivative thereof.

In one embodiment of Formula (XI) or (XII), X and Y are nitrogen.

In one embodiment of Formula (XI) or (XII), A is N and B is $NR^{88}$.

In one embodiment of Formula (XI) or (XII), X and Y are nitrogen, A is N and B is $NR^{88}$.

In specific embodiments of Formula (XI) or (XII), the compound a structure selected from the group consisting of:

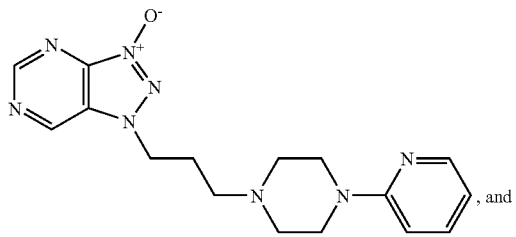

or a salt, solvate, or physiologically functional derivative thereof.

In another aspect, the present invention provides a compound having structural Formula (XIII):

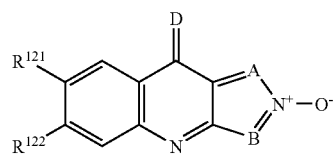

(XIII)

or a salt, solvate, or physiologically functional derivative thereof;

wherein: A and B are independently N or $C(R^{123})$; D is O, S, or NH;

$R^{121}$ and $R^{122}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

$R^{123}$ hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —N=$NR^{124}$, —C(O)$NR^{124}R^{125}$ or —S(O)$_2NR^{124}R^{125}$; and $R^{124}$ and $R^{125}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{124}$ and $R^{125}$ taken together with the atoms to which they are bonded form cycloheteroalkyl or substituted cycloheteroalkyl ring.

In another aspect, the present invention provides a compound having structural Formula (XIV):

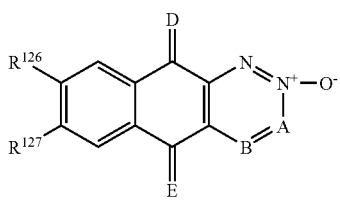
(XIV)

or a salt, solvate, or physiologically functional derivative thereof;
wherein: A and B are independently N or C($R^{128}$); D and E are independently O, S, or NH;

$R^{126}$ and $R^{127}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

$R^{128}$ hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —N=$NR^{129}$, —C(O)$NR^{129}R^{130}$ or —S(O)$_2NR^{129}R^{130}$; and $R^{129}$ and $R^{130}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{129}$ and $R^{130}$ taken together with the atoms to which they are bonded form cycloheteroalkyl or substituted cycloheteroalkyl ring.

In specific embodiments of Formula (XIII), the compound has the following structure:

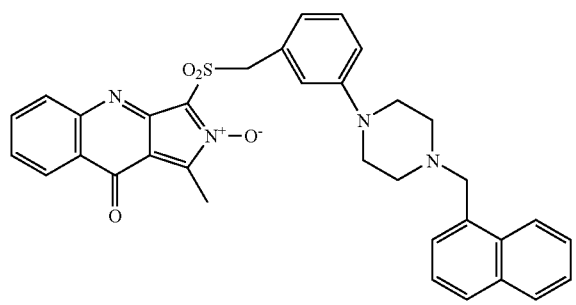 [SMILES: CC1=C2C(=O)c3ccccc3N=C2C(S(=O)(=O)Cc2cccc(N3CCN(Cc4cccc5ccccc45)CC3)c2)=[N+]1[O-]]

or a salt, solvate, or physiologically functional derivative thereof.

In specific embodiments of Formula (XIV), the compound has the following structure:

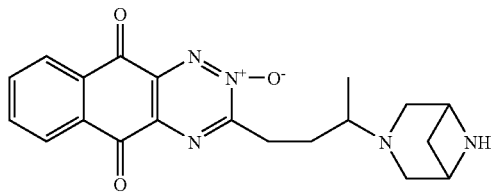
581 or a salt, solvate, or physiologically functional derivative thereof.

In another aspect, the present invention provides a compound having structural. Formula (XV):

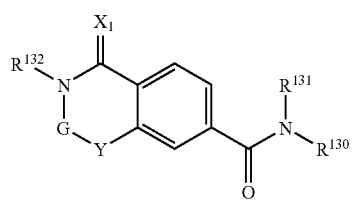
(XV)

or a salt, solvate, or physiologically functional derivative thereof;
wherein: G is —C(=$X_2$) or —$SO_2$—; $X_1$ and $X_2$ are independently O, S, or NH;
X is $NR^{138}$ or O; Y is —$NR^{134}$, O, S, —$CH_2$—;

$R^{130}$ is alkyl, substituted alkyl, aryl, substituted aryl, arylalkyl, substituted arylalkyl, cycloalkyl, substituted cycloalkyl, heteroarylalkyl, substituted heteroarylalkyl, heteroalkyl, substituted heteroalkyl, —S(O)$_tR^{135}$, or alternatively, $R^{130}$ and $R^{131}$ together with the atoms to which they are bonded form a cycloheteroalkyl or substituted cycloheteroalkyl ring;

$R^{131}$ is hydrogen, alkyl or substituted alkyl;

$R^{132}$ is alkyl, substituted alkyl, arylalkyl, substituted arylalkyl, heteroarylalkyl, substituted heteroarylalkyl, —S(O)$_uR^{136}$;

$R^{134}$ is hydrogen, aryl substituted aryl, cycloheteroalkyl, substituted cycloheteroalkyl, —$CH_2$C(O)$XR^{137}$, arylalkyl, substituted arylalkyl, heteroarylalkyl or substituted heteroarylalkyl;

$R^{135}$ is alkyl, substituted alkyl, aryl, substituted aryl, arylalkyl, substituted arylalkyl, cycloalkyl, substituted cycloalkyl, heteroaryl, substituted heteroaryl, heteroarylalkyl, substituted heteroarylalkyl, heteroalkyl or substituted heteroalkyl;

$R^{136}$ is alkyl, substituted alkyl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;

$R^{137}$ is alkyl, substituted alkyl, arylalkyl, substituted arylalkyl, cycloalkyl, substituted cycloalkyl, cycloheteroalkyl, substituted cycloheteroalkyl, heteroarylalkyl, substituted heteroarylalkyl, heteroalkyl or substituted heteroalkyl;

$R^{138}$ is hydrogen, alkyl; and t and u are independently 0, 1 or 2.

In one embodiment of Formula (XV), G is —C(=$X_2$), Y is —$NR^{134}$ and $R^{131}$ is hydrogen.

In one embodiment of Formula (XV), —C(=$X_2$), Y is —$NR^{134}$, $R^{131}$ is hydrogen, and $X_1$ and $X_2$ are O.

In one embodiment of Formula (XV), —C(=X$_2$), Y is —NR$^{134}$, R$^{131}$ is hydrogen, and X$_1$ and X$_2$ are O.

In one embodiment of Formula (XV), —C(=X$_2$), Y is —NR$^{134}$, R$^{131}$ is hydrogen, X$_1$ is O, and X$_2$ is S.

In one embodiment of Formula (XV), —C(=X$_2$), Y is —NR$^{134}$, R$^{131}$ is hydrogen, X$_1$ is NH, and X$_2$ is S.

In one embodiment of Formula (XV), G is —C(=X$_2$), Y is —NR$^{134}$, R$^{131}$ is hydrogen, X$_1$ is O, X$_2$ is S, R$^{32}$ is arylalkyl or substituted arylalkyl, and R$^{130}$ is aryl or substituted aryl.

In one embodiment of Formula (XV), the compounds have structural Formula (XVI):

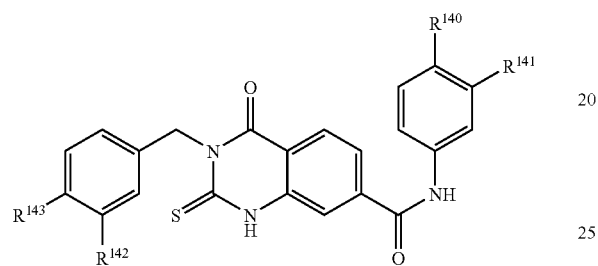

(XVI)

or a salt, solvate, or physiologically functional derivative thereof;

wherein:

R$^{140}$ and R$^{141}$ are independently, hydrogen, halo, cyano, nitro, hydroxy, OR$^{144}$, S(O)$_v$R$^{144}$, CO$_2$H, CO$_2$R$^{144}$, CONR$^{144}$R$^{145}$, NR$^{144}$R$^{145}$, alkyl, substituted alkyl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or R$^{140}$ and R$^{141}$ together with the atoms to which they are bonded, form a cycloalkyl, substituted cycloalkyl, cycloheteroalkyl or substituted cycloheteroalkyl ring; v is 0, 1 or 2;

R$^{142}$ and R$^{143}$ are independently, hydrogen, halo, cyano, nitro, hydroxy, OR$^{146}$, S(O)$_v$R$^{146}$, CO$_2$H, CO$_2$R$^{146}$, CONR$^{146}$R$^{147}$, NR$^{146}$R$^{147}$, alkyl, substituted alkyl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or R$^{142}$ and R$^{143}$ together with the atoms to which they are bonded, form a cycloalkyl, substituted cycloalkyl, cycloheteroalkyl or substituted cycloheteroalkyl ring; and R$^{144}$, R$^{145}$, R$^{146}$ and R$^{147}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{144}$ and R$^{145}$ or R$^{146}$ and R$^{147}$ taken together with the atoms to which they are bonded, form a cycloheteroalkyl or substituted cycloheteroalkyl ring.

In specific embodiments of Formula (XVI), the compound has a structure selected from the group consisting of:

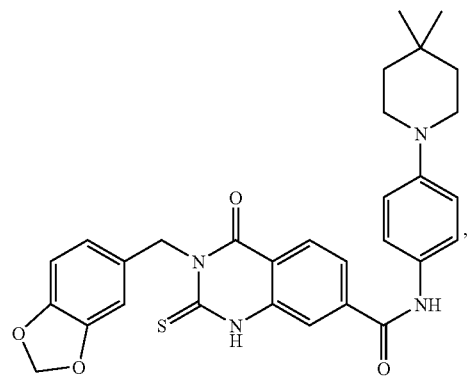

601

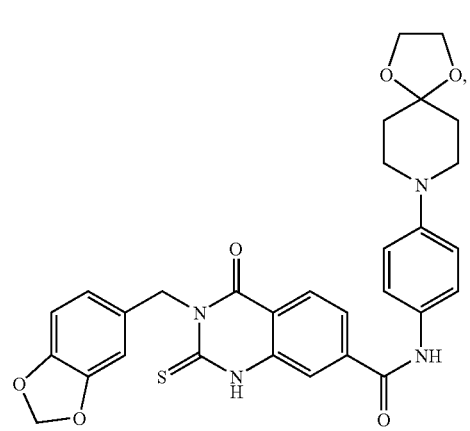

603

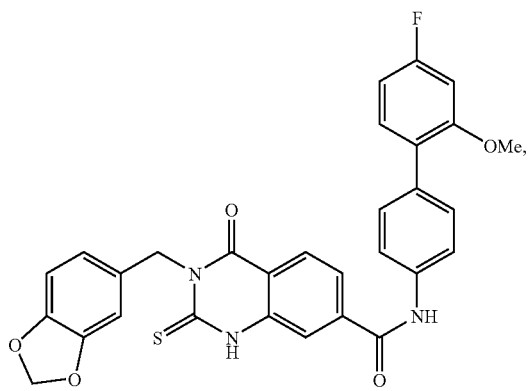

605

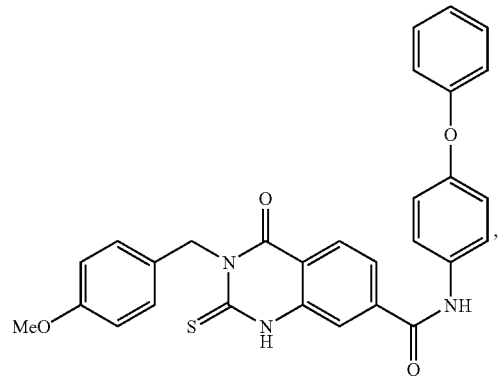

607

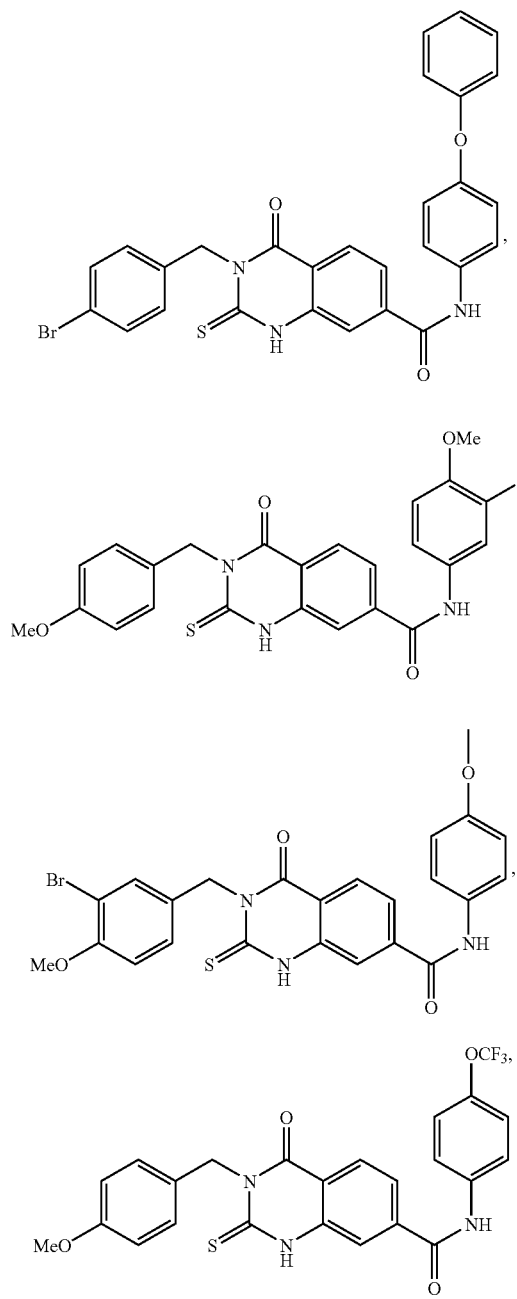
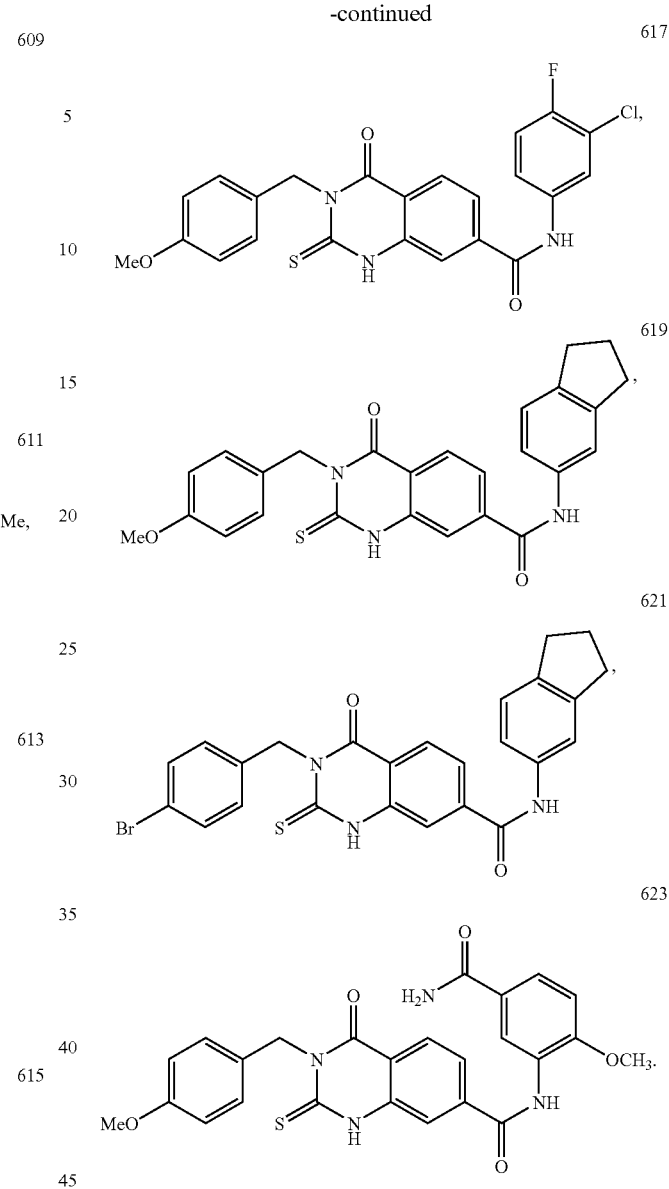
or a salt, solvate, or physiologically functional derivative thereof.
In specific embodiments of Formula (XV), the compound has a structure selected from the group consisting of:
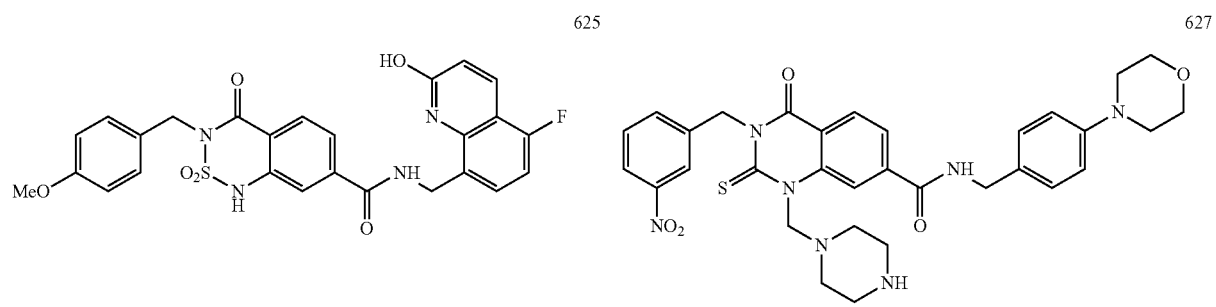

-continued
629
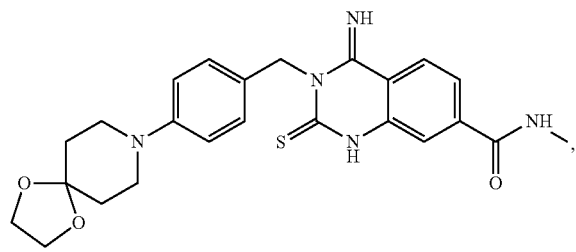
631
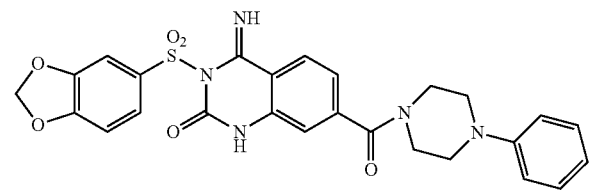
633
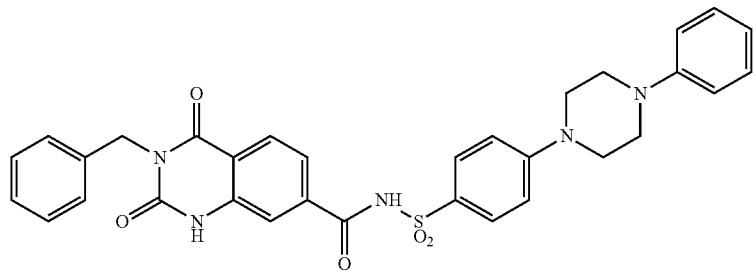
635
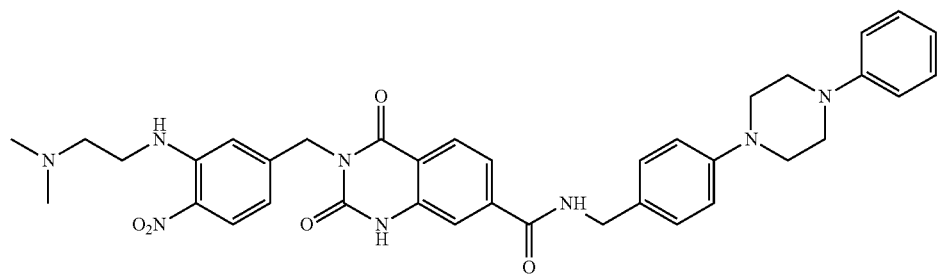
637
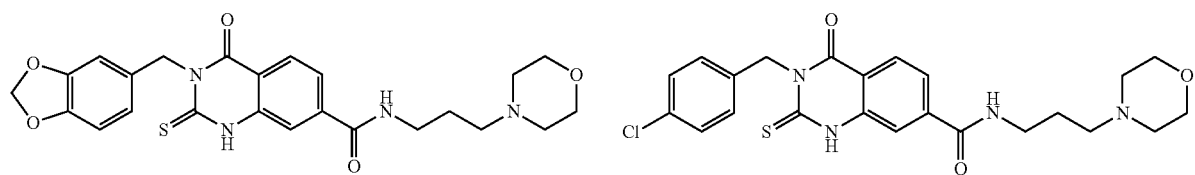
639
641
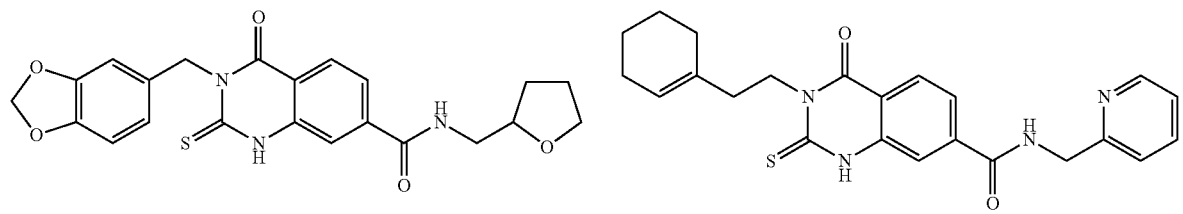
643
645
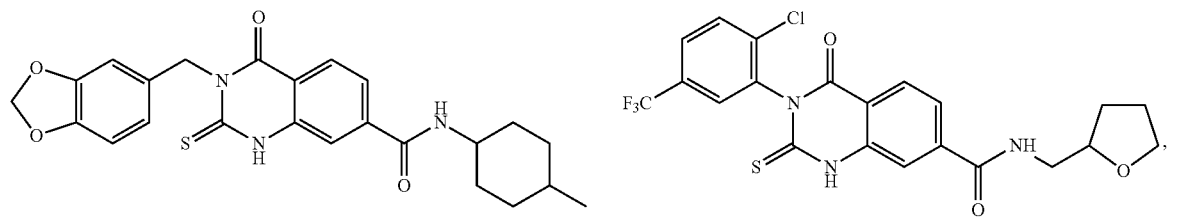
647

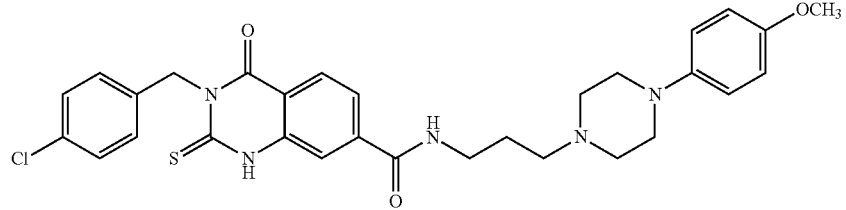
649
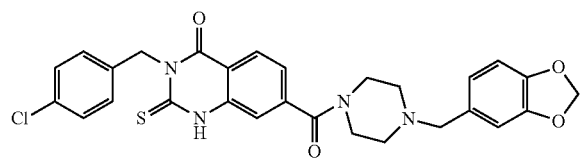
651
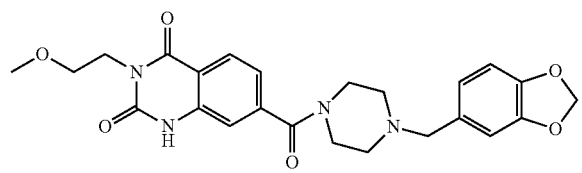
653
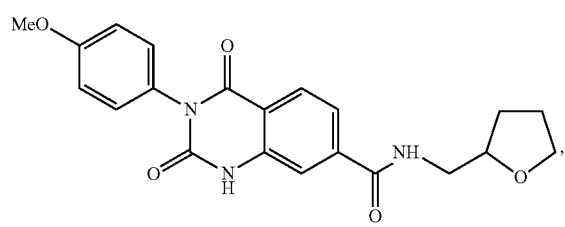
655
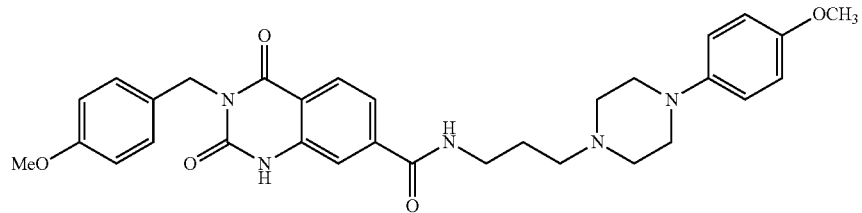
657
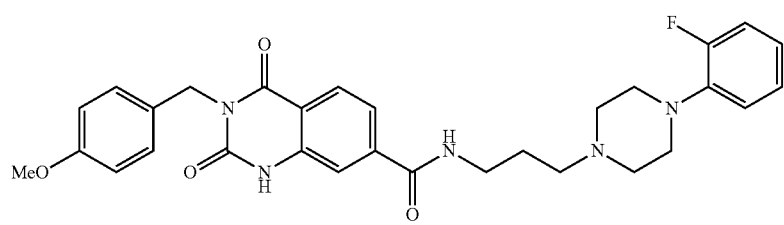
659
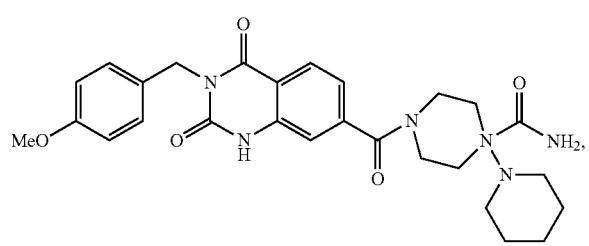
661
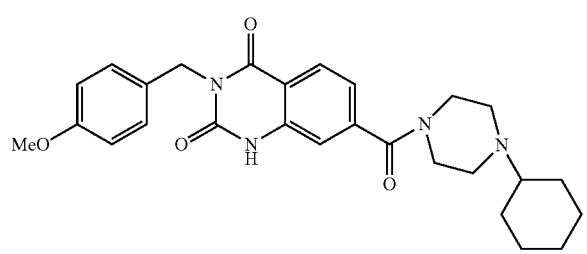
663
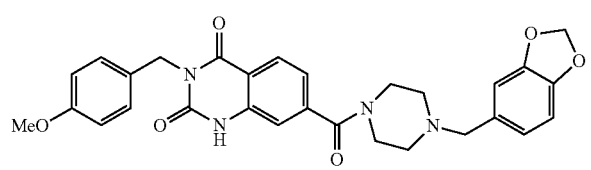
667
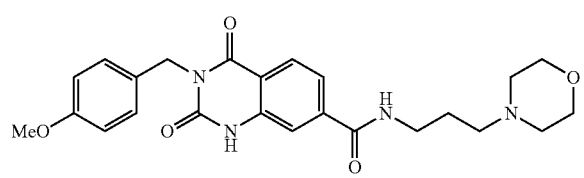
669

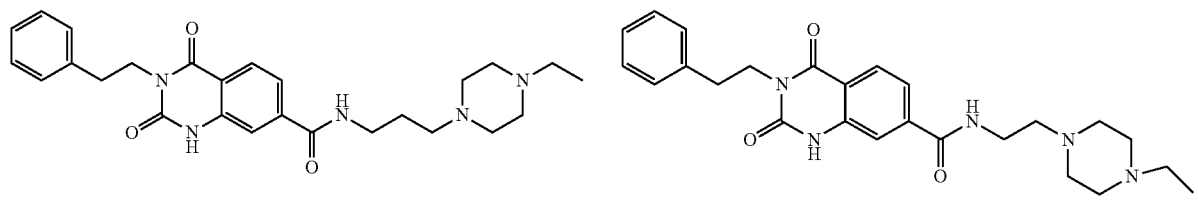
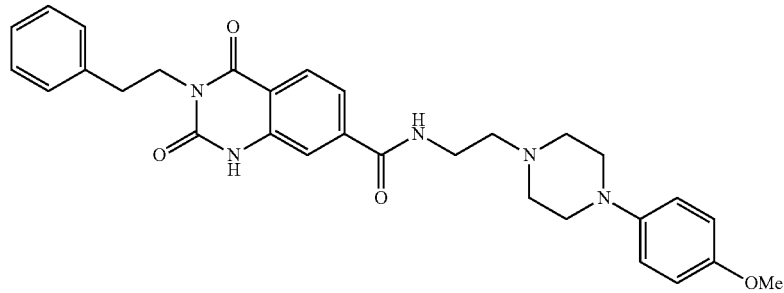
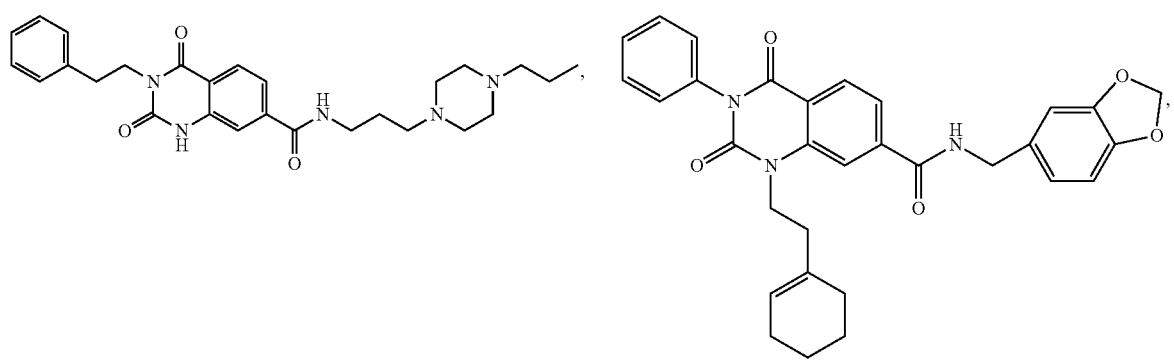
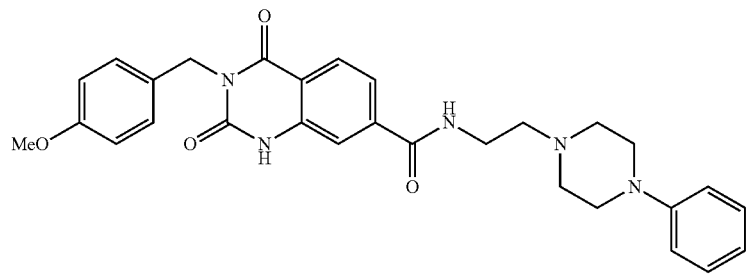
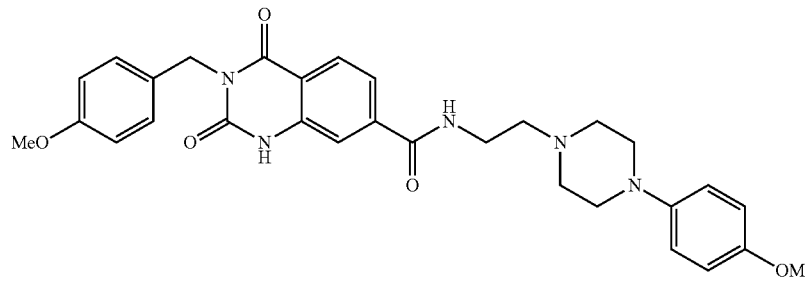

-continued
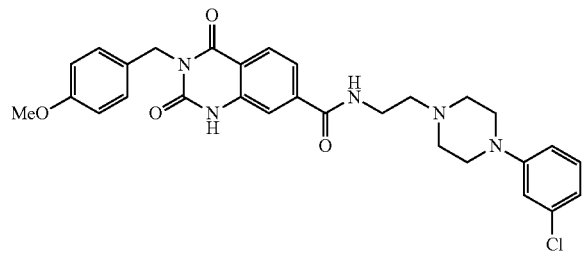
685
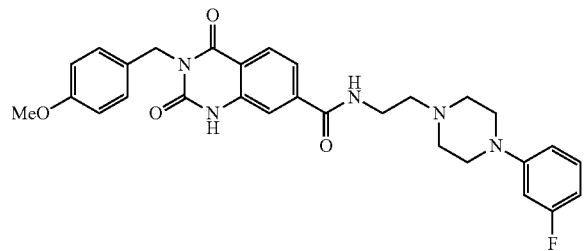
687
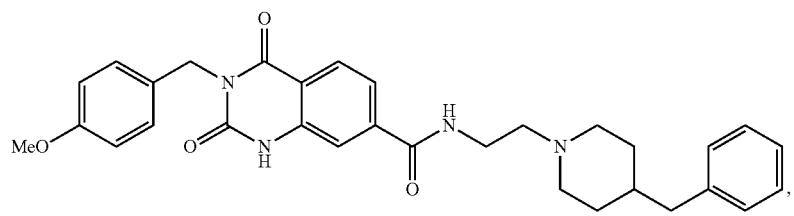
689
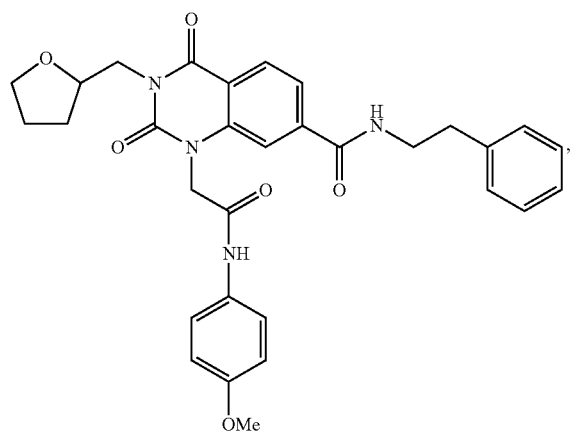
691
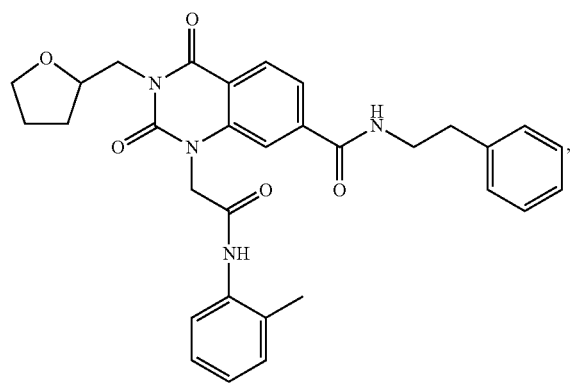
693
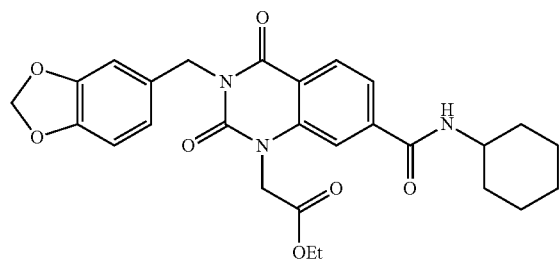
695
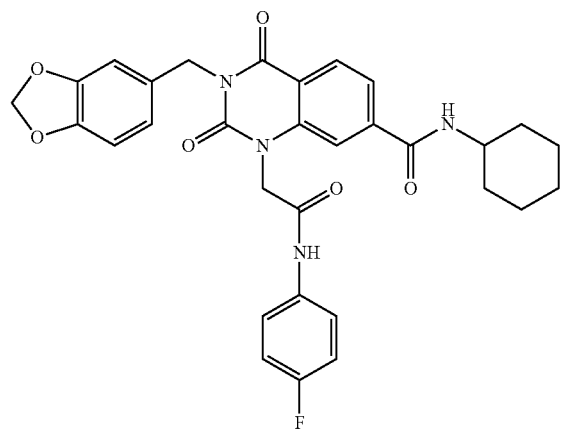
697

-continued
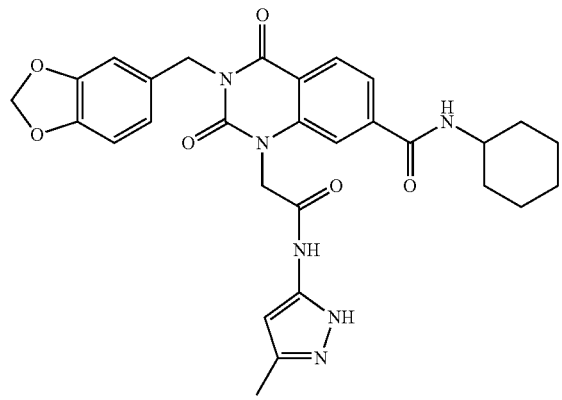 699
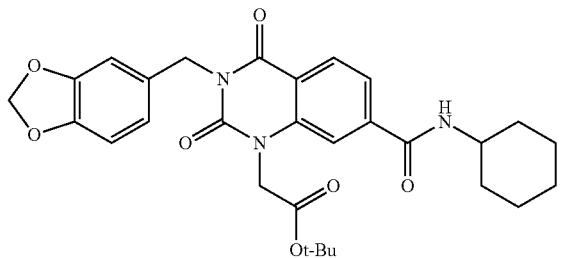 701
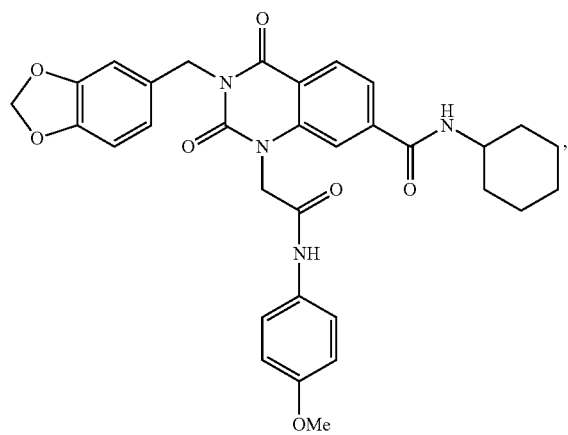 703
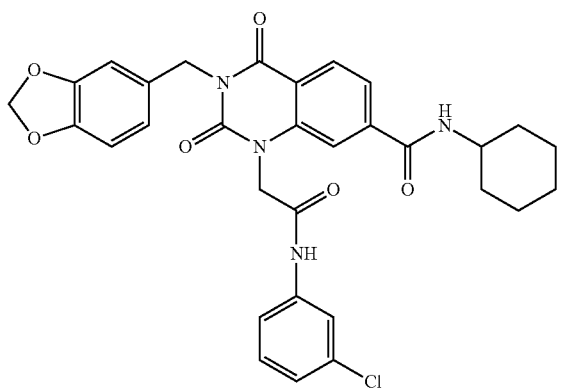 705
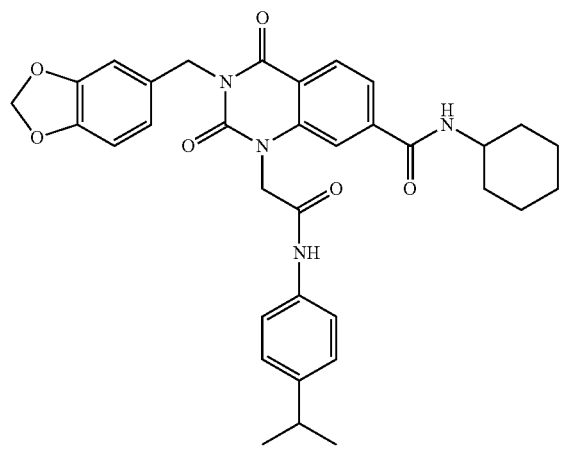 707
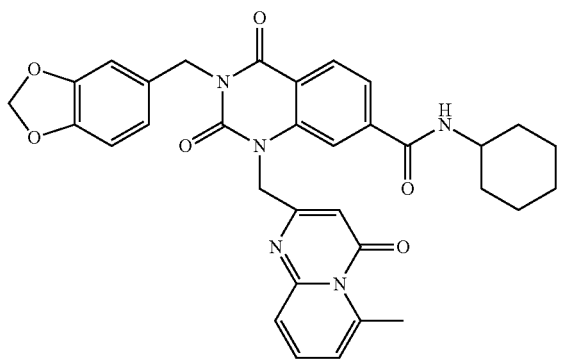 709

-continued
711
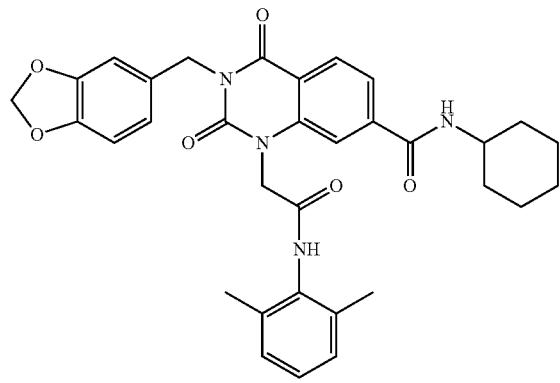
713
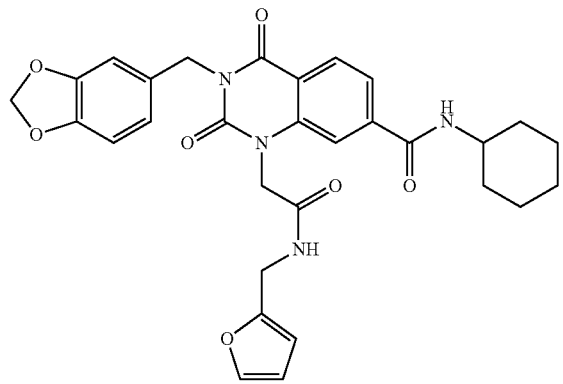
715
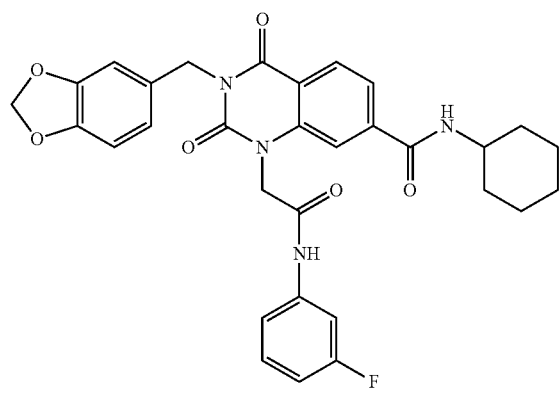
717
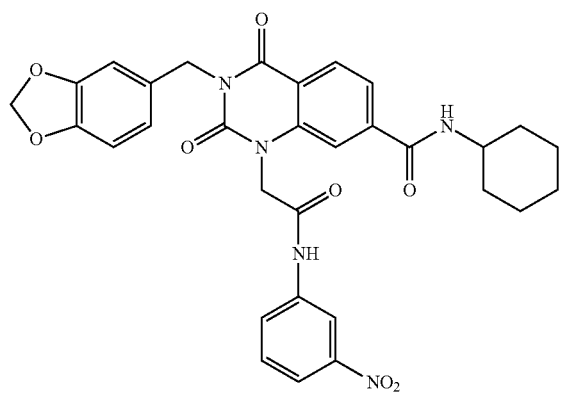
719
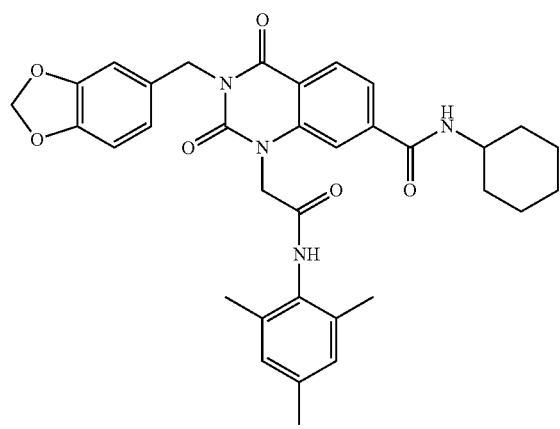
721
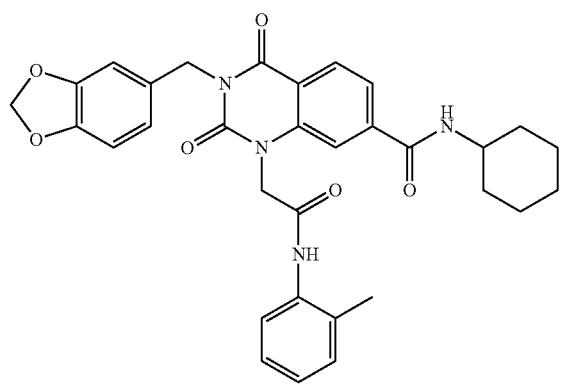

83    84
-continued
723
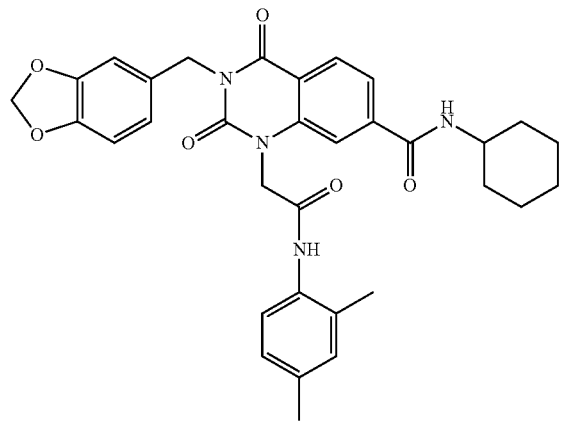
725
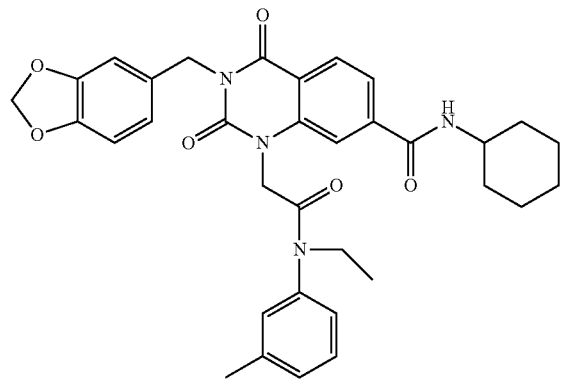
727
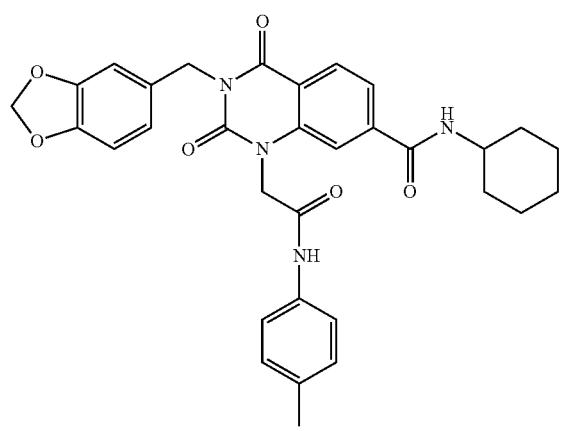
729
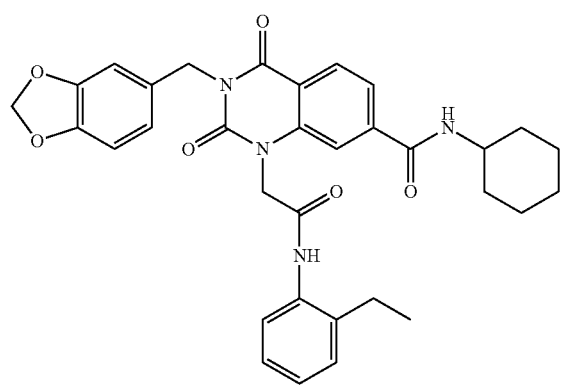
731
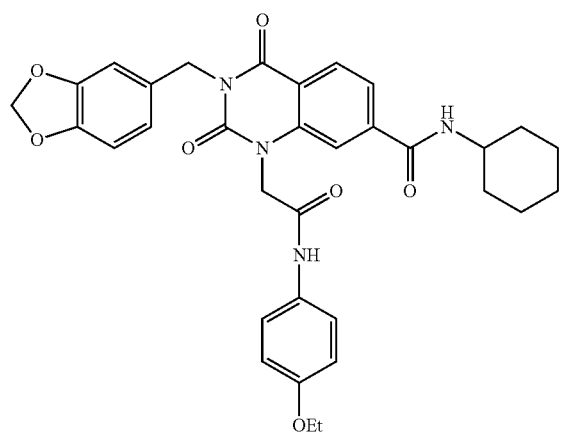
733
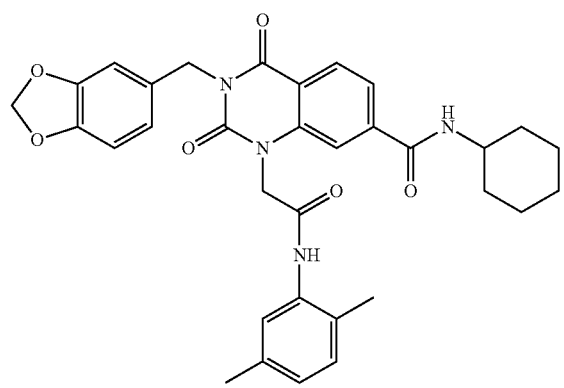

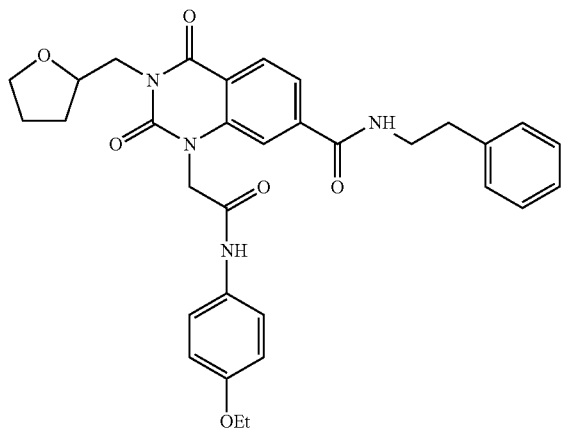
735
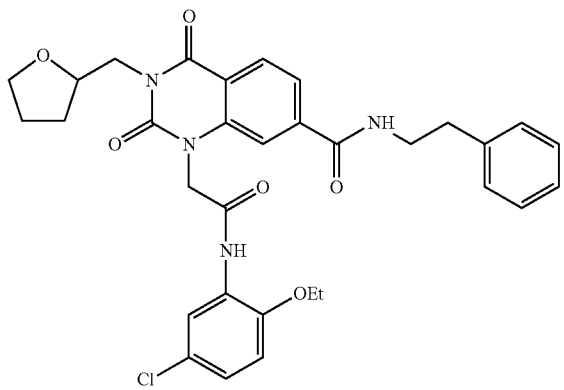
737
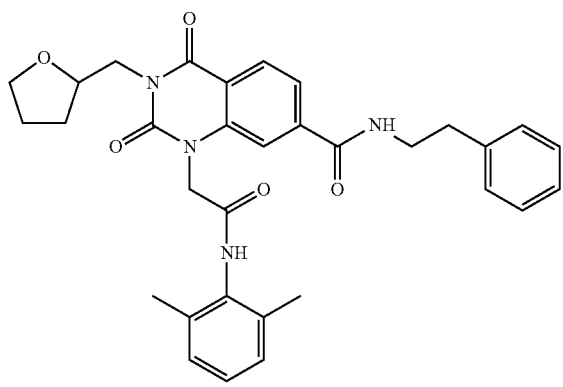
739
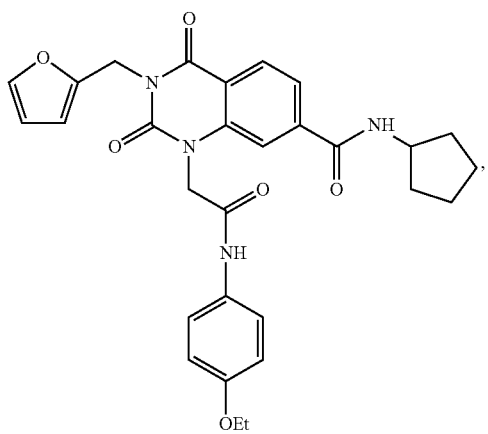
741
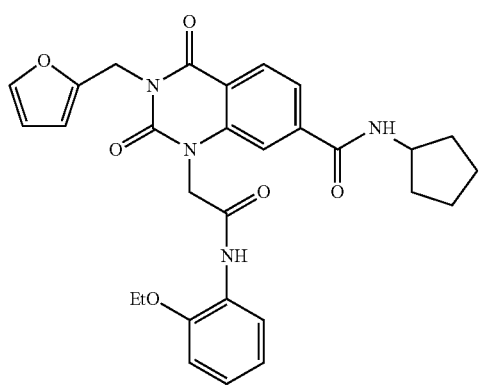
743
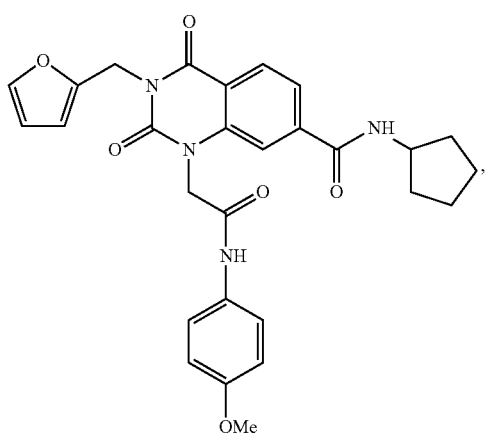
745

-continued
747 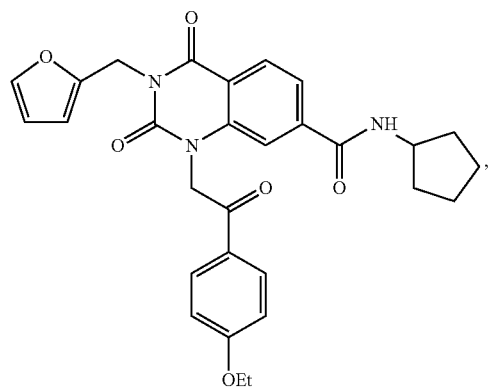
749 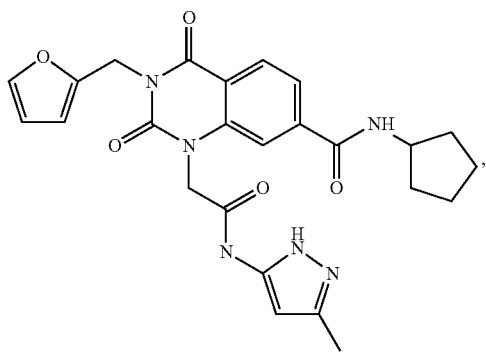
751 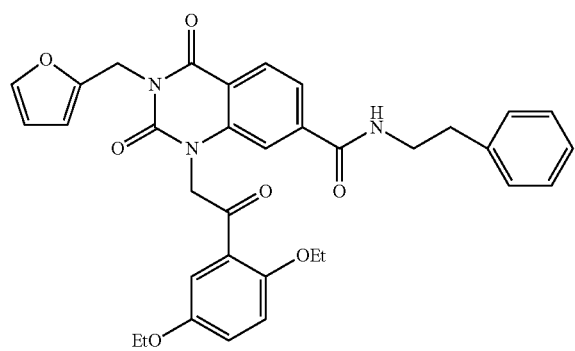
753 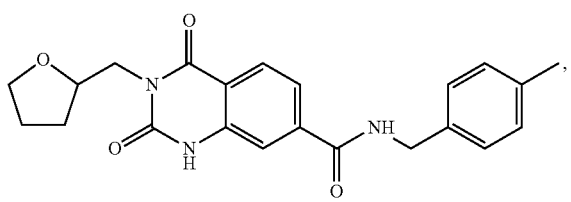
755 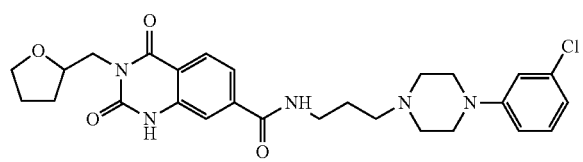
757 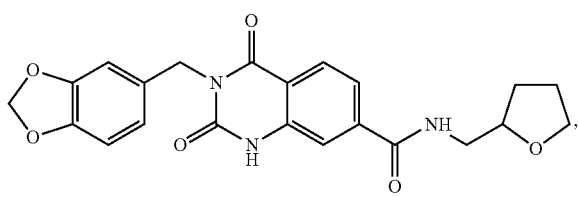
759 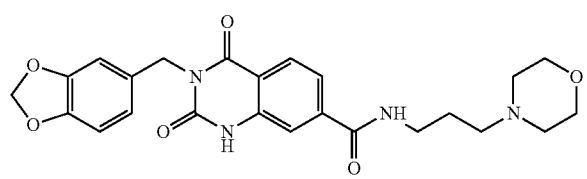
761 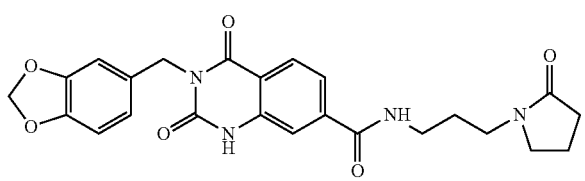
763 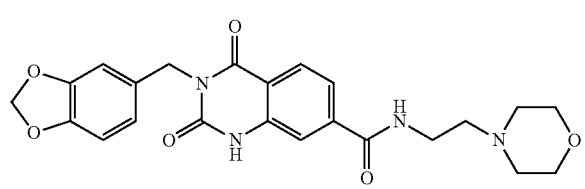
765 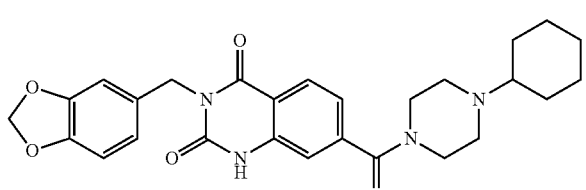
767 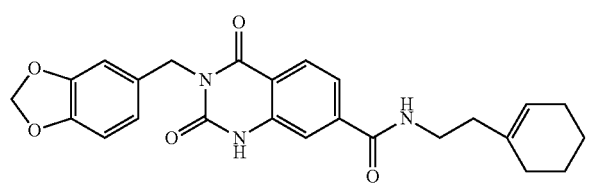
769 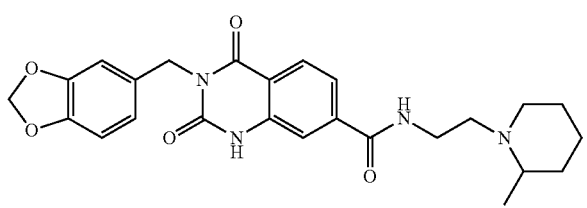

-continued
771
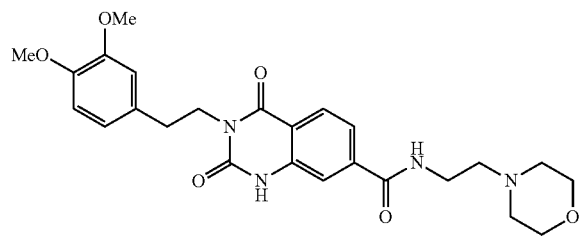
773
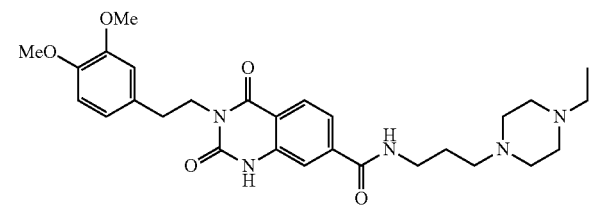
775
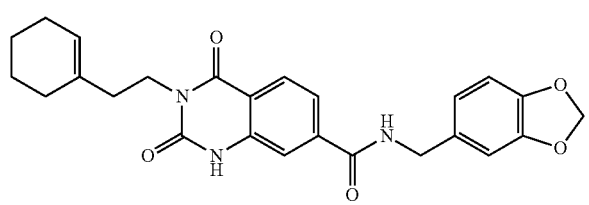
777
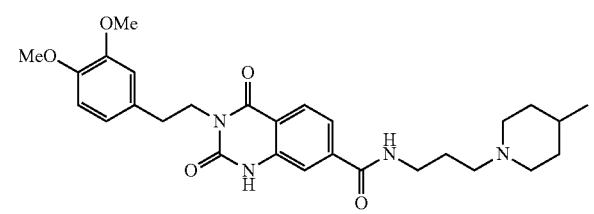
779
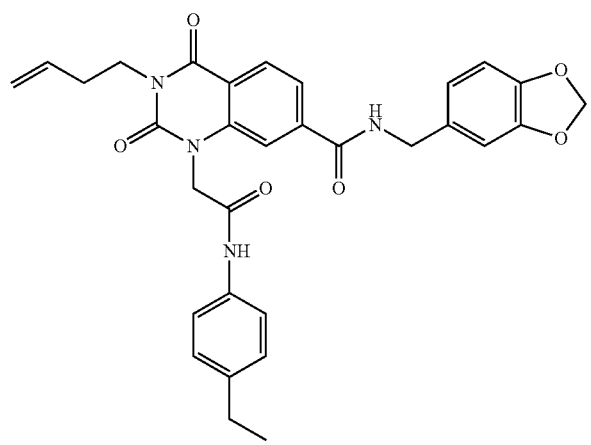
781
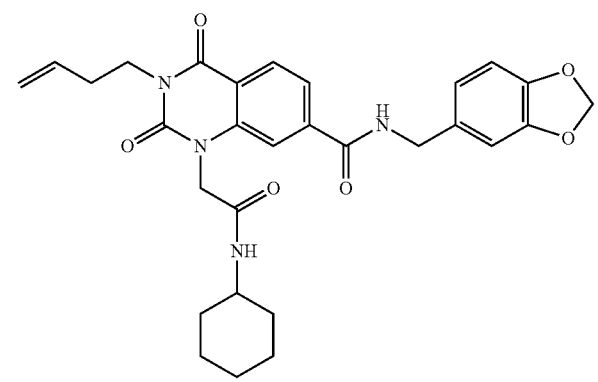
783
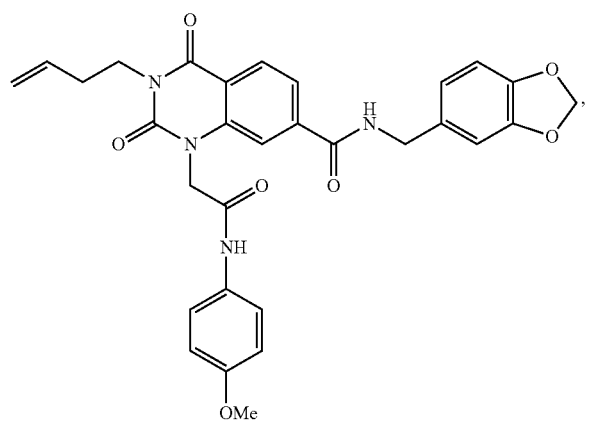
785
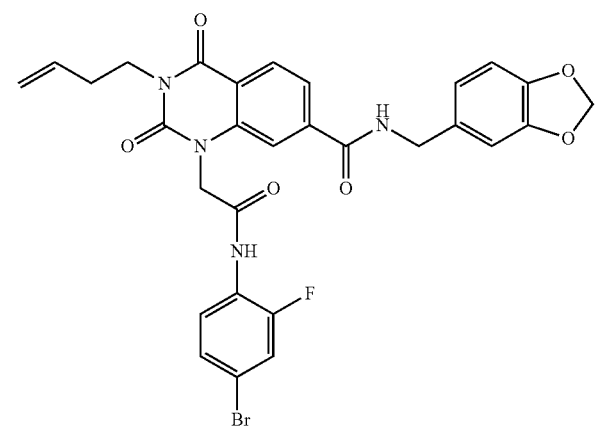

-continued
787
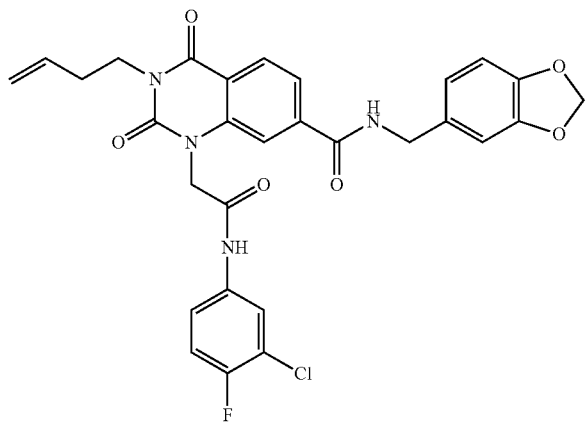
789
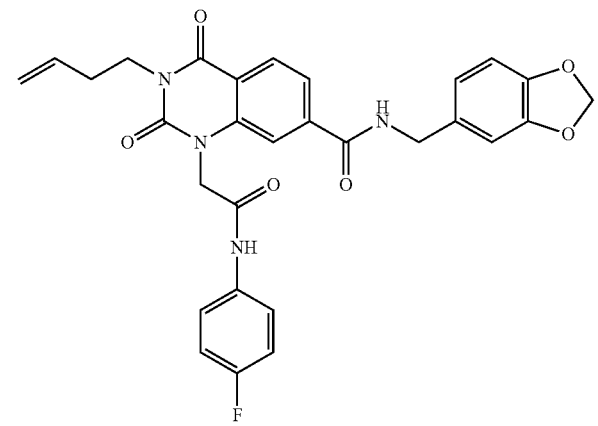
791
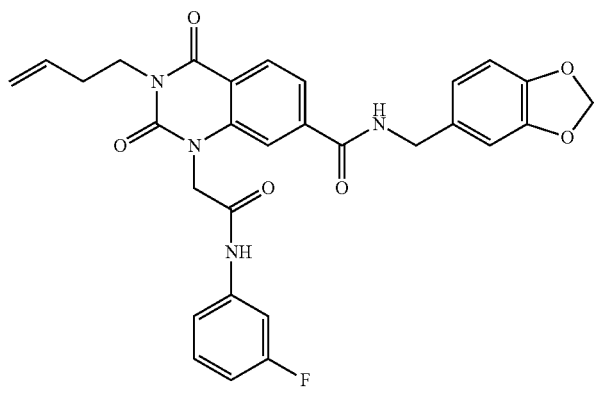
793
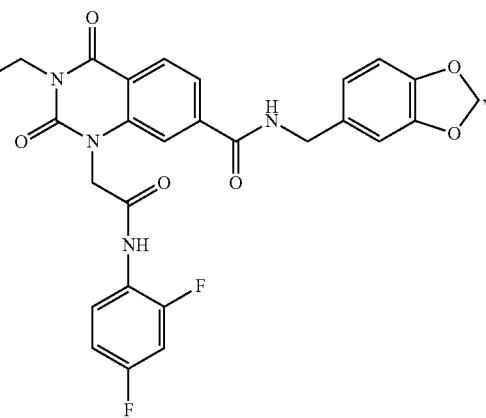
795
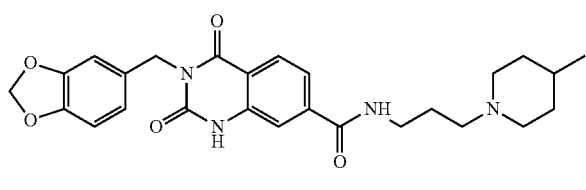
797
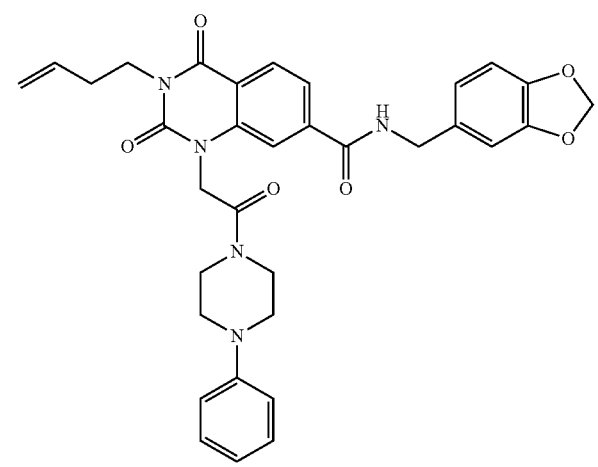
799
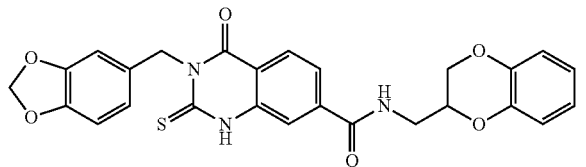
801
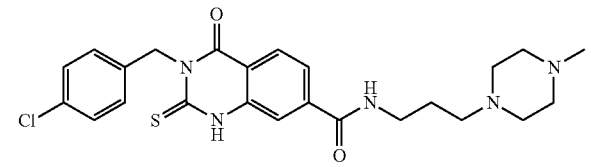

-continued

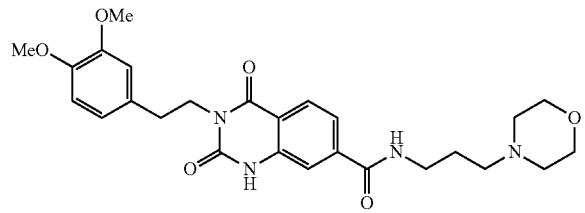
803

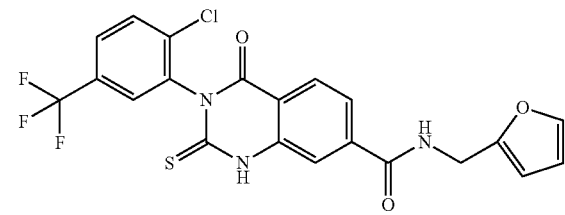
805

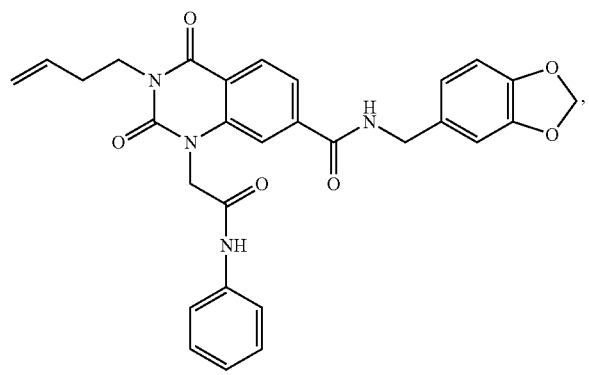
807

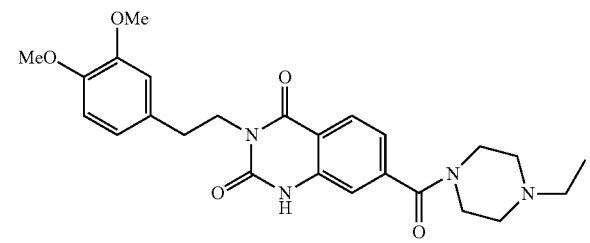
809 or a salt, solvate, or physiologically functional derivative thereof.

In another aspect, the present invention provides a compound having structural Formula (XVII):

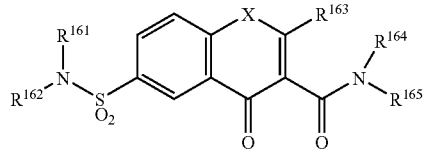

(XVII)

or a salt, solvate, or physiologically functional derivative thereof;

wherein: X is $SO_2$, $C(=O)$ or $NR^{166}$;

$R^{161}$ and $R^{162}$ are independently hydrogen, alkyl, substituted alkyl, aryl, substituted aryl, heteroaryl, substituted heteroaryl, cycloheteroalkyl or substituted cycloheteroalkyl;

$R^{163}$ is hydrogen, alkyl, substituted alkyl, or $NR^{167}R^{168}$;

$R^{164}$ and $R^{165}$ are independently hydrogen, alkyl, substituted alkyl, arylalkyl, substituted arylalkyl, or alternatively, together with the atoms to which they are bonded form a cycloheteroalkyl or substituted cycloheteroalkyl ring;

$R^{166}$ is hydrogen, alkyl, substituted alkyl or amino; and $R^{167}$ and $R^{168}$ are independently hydrogen, alkyl, or substituted alkyl.

In specific embodiments of Formula (XVII), the compound has a structure selected from the group consisting of:

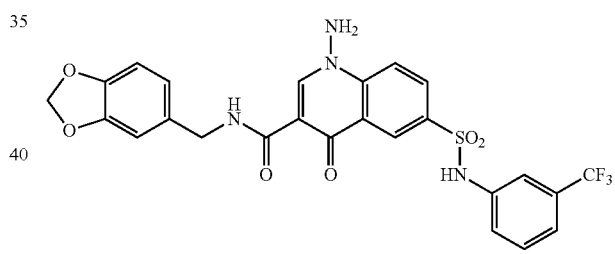
811

813

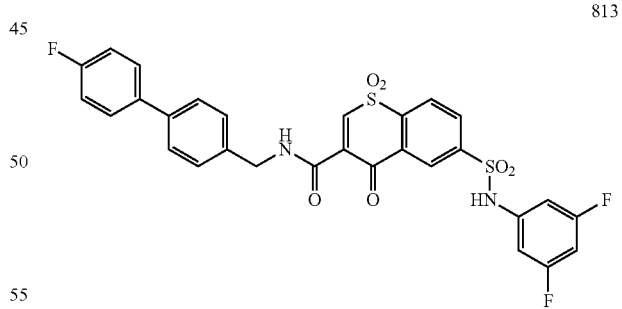
815

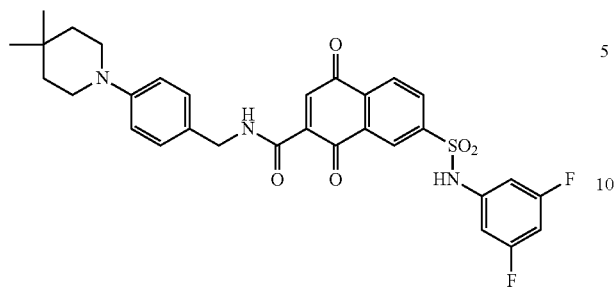
817
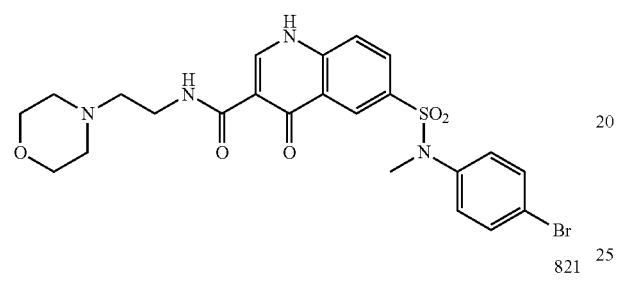
819
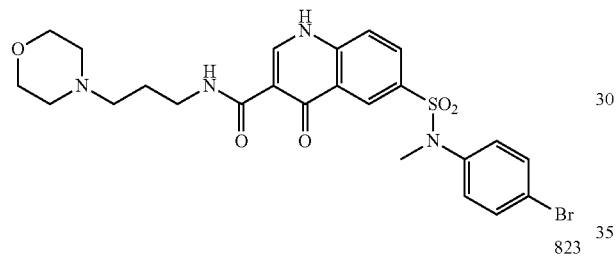
821
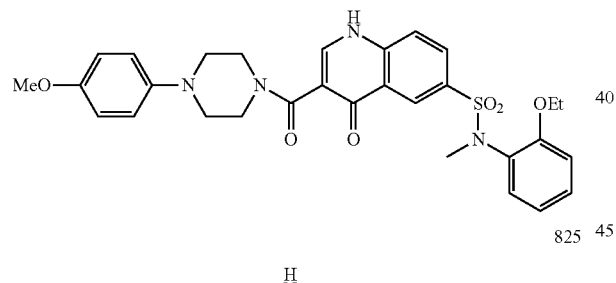
823
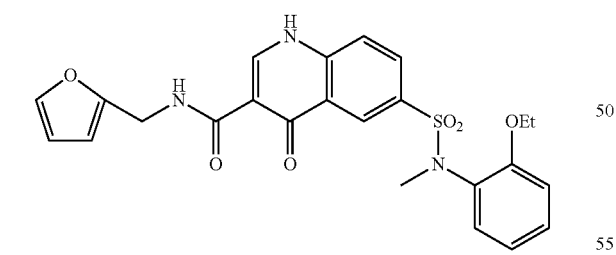
825
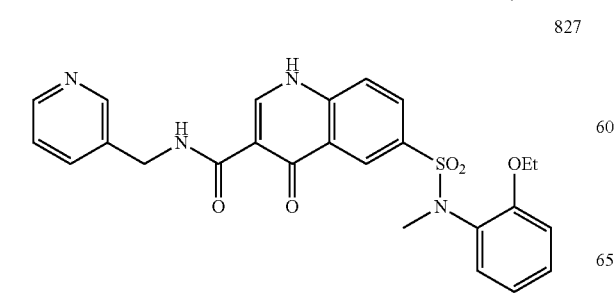
827
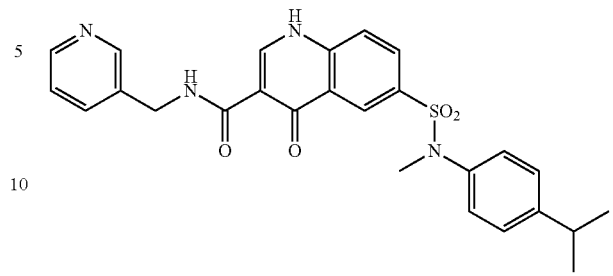
829
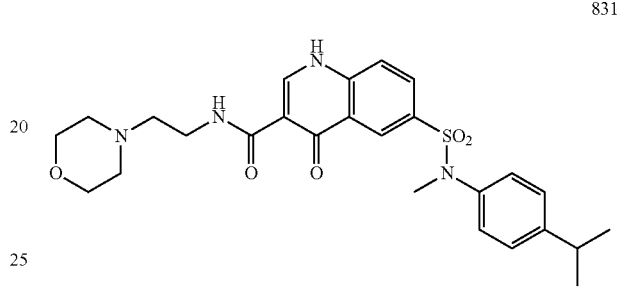
831
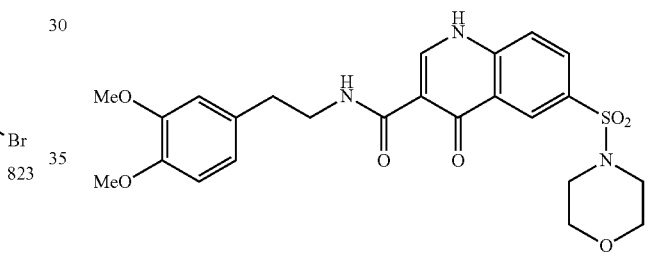
835
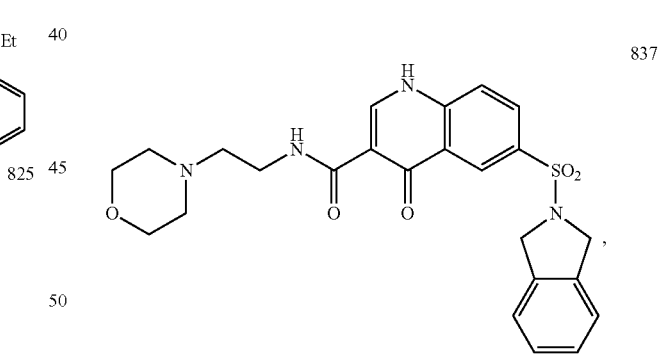
837
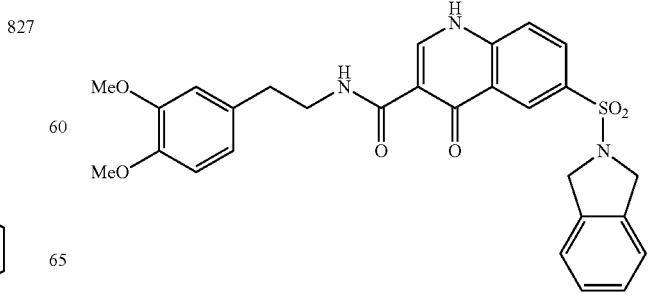
839

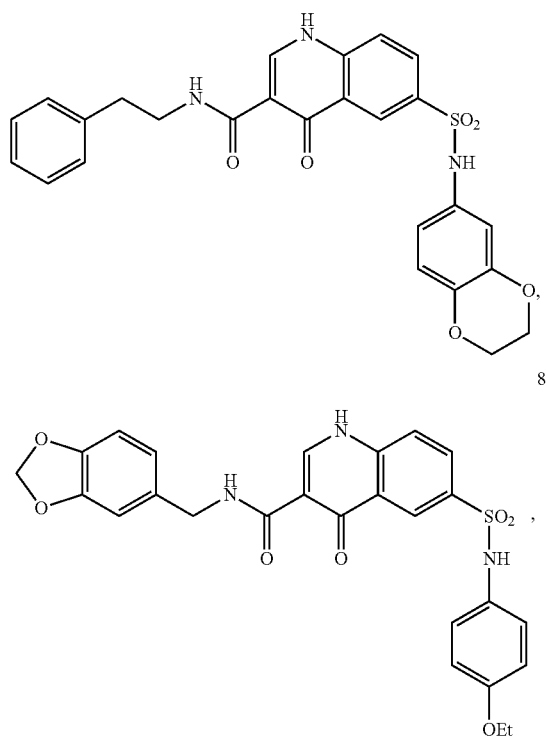
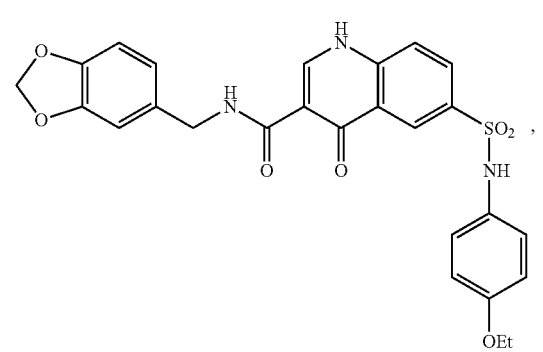
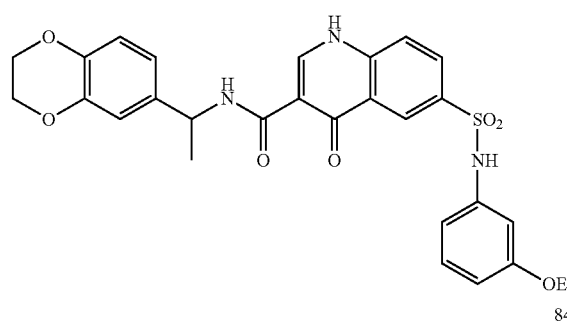
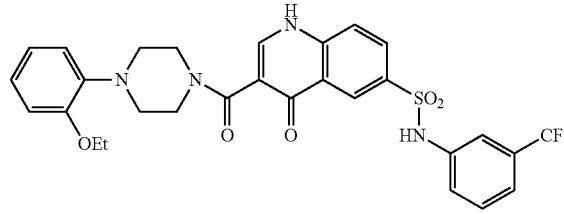
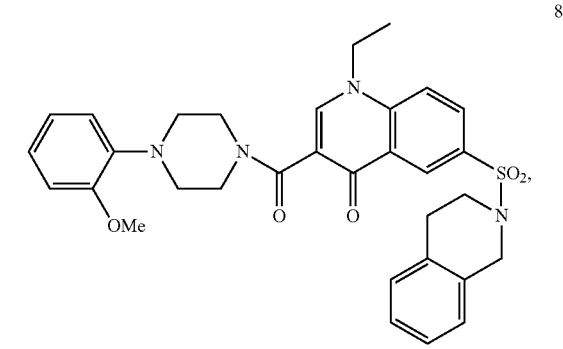
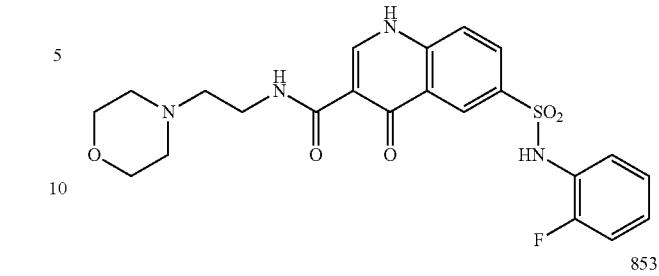

863
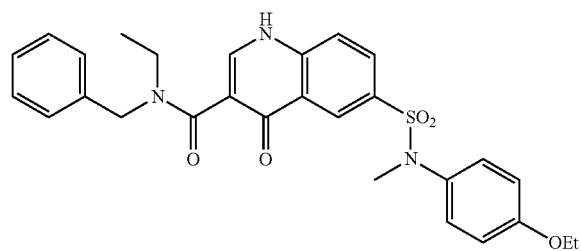
865
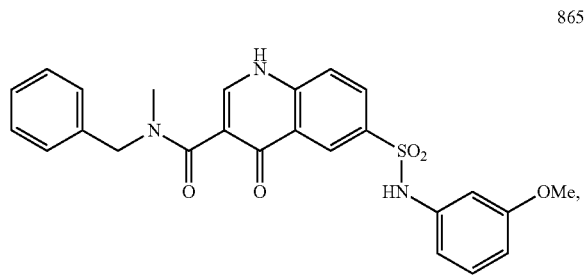
867
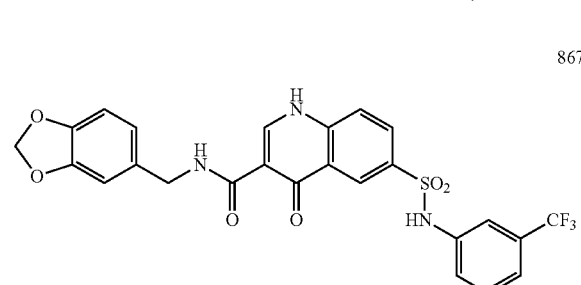
869
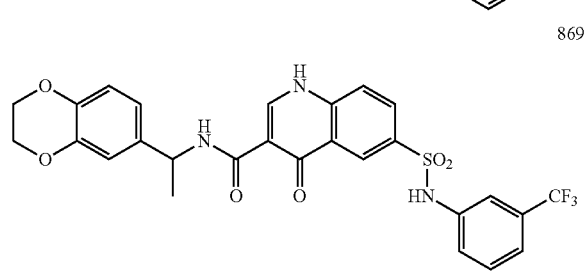
871
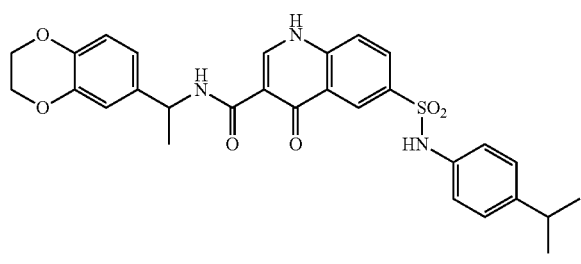
873
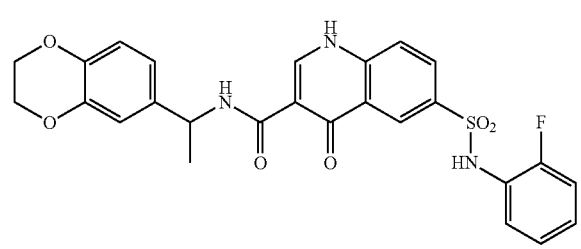
875
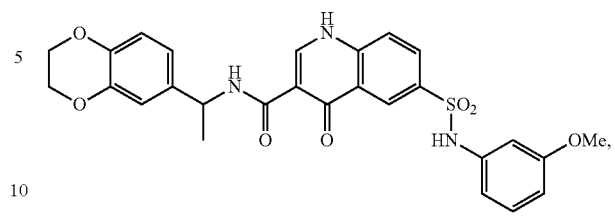
877
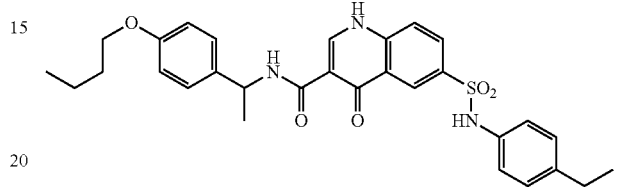
879
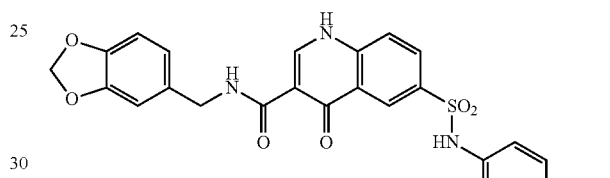
881
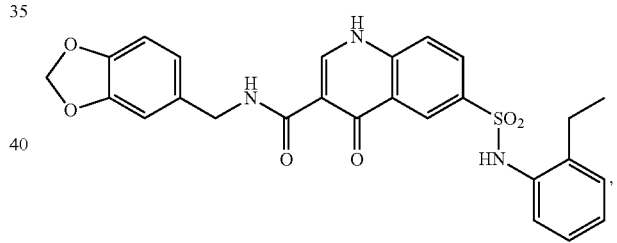
883
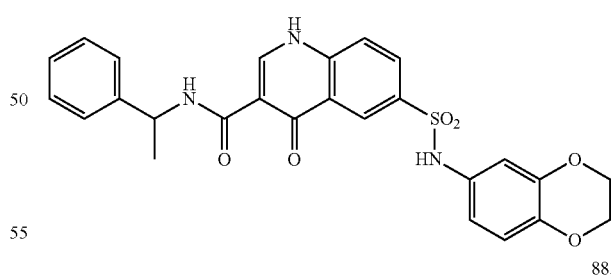
885
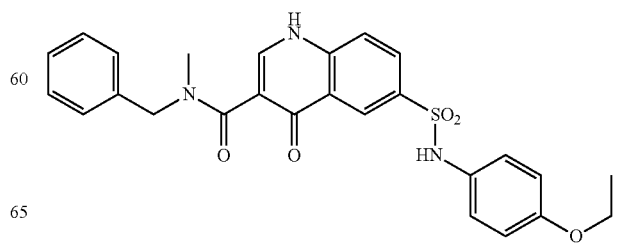

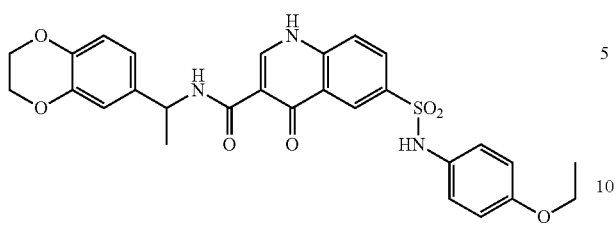

887

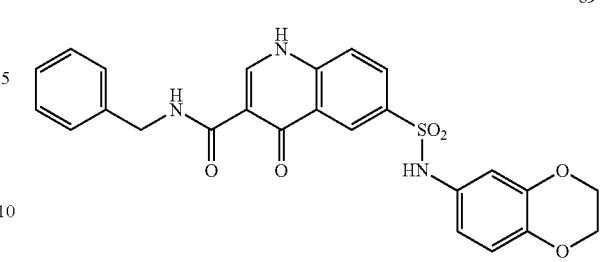

897 or a salt, solvate, or physiologically functional derivative thereof.

In another aspect, the present invention provides a compound having of structure:

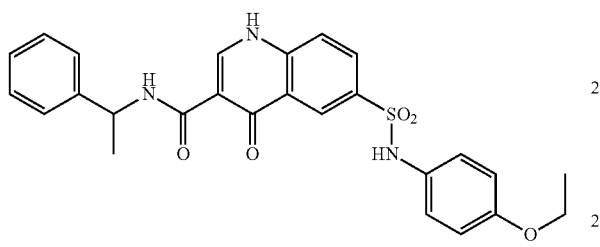

889

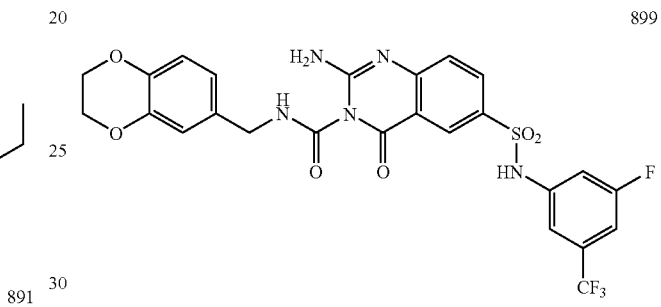

899 or a salt, solvate, or physiologically functional derivative thereof.

In another aspect, the present invention provides a compound having of structural Formula (XVIII):

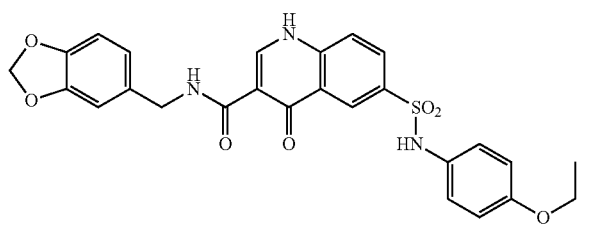

891

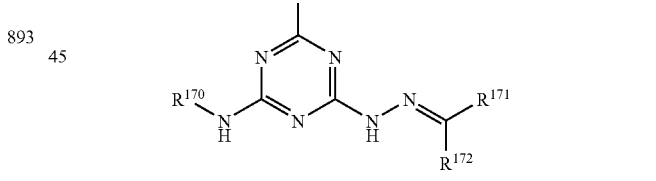

(XVIII)

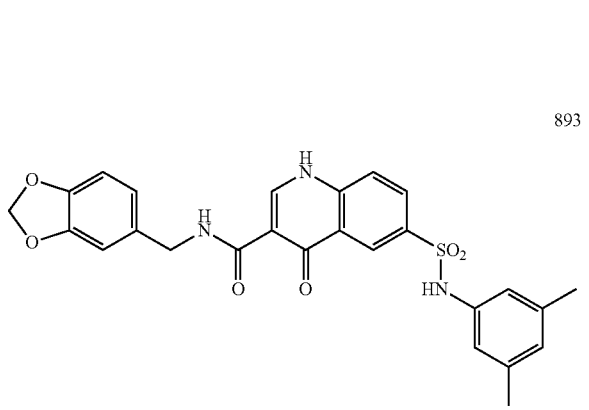

893 or a salt, solvate, or physiologically functional derivative thereof;

wherein: $R^{170}$, $R^{171}$ and $R^{172}$ are independently hydrogen, aryl, substituted aryl, heteroaryl or substituted heteroaryl.

In one embodiment of Formula (XVIII), $R^{170}$ and $R^{171}$ are independently phenyl or substituted phenyl.

In a preferred embodiment of the present invention, the compound of Formula (XVIII) is not 3,4-dibromo-6-ethoxy-2-[(4-morpholin-4-yl-6-phenylamino-[1,3,5]triazin-2-yl)-hydrazonomethyl]-phenol or 4-methyl-3-{4-morpholin-4-yl-6-[N'-(2-nitro-benzylidene)-hydrazino]-[1,3,5]triazin-2-ylamino}-phenol or 4-methyl-3-[(4-morpholin-4-yl-6-{(2E)-2-[(2-nitrophenyl)methylidene]hydrazino}-1,3,5-triazin-2-yl)amino]phenol.

In specific embodiments of Formula (XVIII), the compound has a structure selected from the group consisting of:

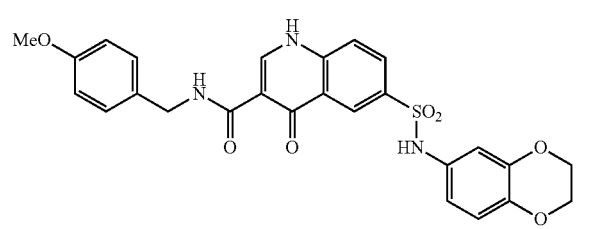

895

103
901
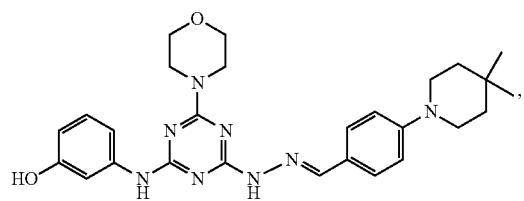
104
903
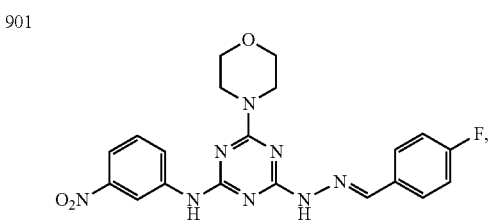
905
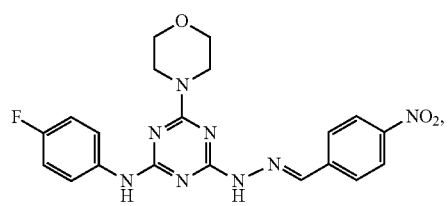
907
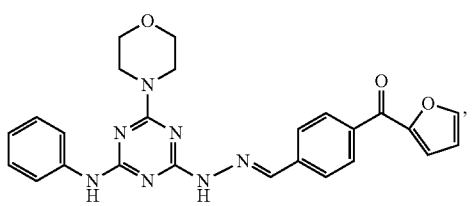
911
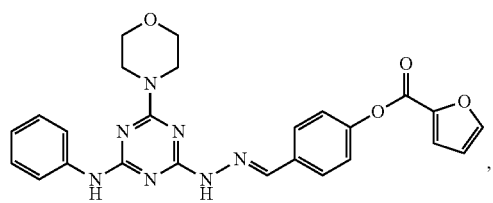
913
917
915
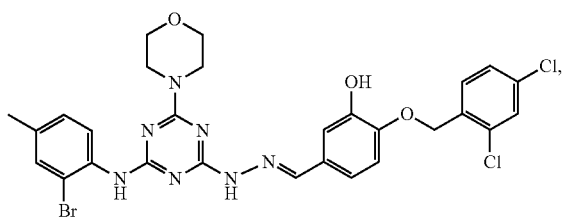
919
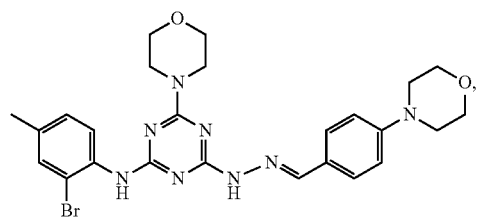
921
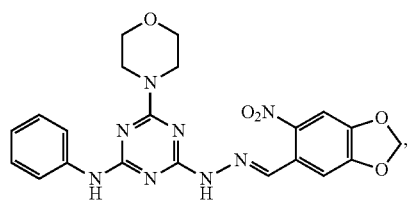
923
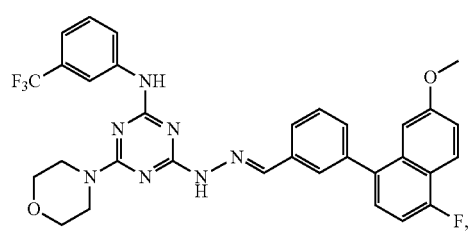
925
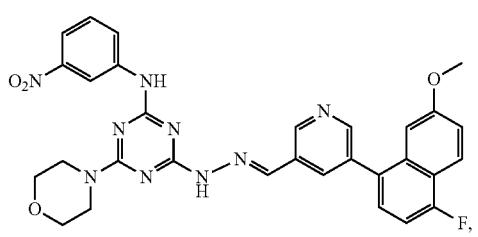

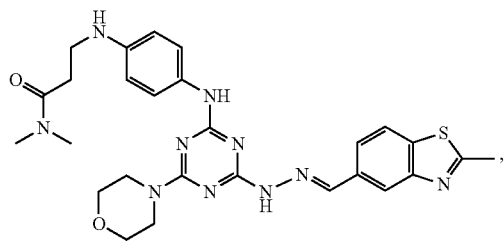
927

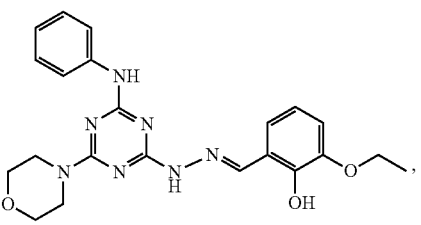
929

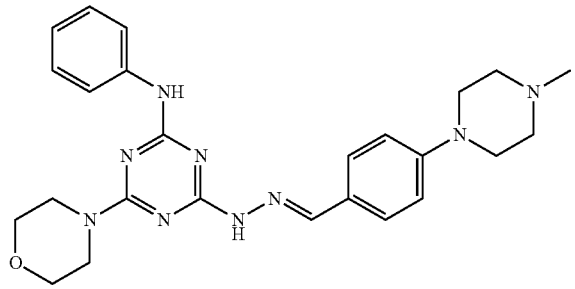
931

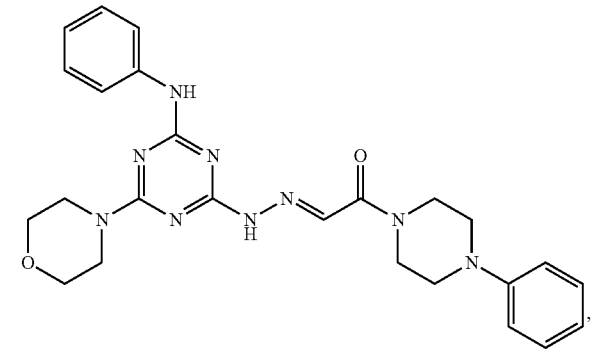
933

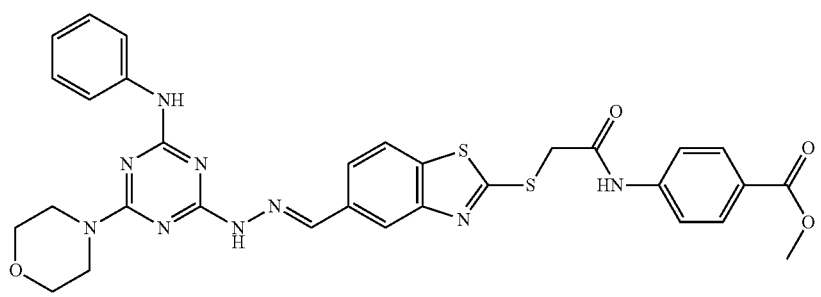
935

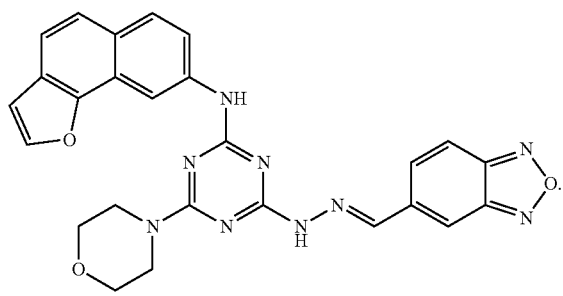
937 or a salt, solvate, or physiologically functional derivative thereof.

6.3 Synthesis of the Compounds

Several methods for preparing the compounds of the present invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; Et₃N: triethylamine; DCM: dichloromethane; DCE: dichloroethane; DME: dimethoxyethane; DBA: diethylamine; DAST: diethylaminosulfur trifluoride; EtMgBr: ethylamgnesium bromide; BSA: bovine serum albumin; TFA: trifluoracetic acid; DMF: N,N-dimethylformamide; SOCl₂: thionyl chloride; CDI: carbonyl diimidazole; rt: room temperature; HPLC: high performance liquid chromatography; TLC: thin-layer chromatography. The compounds described herein may be prepared in a variety of ways known to one skilled in the art.

Some of the compounds described herein can be obtained from commercial sources, such as Aldrich Chemical Co. (Milwaukee, Wis.), Sigma Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.) or can be synthesized. The compounds described herein and other related compounds having different substituents identified by any of the methods described above can be synthesized using techniques and materials known to those of skill in the art, such as described, for example, in March, ADVANCED ORGANIC CHEMISTRY 4.sup.th Ed., (Wiley 1992); Carey and Sundberg, ADVANCED ORGANIC CHEMISTRY 3.sup.rd Ed., Vols. A and B (Plenum 1992), and Green and Wuts, PROTECTIVE GROUPS IN ORGANIC SYNTHESIS 2.sup.nd Ed. (Wiley 1991). Starting materials useful for preparing compounds described herein or intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

The procedures described herein for synthesizing the present compounds may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Compounds represented by Formula I, for example, can be generally synthesized according to Schemes Ia and Ib (Scheme Ia is based on Radeva et al., *Russ. J. Org. Chem.* 41 (2005) 6, 907-909). The $R^1$ and $R^2$ are defined same as the $R^1$ and $R^5$ in formula I unless otherwise noted below. Apparently enough to those skilled in the art, protection and deprotection steps as well as their orders will be arranged based on the nature of $R^1$ and $R^2$.

Scheme Ia:

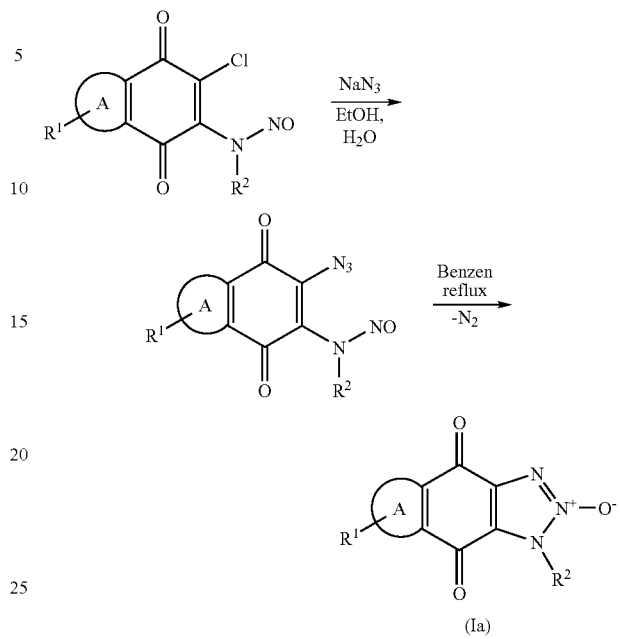

Example for Scheme Ia:

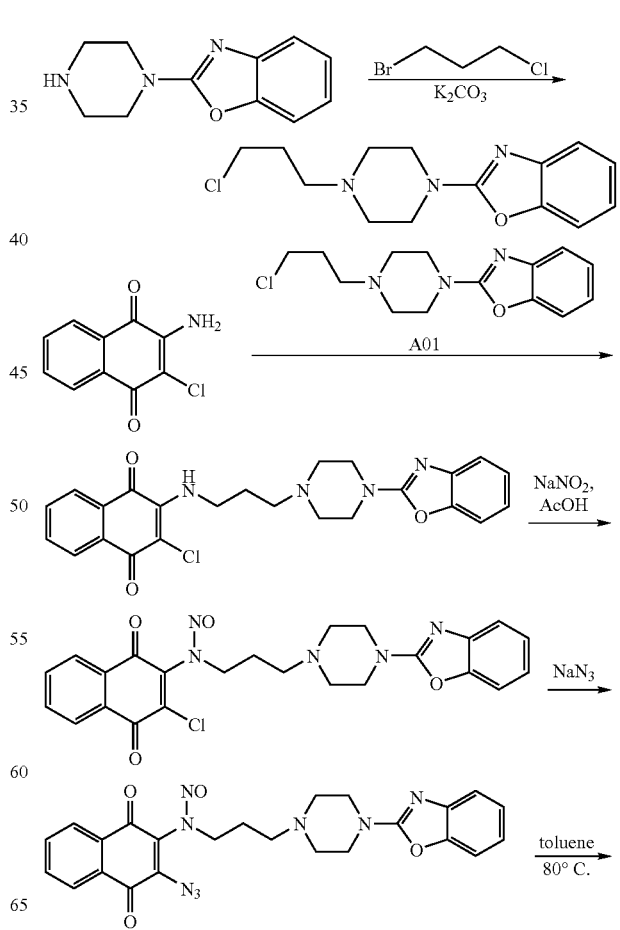

-continued

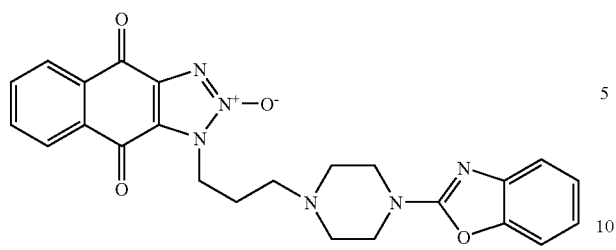

Scheme Ib:

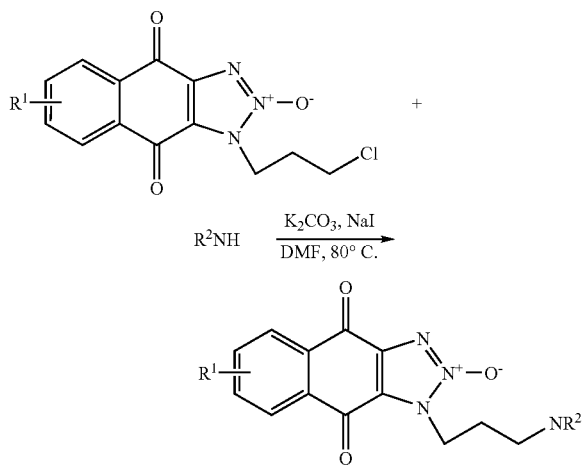

Compounds represented by Formula I, for example, can be generally synthesized according to Scheme Ic (based on WO00/05194).

Scheme Ic:

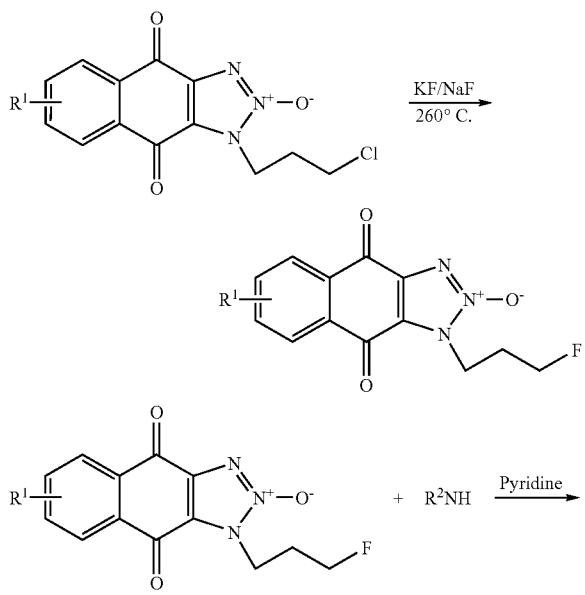

-continued

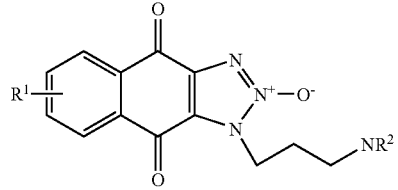

Compounds represented by Formula III, in another example, can be generally synthesized according to Scheme IIa (modified from Hay et al., *J. Med. Chem.* (2007) 50, 6292-6404).

Scheme IIa:

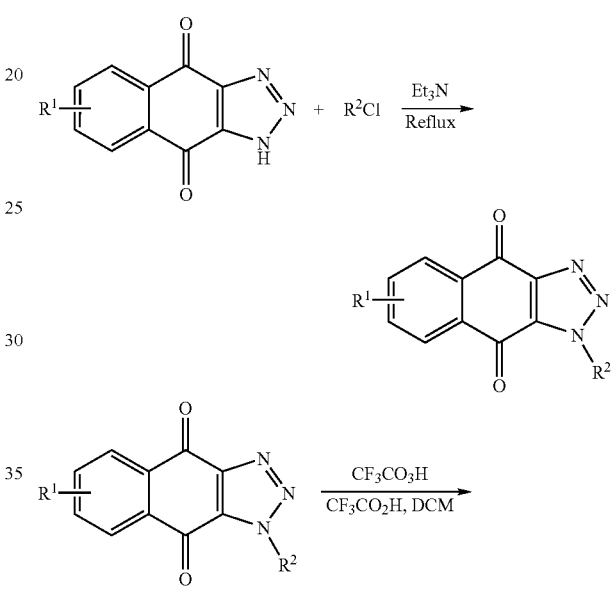

Compounds represented by Formula VI can be generally synthesized according to Scheme IIIa and IIIg (based on Yang et al., CN200510055351).

Scheme IIIa:

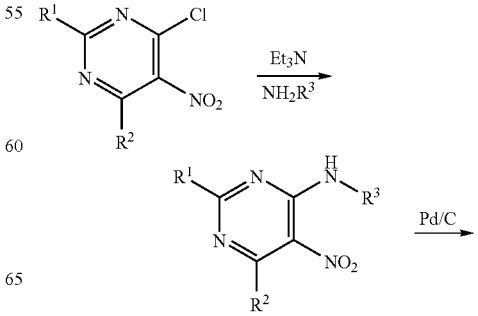

-continued

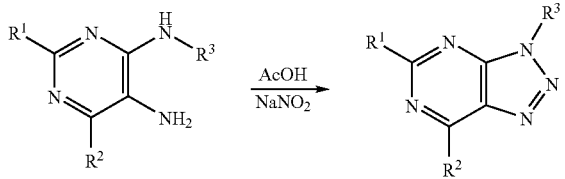

Scheme IIIb:

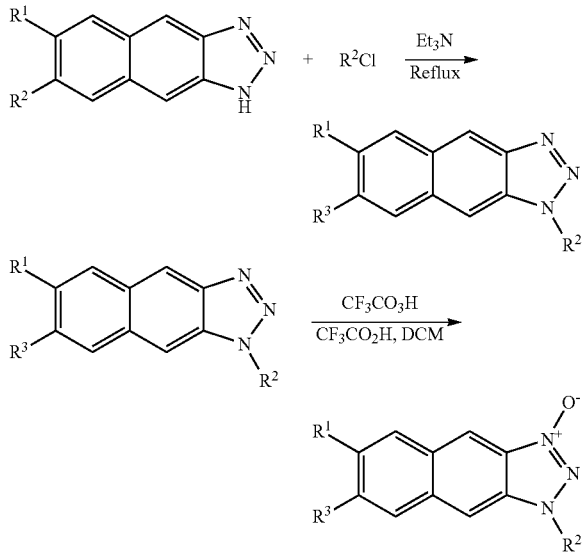

In scheme IVa, the second N⁺—O⁻ group in one example of the present compounds was generated through Davis reagent.

Scheme IVa:

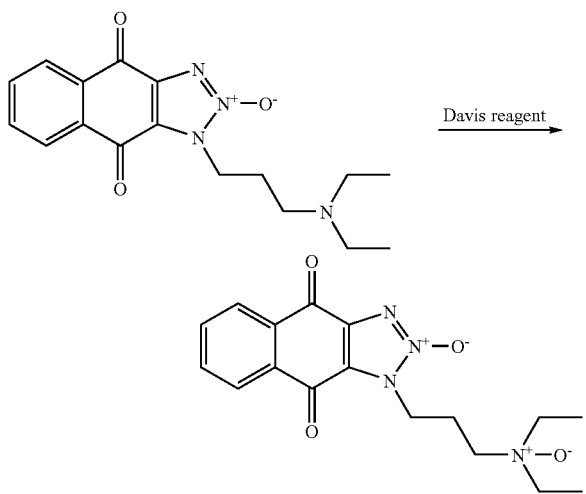

Examples of Spectral Information for the Compounds of the Present Invention:

Compound 101: ¹HNMR (400 MHz, DMSO-d6), ppm: 8.03 (m, 2H), 7.90 (m, 2H), 7.50 (m, 2H), 6.71 (m, 2H), 4.76 (t, 2H), 4.29 (t, 2H), 3.18 (m, 4H), 2.84 (m, 4H), 2.32 (m, 2H).

Compound 103: ¹HNMR (400 MHz, CDCl3), ppm: 8.26 (m, 1H), 8.19 (m, 1H), 7.83 (m, 2H), 4.81 (t, 2H), 4.28 (t, 2H), 4.20-3.40 (m, 3H), 2.80-2.40 (m, 10H), 2.20-1.80 (m, 6H), 1.45 (m, 2H).

Compound 105: ¹HNMR (400 MHz, CDCl3), ppm: 8.30 (m, 1H), 8.21 (m, 1H), 7.85 (m, 2H), 7.48 (m, 1H), 6.98 (m, 1H), 4.86 (t, 2H), 3.68 (m, 4H), 2.57 (m, 2H), 2.42 (m, 4H), 2.15 (m, 2H).

Compound 107: ¹HNMR (400 MHz, CDCl3), ppm: 8.23 (m, 1H), 8.16 (m, 1H), 7.82 (m, 2H), 4.79 (t, 2H), 3.08 (m, 2H), 2.60-2.02 (m, 18H), 1.90-1.70 (m, 4H).

Compound 109: ¹HNMR (400 MHz, CDCl3), ppm: 8.30 (m, 1H), 8.19 (m, 1H), 7.84 (m, 2H), 6.80-6.60 (m, 3H), 5.95 (s, 2H), 4.81 (t, 2H), 3.27 (s, 2H), 2.60-1.80 (m, 12H).

Compound 113: ¹HNMR (400 MHz, DMSO-d6), ppm: 8.74 (s, 1H), 8.24 (m, 1H), 8.17 (m, 1H), 7.99 (m, 1H), 7.82 (m, 2H), 6.51 (d, 1H), 4.83 (t, 2H), 4.31 (q, 2H), 3.51 (m, 4H), 2.55 (t, 2H), 2.43 (m, 4H), 2.15 (m, 2H), 1.35 (t, 3H).

Compound 157: ¹HNMR (400 MHz, CDCl3), ppm: 8.29-8.15 (m, 3H), 7.84 (m, 1H), 7.45 (t, 1H), 6.60 (m, 2H), 4.86 (t, 2H), 3.39 (m, 4H), 2.57 (t, 2H), 2.47 (m, 4H), 2.18 (m, 2H).

Compound 179: ¹HNMR (400 MHz, CDCl3), ppm: 8.24 (m, 2H), 7.84 (m, 2H), 7.02-6.75 (m, 4H), 4.86 (t, 2H), 3.84 (s, 3H), 2.91 (m, 4H), 2.58 (m, 4H), 2.17 (m, 2H).

Compound 235: ¹HNMR (400 MHz, CDCl3), ppm: 8.24 (m, 2H), 7.84 (m, 2H), 7.35 (m, 2H), 6.90 (m, 2H), 4.83 (t, 2H), 3.83 (s, 3H), 3.43 (m, 4H), 2.55 (m, 2H), 2.34 (m, 4H), 2.13 (m, 2H).

Compound 237: ¹HNMR (400 MHz, CDCl3), ppm: 8.29 (m, 1H), 8.27 (m, 1H), 8.07 (d, 1H), 7.83 (m, 2H), 7.60 (d, 1H), 7.00 (d, 1H), 6.83 (d, 1H), 4.88 (t, 2H), 4.28 (t, 2H), 3.70 (m, 4H), 3.66 (m, 4H), 2.36 (m, 2H).

Compound 239: ¹HNMR (400 MHz, CDCl3), ppm: 8.29 (m, 1H), 8.15-8.21 (m, 2H), 7.87 (m, 2H), 6.63 (m, 1H), 6.60 (m, 1H), 4.88 (t, 2H), 4.28 (t, 2H), 3.62 (m, 4H), 3.52 (m, 4H), 2.64 (s, 1H), 2.38 (m, 2H).

Compound 241: ¹HNMR (400 MHz, CDCl3), ppm: 8.27 (m, 1H), 8.15 (m, 1H), 7.82 (m, 2H), 7.38 (d, 1H), 7.26 (d, 1H), 7.20 (t, 1H), 7.06 (t, 1H), 4.876 (t, 2H), 4.25 (t, 2H), 3.74 (m, 4H), 3.62 (m, 4H), 2.35 (m, 2H).

Compound 245: ¹HNMR (400 MHz, CDCl3), ppm: 8.25 (m, 2H), 8.02 (m, 1H), 7.85 (m, 2H), 6.39 (m, 1H), 6.25 (m, 1H), 4.87 (t, 2H), 3.91 (m, 4H), 3.24 (m, 4H), 3.07 (m, 4H), 2.60 (t, 4H), 2.51 (m, 4H), 2.17 (m, 2H).

Compound 247: ¹HNMR (400 MHz, CDCl3), ppm: 8.20 (m, 2H), 7.82 (m, 2H), 7.77 (d, 1H), 6.17 (dd, 1H), 6.01 (m, 1H), 4.83 (t, 2H), 3.19 (m, 8H), 2.57 (m, 2H), 2.41 (m, 4H), 2.15 (m, 2H), 1.97 (m, 4H).

Compound 249: ¹HNMR (400 MHz, CDCl3), ppm: 8.23 (m, 2H), 7.90 (m, 2H), 7.84 (m, 2H), 6.78 (m, 2H), 4.86 (t, 2H), 3.88 (s, 3H), 3.21 (m, 4H), 2.60 (m, 2H), 2.54 (m, 4H), 2.18 (m, 2H), Compound 297: ¹HNMR (400 MHz, CDCl3), ppm: 8.25 (m, 1H), 8.15 (m, 1H), 7.83 (m, 2H), 7.51 (d, 1H), 7.05 (d, 1H), 6.50 (m, 1H), 4.84 (t, 2H), 4.22 (t, 2H), 3.81 (m, 4H), 3.50 (m, 4H), 2.33 (m, 2H).

6.4 Therapeutic Uses

In accordance with the present invention, a compound of the present, invention, or a salt, ester, and/or a prodrug thereof, or a pharmaceutical composition containing the compound, or a salt, ester, and/or a prodrug thereof, is administered to a patient, preferably a human, suffering from an apoptosis associated disease for medical treatment purpose. The present compounds may also be used to treat cells in which the cell death signal is down-regulated and the affected cell has an inappropriately diminished propensity for cell death.

In some embodiments, the apoptosis associated disease is cancer. For example, the cancer can be of the skin, breast, brain, cervical carcinomas, testicular carcinomas, and the like. More particularly, the cancers that can be treated by using the present compounds include, but are not limited to, cancers of the following organs or systems: skin, breast, brain, cervix, testis, cardiac, lung, gastrointestinal, genitourinary tract, liver, bone, nervous system, gynecological, hematologic, and adrenal glands.

In some embodiments, the cancer is characterized by over-expression of a Bcl-2 family member. In some embodiments, the cancer is characterized by hypoxia. In some embodiments, the cancer includes solid tumors or leukemias. In some embodiments, the cancer includes gliomas (Schwannoma, glioblastoma, astrocytoma), neuroblastoma, pheochromocytoma, paraganlioma, meningioma, adrenal cortical carcinoma, kidney cancer, vascular cancer of various types, osteoblastic osteocarcoma, prostate cancer, ovarian cancer, uterine leiomyomas, salivary gland cancer, choroid plexus carcinoma, mammary cancer, pancreatic cancer, colon cancer, B and T cell lymphomas, acute and chronic myeloid or lymphoid leukemias, and multiple myeloma.

Furthermore, the present compounds or salts, esters, and/or prodrugs can be used for the treatment of pre-malignant conditions associated with any of the above-mentioned cancers (e.g., colon adenomas, myelodysplastic syndrome).

In other embodiments, the present compounds may be used to treat a neurodegenerative disease characterized by the over-expression of a pro-apoptotic Bcl-2 family member. The neurodegenerative diseases include, but are not limited to, Alzheimer's disease, Parkinson's disease, amyotrophic lateral sclerosis, multiple sclerosis and other diseases linked to degeneration of the brain, such as Creutzfeldt-Jakob disease and expanded polyglutamine repeat diseases such as, for example, Huntington's disease, dentatorubral pallidoluysian atrophy, spinobulbar muscular atrophy, and spinocerebellar ataxia types 1, 2, 3, 6 and 7 (Burke et al., U.S. Pat. No. 6,632,616).

In still other embodiments, the present compounds or salts, esters, and/or prodrugs may be used to treat arthritis, inflammation, autoimmune diseases, human immunodeficiency virus (HIV) immunodeficiency syndrome, myelodysplastic syndromes (such as aplastic anemia), ischaemic syndromes (such as, for example, myocardial infarction), liver diseases which are induced by toxins (such as, for example, alcohol), alopecia, damage to the skin due to UV light, lichen planus, atrophy of the skin, cataracts, etc.

Specific methods for identifying apoptosis-modulating compounds may be found in U.S, Patent Application Nos. US006165732 and US 007217534 or PCT Application No. PCT/US00/22891, the content of which is herein incorporated by reference in their entirety for all purposes. Active compounds can also be identified by evaluating the ability of the agents to modulate glucose uptake and/or lactate production in cells expressing an anti-apoptotic Bcl-2 family member protein. Apoptosis-modulating compounds increase cellular glucose uptake or lactate production in proportion to the level of expression of a Bcl-2 family member target protein. Methods for assaying glucose production or lactate production are well-known in the art.

6.5 Therapeutic/Prophylactic Administration

The present compounds, or a salt, solvate, or physiologically functional derivative thereof; or pharmaceutical compositions containing the present compounds, or salts, solvates, or physiologically functional derivatives thereof, may be advantageously used in human medicine. As previously described in Section 6.4 above, the present compounds are useful for the treatment or prevention of various diseases characterized by regulation of apoptosis.

When used to treat or prevent the above-mentioned diseases or disorders, the present compounds may be administered or applied solely, or in combination with other active agents (e.g., other anti-cancer agents, other anti-viral agents, etc.).

The present invention provides methods of treatment and prophylaxis by administration to a patient in need of such treatment a therapeutically effective amount of one or more compounds of the present invention, or a salt, solvate, or physiologically functional derivative thereof.

The patient may be an animal, more preferably, a mammal and most preferably, a human.

The present compounds, or a salt, solvate, or physiologically functional derivative thereof, may be administered orally. The present compounds, or a salt, solvate, or physiologically functional derivative thereof, may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition thereof. Methods of administration include, but are not limited to, intradermal, intramuscular, intraperitoneal, intravenous, subcutaneous, intranasal, epidural, oral, parenteral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the present compounds, or salts, solvates, or physiologically functional derivatives thereof, into the bloodstream of a patient.

In specific embodiments, it may be desirable to administer one or more of the present compounds, or salts, solvates, or physiologically functional derivatives thereof, locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, administration can be accomplished by direct injection at the site (or former site) of cancer or arthritis.

In certain embodiments, it may be desirable to introduce one or more the present compounds, or salts, solvates, or physiologically functional derivatives thereof, into the central nervous system of a patient by any suitable route, including intraventricular, intrathecal and epidural injection. Intraventricular injection may be facilitated by an intraventricular catheter, for example, attached to a reservoir, such as an Ommaya reservoir.

The present compounds, or salts, solvates, or physiologically functional derivatives thereof, may also be administered directly to the lung by inhalation. For administration by inhalation, the present compounds, or salts, solvates, or physiologically functional derivatives thereof, may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas), may be used to deliver compounds of the present invention directly to the lung.

Alternatively, a Dry Powder Inhaler ("DPI") device may be used to administer the present compounds, or salts, solvates, or physiologically functional derivatives thereof, to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the invention and a suitable powder base such as lactose or starch for these systems.

Another type of device that may be used to deliver the present compounds, or salts, solvates, or physiologically functional derivatives thereof, to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer is used to deliver the present compounds, or salts, solvates, or physiologically functional derivatives thereof, to the lung. Nebulizers create aerosols from liquid drug formulations by using; for example, ultrasonic energy to form fine particles that may be readily inhaled (see e.g., Verschoyle et al., *British J. Cancer,* 1999, 80, Suppl. 2, 96. Nebulizers are available from a number of commercial sources such as Sheffield/Systemic Pulmonary Delivery Ltd. Aventis and Batelle Pulmonary Therapeutics.

In other embodiments, an electrohydrodynamic ("EHD") aerosol device is used to deliver the present compounds, or salts, solvates, or physiologically functional derivatives thereof, to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering the present compounds, or salts, solvates, or physiologically functional derivatives thereof, to the lung with an EHD aerosol device and such optimization is routinely performed by one of skill in the art. EHD aerosol devices may more efficiently deliver drugs to the lung than existing pulmonary delivery technologies.

In other embodiments, the present compounds, or salts, solvates, or physiologically functional derivatives thereof, can be delivered in a vesicle, in particular a liposome (See, Langer, 1990, *Science,* 249:1527-1533; Treat et al., in "Liposomes in the Therapy of Infectious Disease and Cancer," Lopez-Berestein and Fidler (eds.), Liss, New York, pp. 353-365 (1989); see generally "Liposomes in the Therapy of Infectious Disease and Cancer," Lopez-Berestein and Fidler (eds.), Liss, New York, pp. 353-365 (1989)).

In other embodiments, the present compounds, or salts, solvates, or physiologically functional derivatives thereof, can be delivered via sustained release systems. In still other embodiments, the sustained release system is an oral sustained release systems. In still other embodiments, a pump may be used (See, Langer, supra; Sefton, 1987, *CRC Crit. Ref Biomed Eng.* 14:201; Saudek et al., 1989, *N. Engl. J Med.* 321:574).

In still other embodiments, polymeric materials can be used in the pharmaceutical compositions containing the present compounds, or salts, solvates, or physiologically functional derivatives thereof. (for exemplary polymeric materials, see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for sustained release delivery of oral pharmaceutical compositions. Exemplary polymers include, but are not limited to, sodium carboxymethylcellulose, hydroxypropylcellulose, hydroxypropylmethylcellulose and hydroxyethylcellulose (most preferred, hydroxypropyl methylcellulose). Other cellulose ethers have been described (Alderman, *Int. J. Pharm. Tech. & Prod. Mfr.,* 1984, 5(3) 1-9). Factors affecting drug release are well known to the skilled artisan and have been described in the art (Bamba et al., *Int. J. Pharm.,* 1979, 2, 307).

In other embodiments, enteric-coated preparations can be used for oral sustained release administration. Coating materials include, but are not limited to, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.,* 2000, 26:695-708). In still other embodiments, OROS™ osmotic devices are used for oral sustained release delivery devices (Theeuwes et al., U.S. Pat. No. 3,845,770; Theeuwes et al., U.S. Pat. No. 3,916,899).

In still other embodiments, a controlled-release system can be placed in proximity of the target of the present compounds, or salts, solvates, or physiologically functional derivatives thereof, thus requiring only a fraction of the systemic dose (See, e.g., Goodson, in "Medical Applications of Controlled Release," supra, vol. 2, pp. 115-138 (1984)). Other controlled-release systems discussed in Langer, 1990, *Science* 249:1527-1533 may also be used.

6.6 Pharmaceutical Compositions of the Invention

The present pharmaceutical compositions contain a therapeutically effective amount of one or more compounds of the present invention, or salts, solvates, or physiologically functional derivatives thereof, preferably in purified form, together with a suitable amount of a pharmaceutically acceptable vehicle, so as to provide a form for proper administration to a patient. When administered to a patient, the present compounds and the pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration a compound may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent such as another anti-cancer agent.

In some embodiments, the present compounds, or salts, solvates, or physiologically functional derivatives thereof, are formulated in accordance with routine procedures as a pharmaceutical composition adapted for intravenous administration to human beings. Typically, compounds for intravenous administration are solutions in sterile isotonic aqueous buffer. For injection, the present compounds, or salts, solvates, or physiologically functional derivatives thereof, may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the present compounds, or salts, solvates, or physiologically functional derivatives thereof, are administered by infusion, it can be dispensed, for example, with an infusion bottle containing sterile pharmaceutical grade water or saline. When the present compounds, or salts, solvates, or physiologically functional derivatives thereof, are administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The present compounds, or salts, solvates, or physiologically functional derivatives thereof, may also be formulated in rectal or vaginal pharmaceutical compositions such as suppositories or retention enemas, e.g., containing conventional suppository bases such as cocoa butter or other glycerides.

In addition to the formulations described previously, the present compounds, or salts, solvates, or physiologically functional derivatives thereof, may also be formulated as a depot preparation. Such long acting formulations may be administered by implantation (for example, subcutaneously or intramuscularly) or by intramuscular injection. Thus, for example, the present compounds, or salts, solvates, or physiologically functional derivatives thereof, may be formulated with suitable polymeric or hydrophobic materials (for example, as an emulsion in an acceptable oil) or ion exchange resins, or as sparingly soluble derivatives, for example, as a sparingly soluble salt.

6.7 Therapeutic Doses

The present compounds, or salts, solvates, or physiologically functional derivatives thereof, will generally be used in an amount effective to achieve the intended purpose. For use to treat or prevent diseases or disorders characterized by down regulated apoptosis the compounds and/or pharmaceutical compositions thereof, are administered or applied in a therapeutically effective amount.

The amount of the present compounds, or salts, solvates, or physiologically functional derivatives thereof, that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of the present compounds, or salts, solvates, or physiologically functional derivatives thereof, administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the present compounds, or salts, solvates, or physiologically functional derivatives thereof, are delivered by oral sustained release administration. Dosing may be repeated intermittently, may be provided alone or in combination with other drugs and may continue as long as required for effective treatment of the disease state or disorder.

Suitable dosage ranges for oral administration depend on the potency of the present compounds, but are generally between about 0.001 mg to about 200 mg of a compound of the invention per kilogram body weight. Dosage ranges may be readily determined by methods known to the artisan of ordinary skill.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

The present compounds, or salts, solvates, or physiologically functional derivatives thereof, are preferably assayed in vitro and in vivo, for the desired therapeutic or prophylactic activity, prior to use in humans. For example, in vitro assays can be used to determine whether administration of a specific compound of the invention or a combination of compounds is preferred for inducing apoptosis in cells which over-express bcl-2 proteins. The present compounds, or salts, solvates, or physiologically functional derivatives thereof, may also be demonstrated to be effective and safe using animal model systems.

Preferably, a therapeutically effective dose of the present compounds, or salts, solvates, or physiologically functional derivatives thereof, will provide therapeutic benefit without causing substantial toxicity. Toxicity of the present compounds, or salts, solvates, or physiologically functional derivatives thereof, may be determined using standard pharmaceutical procedures and may be readily ascertained by the skilled artisan. The dose ratio between toxic and therapeutic effect is the therapeutic index. The present compounds, or salts, solvates, or physiologically functional derivatives thereof, generally exhibit particularly high therapeutic indices in treating apoptosis associated disease and disorders. The dosage of the present compounds, or salts, solvates, or physiologically functional derivatives thereof, will preferably be within a range of circulating concentrations that include an effective dose with little or no toxicity.

6.8 Combination Therapy

In certain embodiments of the present invention, the present compounds, or salts, solvates, or physiologically functional derivatives thereof, can be used in combination therapy with at least one additional active or therapeutic agent. The present compounds, or salts, solvates, or physiologically functional derivatives thereof, and the at least one additional active or therapeutic agent can act additively or, more preferably, synergistically. In some embodiments, the present compounds, or salts, solvates, or physiologically functional derivatives thereof are administered concurrently, sequentially, or separately with the administration of another therapeutic agent. Exemplary active or chemotherapeutic agents include, but are not limited to, aceglatone, aclarubicin, altretamine, aminoglutethimide; 5-aminogleavulinic acid, amsacrine, anastrozole, ancitabine hydrochloride, 17-1a antibody, antilymphocyte immunoglobulins, antineoplaston a10, asparaginase, pegaspargase, azacitidine, azathioprine, batimastat, benzoporphyrin derivative, bicalutamide, bisantrene hydrochloride, bleomycin sulphate, brequinar sodium, broxuridine, busulphan, campath-ih, caracemide, carbetimer, carboplatin, carboquone, carmofur, carmustine, chlorambucil, chlorozotocin, chromomycin, cisplatin, cladribine, *corynebacterium parvum*, cyclophosphamide, cyclosporin, cytarabine, dacarbazine, dactinomycin, daunorubicin hydrochloride, decitabine, diaziquone, dichlorodiethylsulphide, didemnin b., docetaxel, doxifluridine, doxorubicin hychloride, droloxifene, echinomycin, edatrexate, elliptinium, elmustine, enloplatin, enocitabine, epirubicin hydrochloride, estramustine sodium phosphate, etanidazole, ethoglucid, etoposide, fadrozole hydrochloride, fazarabine, fenretinide, floxuridine, fludarabine phosphate, fluorouracil, flutamide, formestane, fotemustine, gallium nitrate, gencitabine, gusperimus, homoharringtonine, hydroxyurea, idarubicin hydrochloride, ifosfamide, ilmofosine, improsulfan tosylate, inolimomab, interleukin-2; irinotecan, jm-216, letrozole, lithium gamolenate, lobaplatin, lomustine, lonidamine, mafosfamide, meiphalan, menogaril, mercaptopurine, methotrexate, methotrexate sodium, miboplatin, miltefosine, misonidazole, mitobronitol, mitoguazone dihydrochloride, mitolactol, mitomycin, mitotane, mitozanetrone hydrochloride, mizoribine, mopidamol, muitlaichilpeptide, muromonab-cd3, mustine hydrochloride, mycophenolic acid, mycophenolate mofetil, nedaplatin, nilutamide, nimustine hydrochloride, oxaliplatin, paclitaxel, pcnu, penostatin, peplomycin sulphate, pipobroman, pirarubicin, piritrexim isethionate, piroxantrone hydrochloride, plicamycin, porfimer sodium, prednimustine, procarbazine hydrochloride, raltitrexed, ranimustine, razoxane, rogletimide, roquinimex, sebriplatin, semustine, sirolimus, sizofuran, sobuzoxane, sodium bromebrate, sparfosic acid, sparfosate sodium, sreptozocin, sulofenur, tacrolimus, tamoxifen, tegafur, teloxantrone hydrochloride, temozolomide, teniposide, testolactone, tetrasodium mesotetraphenylporphine-sulphonate, thioguanine, thioinosine, thiotepa, topotecan, toremifene, treosulfan, trimetrexate, trofosfamide, tumor necrosis factor, ubenimex, uramustine, vinblastine sulphate, vincristine sulphate, vindesine sulphate, vinorelbine tartrate, vorozole, zinostatin, zolimomab aritox, and zorubicin hydrochloride, and the like, either individually or in any combination.

6.9 Biological Experiments

Human tumor cell lines were obtained from the American Type Culture Collection, the National Cancer Institute or from the originator as a kind gift. All cells were grown in RPMI 1640 (Invitrogen) medium containing 10% fetal bovine serum and 2 mM L-glutamine.

MTT Proliferation Assay:

Logarithmically growing cells cultured in T75 flasks (Falcon) were harvested and inoculated into 96 well microtiter plates in 100 µL at plating densities ranging from 2,000 to 5,000 cells/well depending on the doubling time of individual cell lines. After cell inoculation, the microtiter plates are incubated at 37° C., 5% $CO_2$, 95% air and 100% relative humidity for 24 h prior to addition of drug.

After 24 h, one plate of each cell line is developed with MTT (3-4,5-Dimethylthiazol-2-yl)-2,5-diphenyltetrazolium bromide, yellow), which is reduced to purple formazan in the mitochondria of living cells. The solubilization solution dimethyl sulfoxide is added to dissolve the insoluble purple formazan product into a colored solution. The absorbance of this colored solution can be quantified by measuring at a certain wavelength (usually between 500 and 600 nm) by a spectrophotometer. The assay is essentially performed as described by Mosman and Alley et al. (Mosman T. et al, J. Immunol. Meth. 65: 55-63, 1983; and Alley M C, et al, Cancer Research 48: 589-601, 1988). This so-called Day 0 measurement of cell growth represents a measurement of the cell population for each cell line at the time of drug addition. The d0 growth value for each cell line is later deducted from each of the readouts at termination of the experiment. Essentially the final readouts are normalized for baseline growth, which enables us direct deduction of growth inhibition parameters from the graphed data.

The compounds of the present invention were dissolved in DMSO at 20 mM and stored frozen prior to use. At the time of drug addition, an aliquot of frozen concentrate was thawed and diluted to twice the desired final maximum test concentration with complete medium. Further dilutions are made to provide a total of nine drug concentrations plus two controls (one medium only, one vehicle control). Aliquots of 100 µl of these different drug dilutions and control were added to the appropriate microtiter wells already containing 100 µl of medium, resulting in the required final drug concentrations: 10 µM to 100 µM.

Following drug addition, the plates were incubated for an additional 5 days at 37° C., 5% $CO_2$, 95% air, and 100% relative humidity. The assay was terminated by the addition of 50 µl of MTT (5 mg/mL) incubated for 4 hrs 37° C. The supernatant is then discarded, and insoluble formazan extracted from the cells with 150 µl of DMSO as described above. The plates were read at 550 nm using a Synergy™ HT Multi-Detection Microplate Reader and KC4 software (Bio-Tek, Winooski, Vt.). Growth inhibition was assessed as inhibitory concentration 50% ($IC_{50}$) compared to vehicle treated controls.

Two independent experiments were conducted and the $IC_{50}$ concentrations calculated plus/minus standard deviation.

Combination Assays:

For combination studies, $IC_{50}$ (inhibitory concentration 50%) values from MTT data for the individual combination partners were calculated and divided resulting in a drug A versus B ratio. Drugs were then combined at this fixed ratio in 9 concentrations and assayed as described above. The plates were incubated for 5 days at 37° C./5% $CO_2$, stained with MTT and growth parameters deduced. Fractions of affected cells were calculated from the readouts and entered into the Calcusyn program developed by Chou (Chou and Talalay, Adv Enzyme Regul 22 27-55, 1984); combination index values were extracted as effective dose 50 ($ED_{50}$), effective dose 75 ($ED_{75}$) and effective dose 90 ($ED_{90}$). Combination index values that are smaller than 1 are considered synergistic, 1-1.2 are additive and above 1.5 values are antagonistic.

An Example of Xenograft Testing:

In this study, human prostate carcinoma cells DU-145 were cultured and harvested for tumor inoculation. Male BALB/cA nude mice (19-21 g) were inoculated with $5 \times 10^6$ DU-145 tumor cells in 0.2 ml medium at the right flank of the mouse for tumor model development. Nineteen days after the inoculation, mice with well-established tumors ($\sim 100$ mm$^3$) were then randomly assigned into five groups (n=10 mice per group), i.e., the vehicle, low-dose of Compound-A, high-dose of Compound-A, Taxol and the combination of low-dose of Compound with Taxol treatment groups. The vehicle group of mice was treated twice-a-day (BID) with 0.5% CMC-Na and 0.1% Tween 80 (vehicle, p.o.). The low-dose group of mice was treated BID with 25 mg/kg of Compound-A dissolved/suspended in the vehicle, i.p. injection. The high-dose group of mice was treated BID with 75 mg/kg of the Compound-A dissolved/suspended in the vehicle, p.o., by oral gavage. The Taxol group of mice was treated with diluted Paclitaxel injection (Bristol-Myers Squibb), i.p. at a dose of 5 mg/kg five days a week (MTWTF) for two weeks. During the experiment, the implanted tumors were measured by caliper twice a week in a blind fashion. The tumors were measured for the maximum width (X) and length (Y) and the tumor volumes (V) were calculated using the formula: $V=(X^2Y)/2$. The differences in the tumor size between the groups were analyzed for significance using the unpaired two-tailed Student's t-test. $P<0.05$ was considered to be statistically significant. The body weights of the mice were recorded twice a week simultaneously.

The results for the above in vivo human prostate DU-145 tumor xenograft study are given in FIG. 2. Throughout the treatment period, the average body weight of mice was not significantly different among the various groups (FIG. 2B).

The average tumor size of the mice treated with Compound-A, either with 25 mg/kg i.p. injection or 75 mg/kg oral administration was significantly smaller compared to either vehicle-treated group or Taxol-treated group on and after 10 days as shown in FIG. 2A. Furthermore, the Compound-A is synergistic with Taxol in reducing the DU-145 tumor growth as shown by the combination group in FIG. 2A. It is therefore concluded that either oral treatment or i.p. injection of the Compound-A has significantly inhibited human prostate cancer growth in the nude mice.

Anti-Tumor Activities:

The anti-tumor activity of a compound which may be used in the present invention may be determined by these in-vitro or in-vivo assays. In particular, the compounds of aforementioned examples had activity in inhibiting the tumor growth or proliferation in the aforementioned in-vitro assays, generally with an $IC_{50}$ value of less than 20 μM. Preferred compounds within the present invention had activity in inhibiting tumor growth or proliferation in the aforementioned in-vitro assays with an $IC_{50}$ value of less than 5 μM. Further preferred compounds within the present invention had activity in inhibiting tumor growth or proliferation in the aforementioned in-vitro assays with an $IC_{50}$ value of less than 1 μM. For examples, for Compound 101 in SF268 (glioblastoma) tumor cell line, $IC_{50}$=0.33 μM; for Compound 235 in H23 (lung) tumor cell line, $IC_{50}$=0.015 μM; for Compound 105 in H460 (lung) tumor cell line, $IC_{50}$=0.049 μM; and for Compound 107 in MCF-7 (breast) tumor cell line, $IC_{50}$=0.015 μM.

Some examples of a compound of the present invention (Compound-B) in inhibiting tumor growth or proliferation, compared with Abt-737, in the aforementioned in-vitro MTT assays are illustrated in FIGS. 1A, 1B and 1C.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All articles, books, encyclopedia and other reference books, publications, patent applications, and patents cited herein are incorporated by reference in their entirety for all purposes.

We claim:
1. A compound of a structural Formula (III):

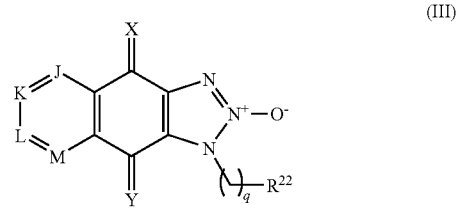

or a salt, solvate, or prodrug thereof;
wherein:
q is 3;
X and Y are O;
J, K, L and M are independently $CR^{25}$ or N;
$R^{22}$ is substituted cycloheteroalkyl comprising a substituent selected from the group consisting of aryl, substituted aryl, alkyl, substituted alkyl, arylalkyl, substituted arylalkyl, cycloalkyldiyl, substituted cycloalkydiyl, cycloheteroalkyldiyl, substituted cycloheteroalkyldiyl, and hydroxyl;
$R^{25}$ is halo, cyano, nitro, hydrogen, $OR^{26}$, $S(O)_t R^{26}$, $CO_2 R^{26}$, $CONR^{26}R^{27}$ or $NR^{26}R^{27}$, alkyl, substituted alkyl, heteroalkyl or substituted heteroalkyl, wherein t is 0, 1, or 2;
each $R^{26}$ and $R^{27}$ are independently hydrogen, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; or alternatively, $R^{26}$ and $R^{27}$, taken together with the atoms to which they are bonded, form a cycloheteroalkyl or substituted cycloheteroalkyl ring; and
with the proviso that Formula (III) does not include 1-[3-(1,4-dioxa-8-azaspiro[4.5]dec-8-yl)propyl]-1H-naphtho[2,3-d][1,2,3]triazole-4,9-dione 2-oxide.

2. A compound, which is selected from the group consisting of:

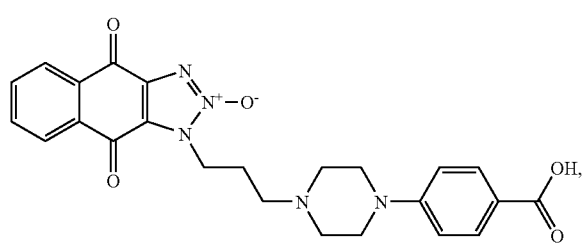

101

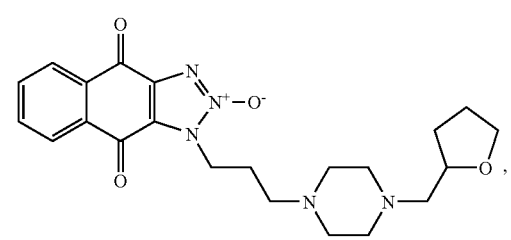

103

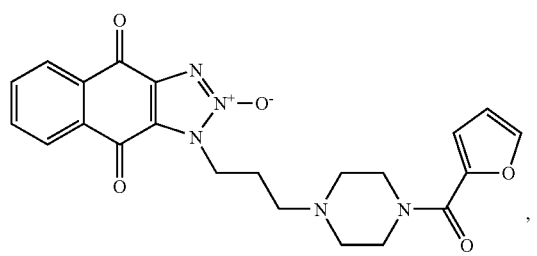

105

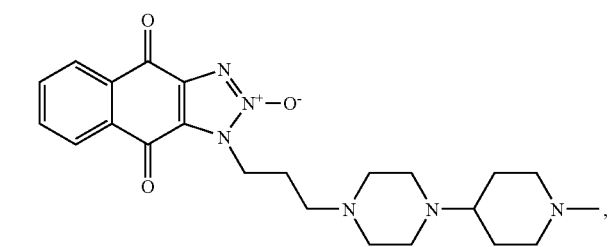

107

-continued
109
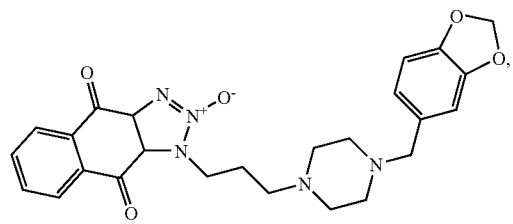
111
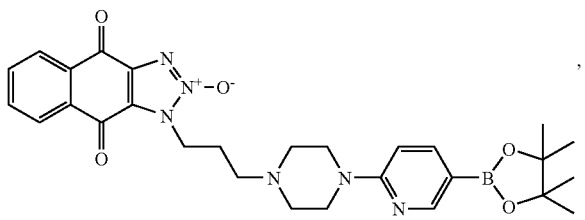
113
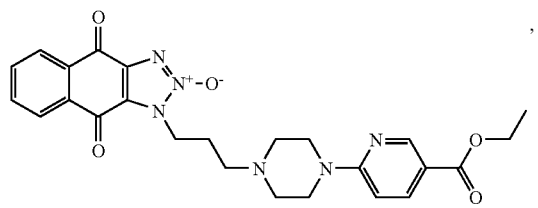
115
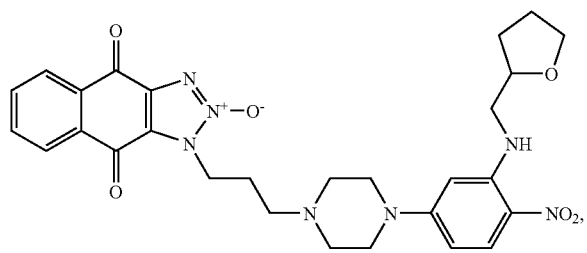
117
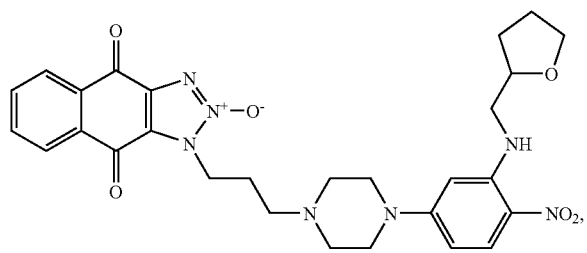
119
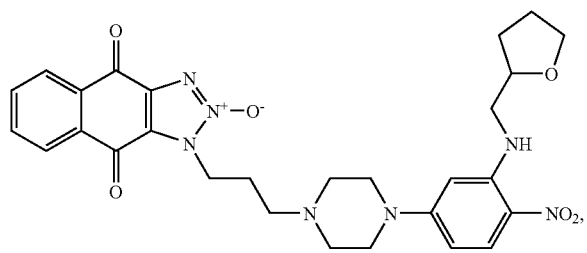
121
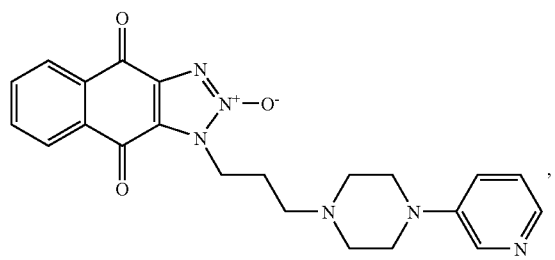
123
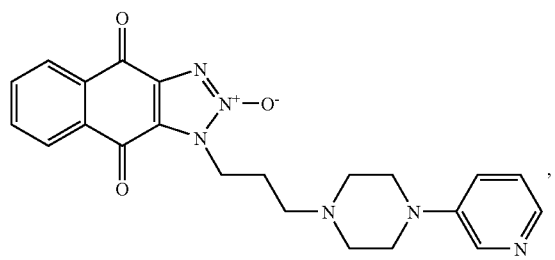
125
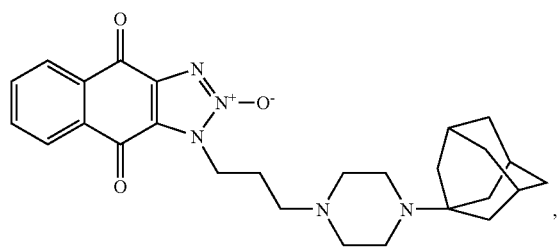
127
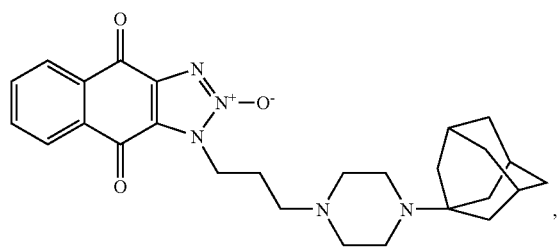
129
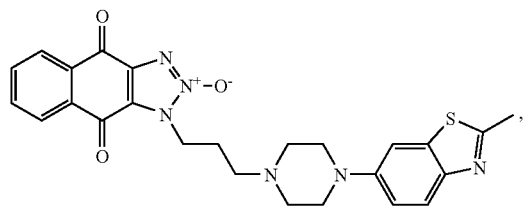
131
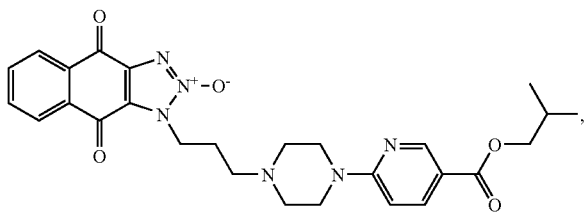

-continued
133
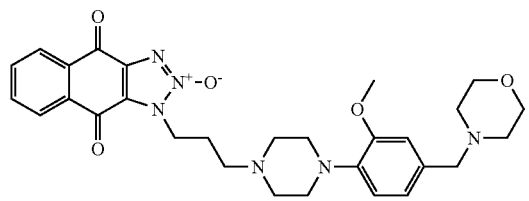
135
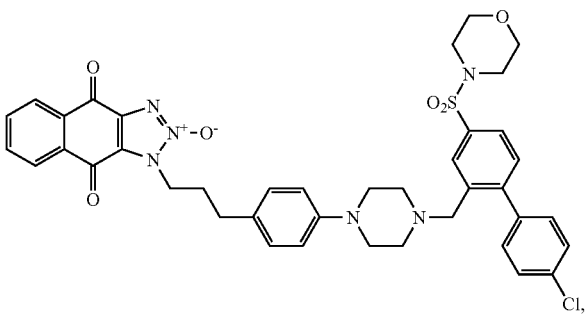
137
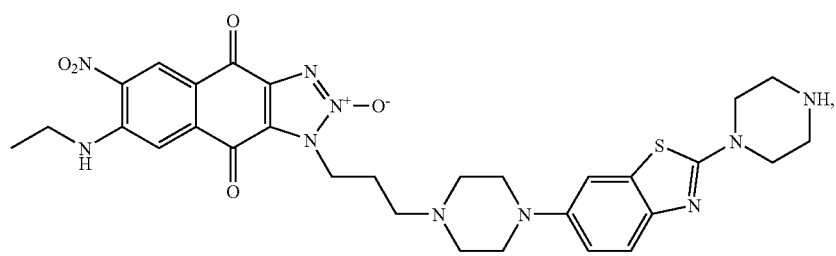
139
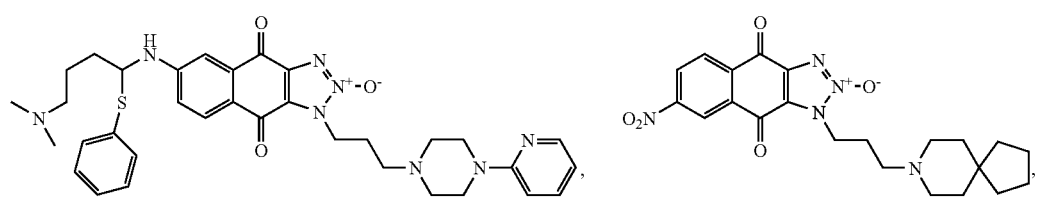
141
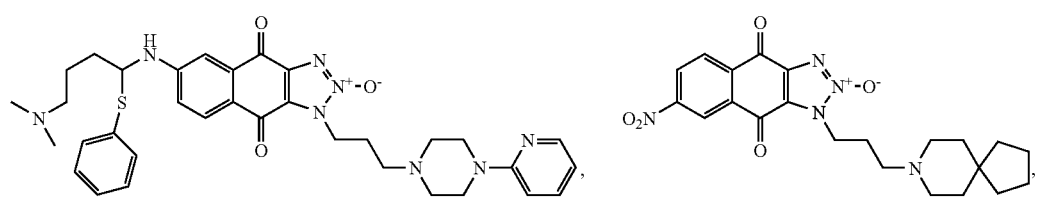
143
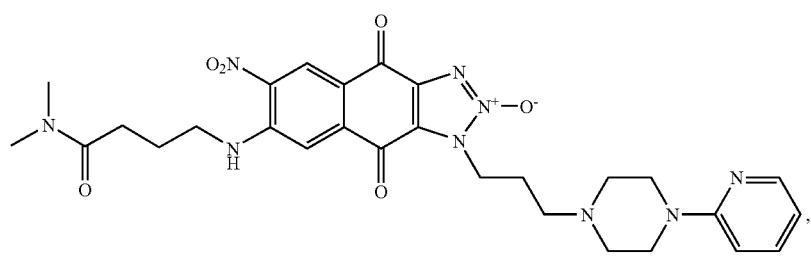
145
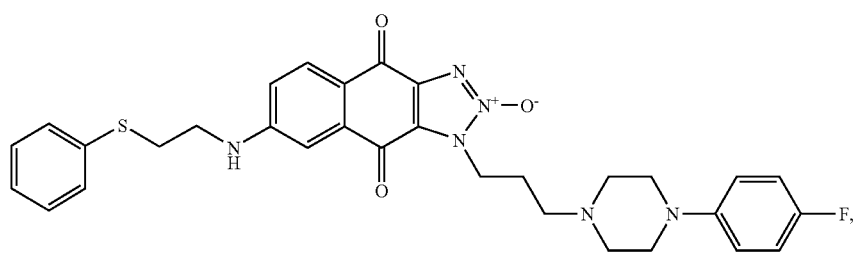
149
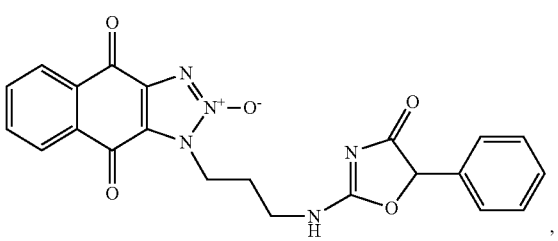

-continued
151
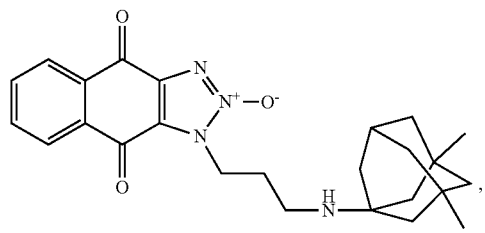
153
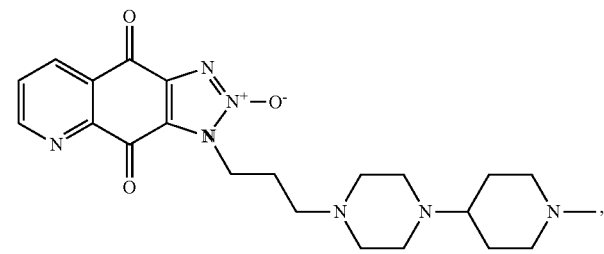
155
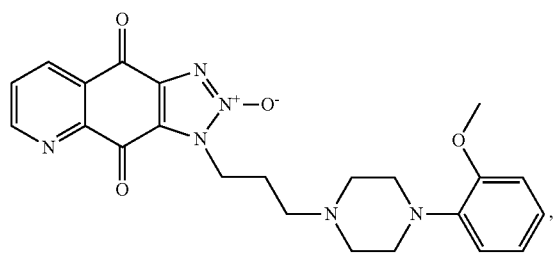
157
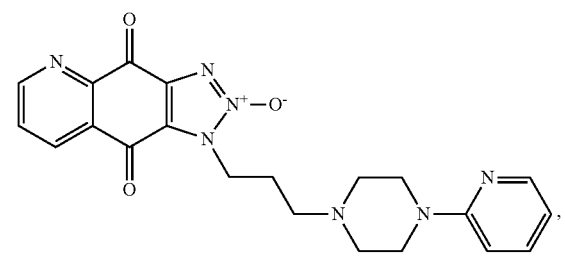
161
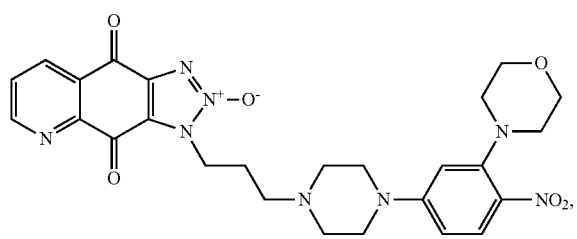
161
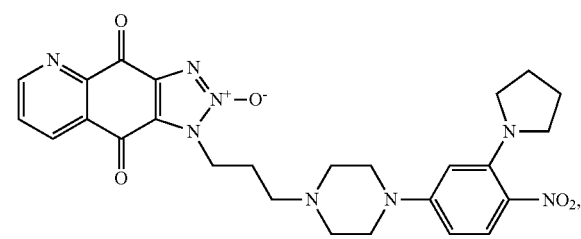
163
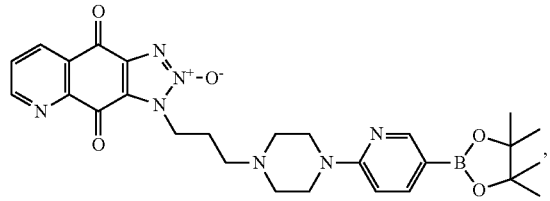
165
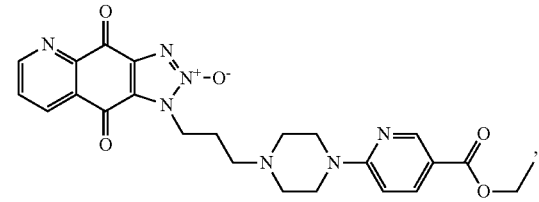
167
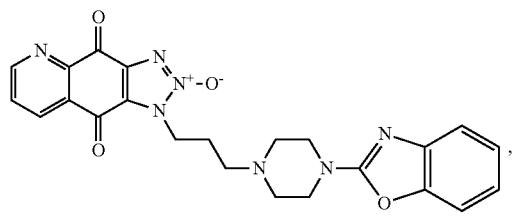
169
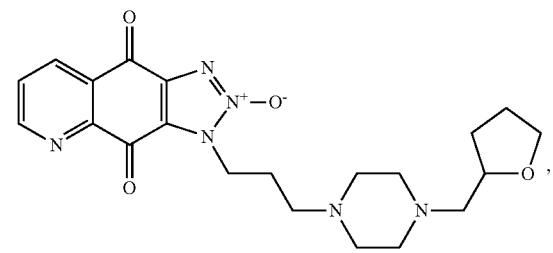
171
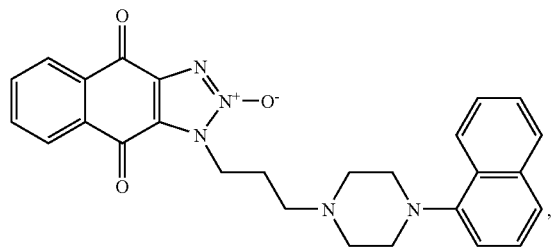
173
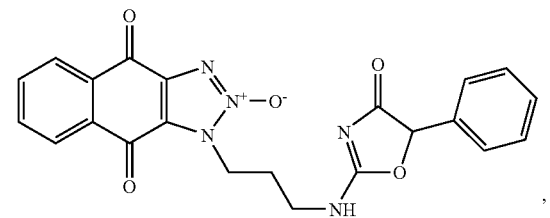

-continued
175
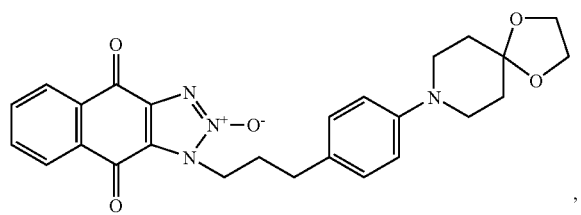
177
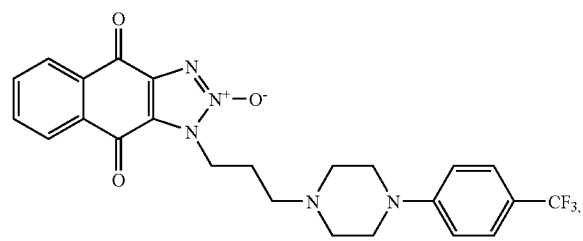
179
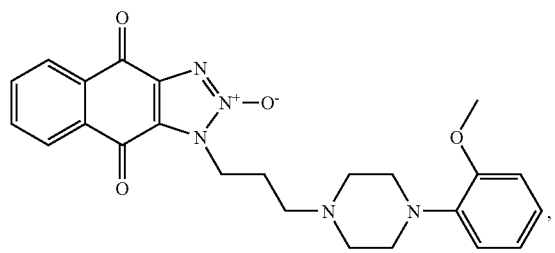
181
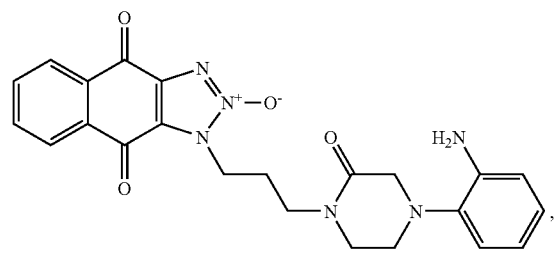
183
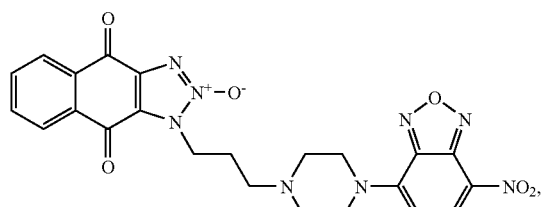
185
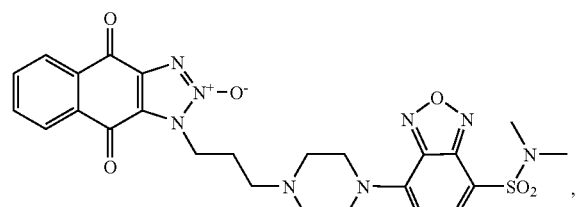
187
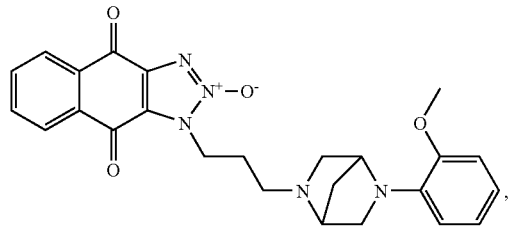
189
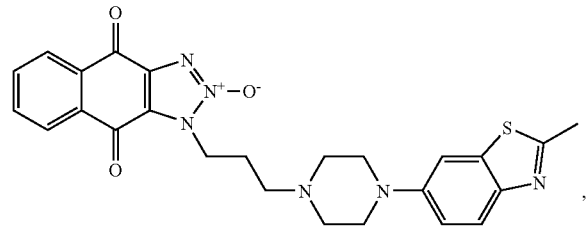
191
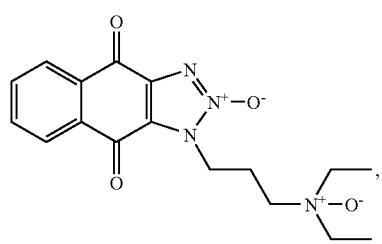
193
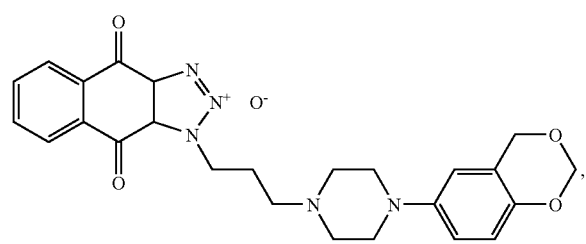
195
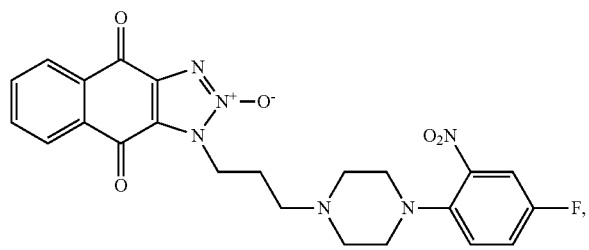
197
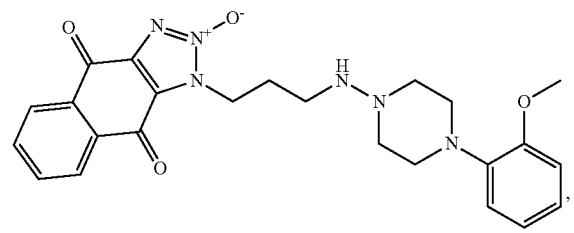

-continued
199
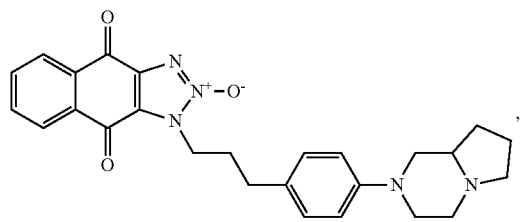
201
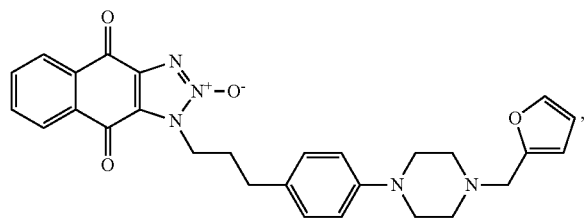
205
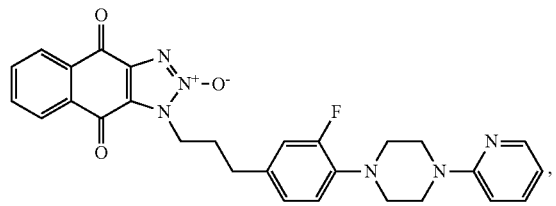
207
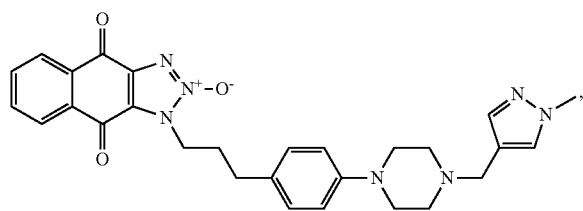
209
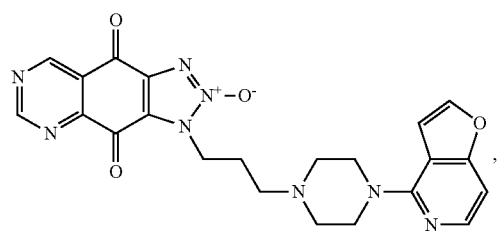
211
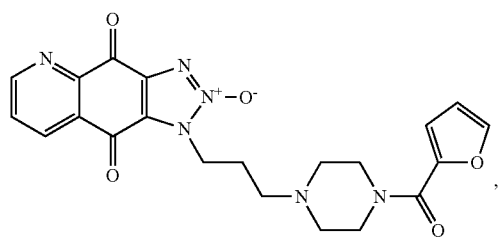
213
215
217
219
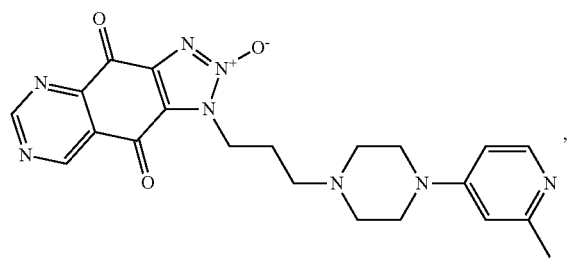
221
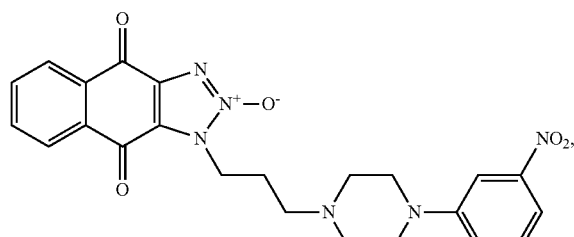

-continued
223
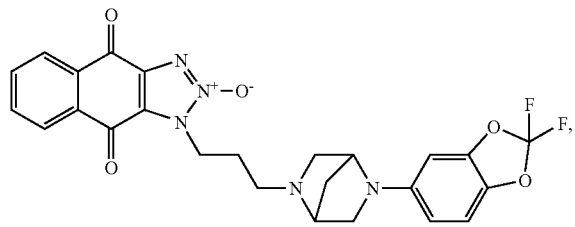
225
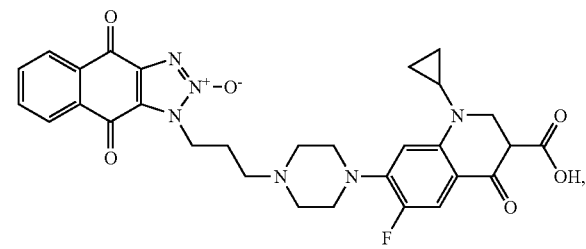
227
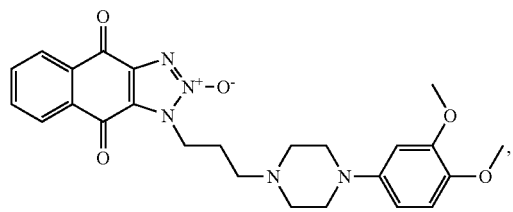
229
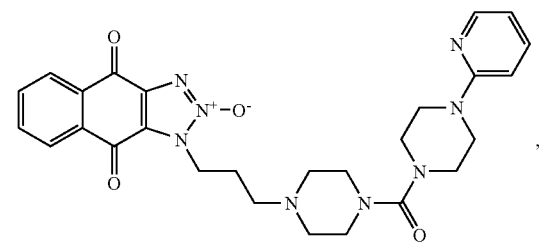
231
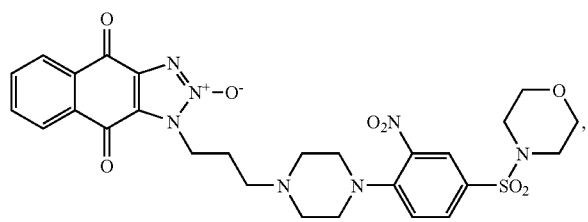
233
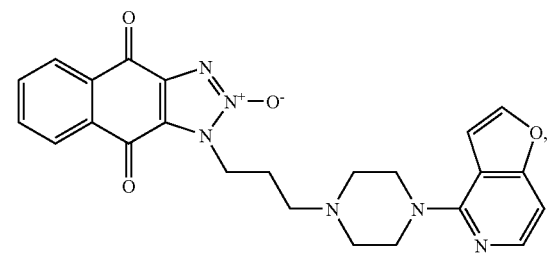
235
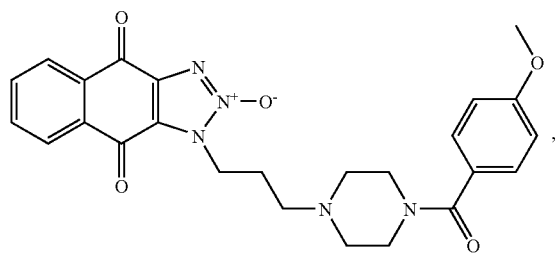
237
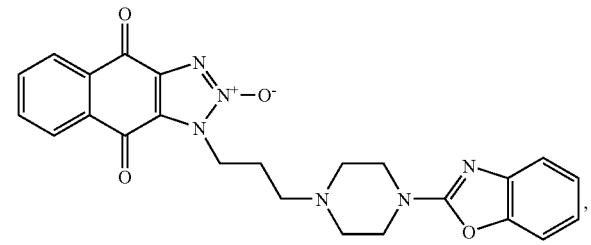
239
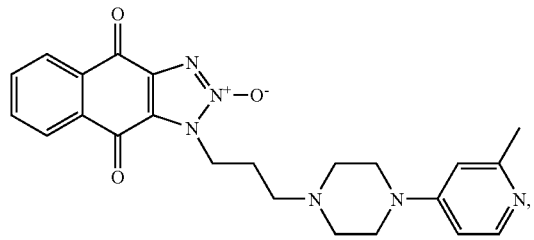
241
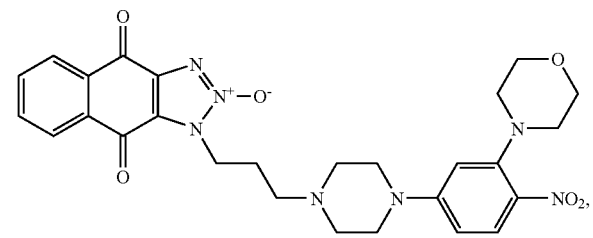
243
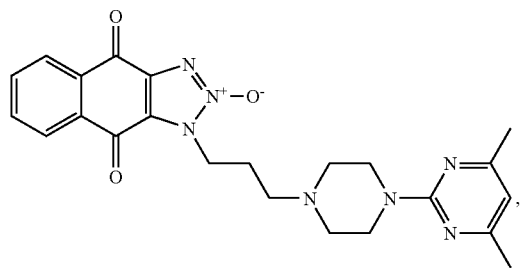
245

-continued
247
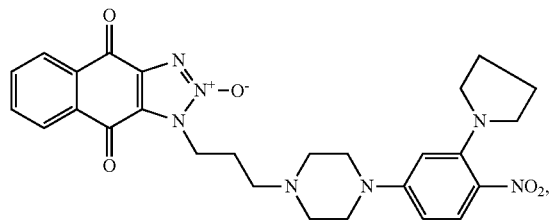
249
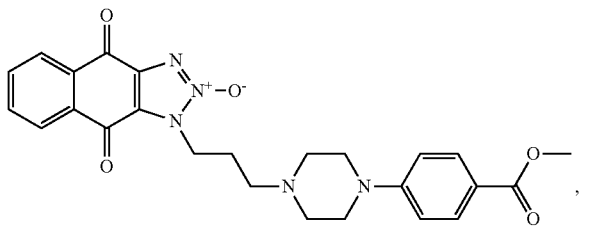
251
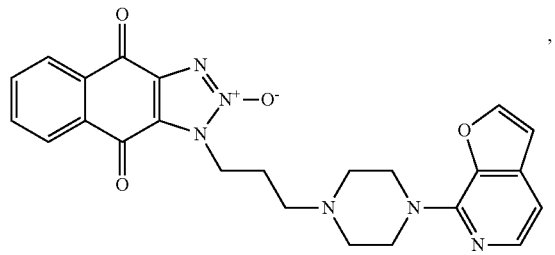
253
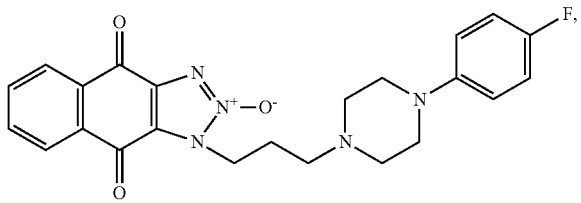
255
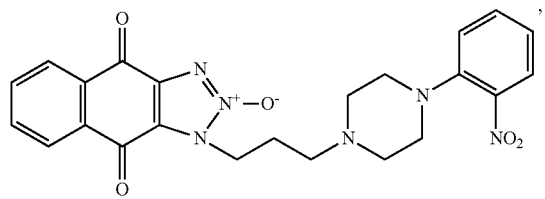
257
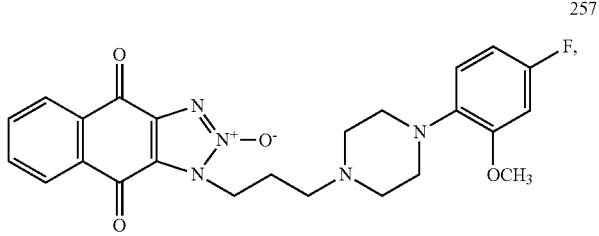
259
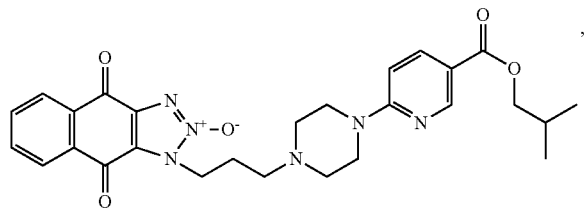
261
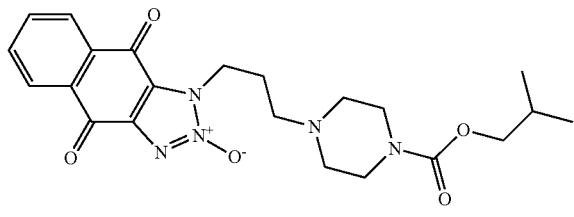
263
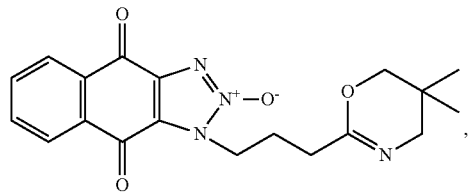
265
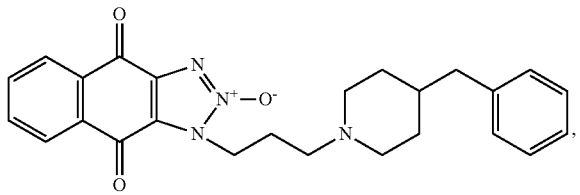
267
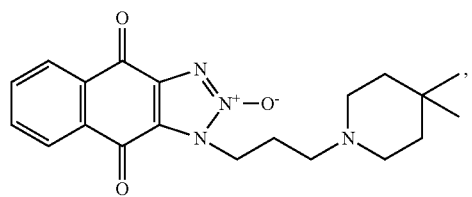
269
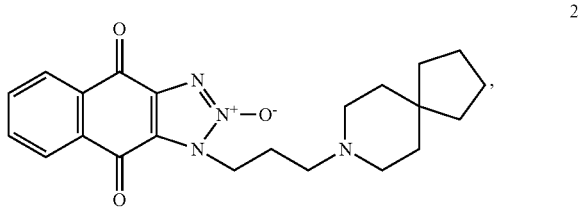
271
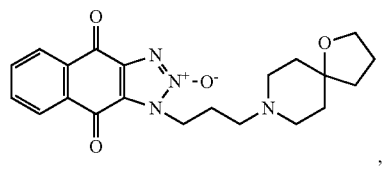
273
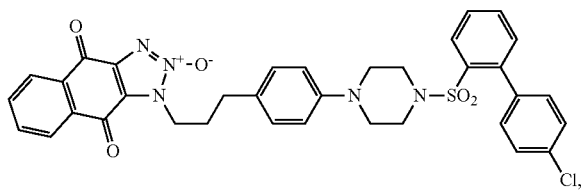

-continued
275
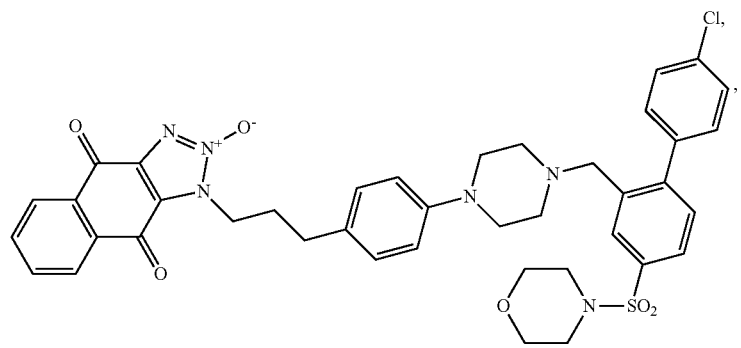
277
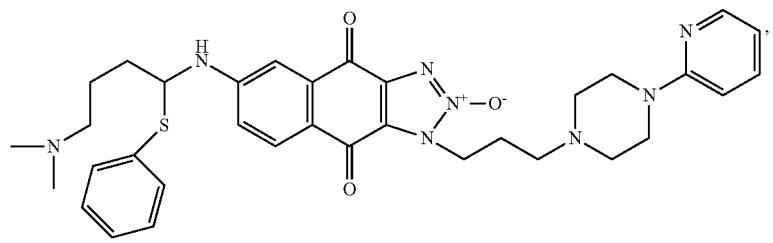
279
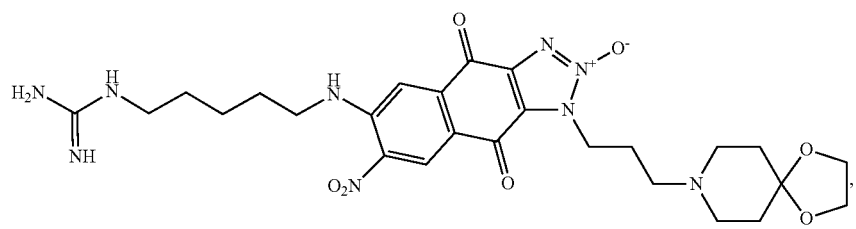
281
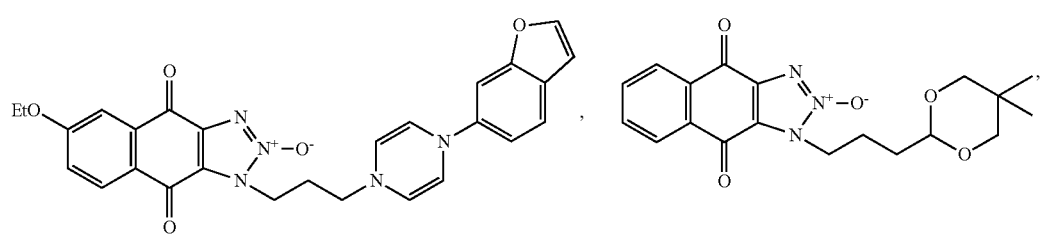
283
285
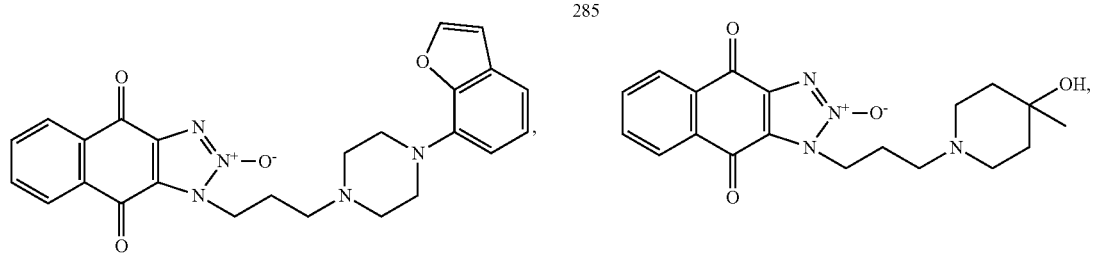
287
291
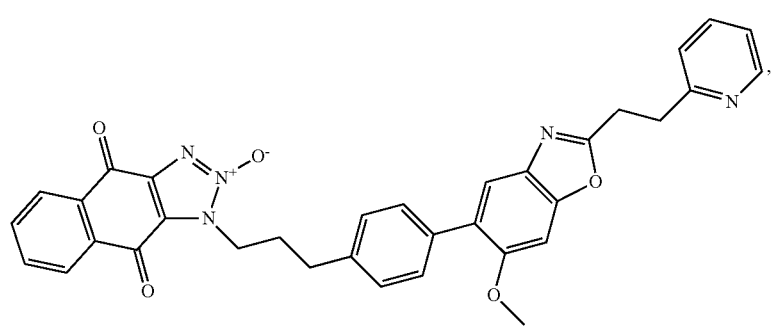

-continued
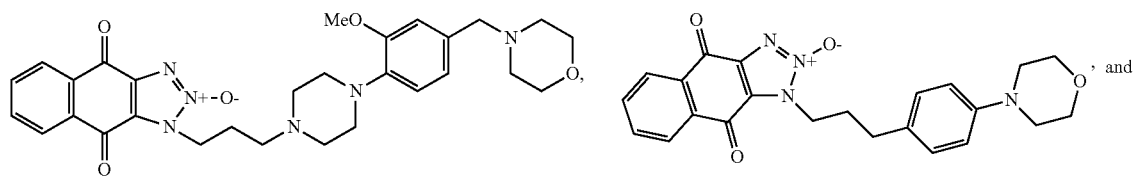
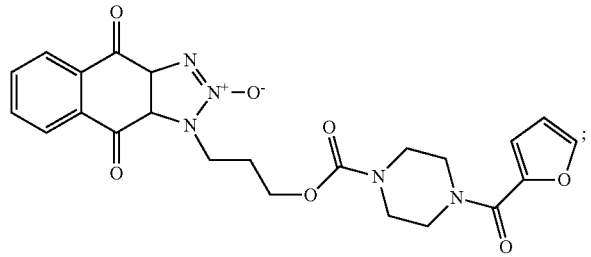
or a salt, solvate, or prodrug thereof.
* * * * *